US012808884B2

(12) United States Patent
Kim et al.

(10) Patent No.: US 12,808,884 B2
(45) Date of Patent: Nov. 24, 2026

(54) MARKER FOR DIAGNOSING NEURODEGENERATIVE DISEASE, AND THERAPEUTIC COMPOSITION

(71) Applicant: Soonchunhyang University Industry Academy Cooperation Foundation, Chungcheongnam-do (KP)

(72) Inventors: Ki Young Kim, Chungcheongnam-do (KP); Sun Joo Cha, Daehu (KP)

(73) Assignee: SOONCHUNHYANG UNIVERSITY INDUSTRY ACADEMY COOPERATION FOUNDATION, Chungcheongnam-Do (KR)

( * ) Notice: Subject to any disclaimer, the term of this patent is extended or adjusted under 35 U.S.C. 154(b) by 818 days.

(21) Appl. No.: 17/292,324

(22) PCT Filed: Nov. 13, 2018

(86) PCT No.: PCT/KR2018/013820
§ 371 (c)(1),
(2) Date: May 7, 2021

(87) PCT Pub. No.: WO2020/096103
PCT Pub. Date: May 14, 2020

(65) Prior Publication Data

US 2022/0026447 A1 Jan. 27, 2022

(30) Foreign Application Priority Data

Nov. 9, 2018 (KR) ........................ 10-2018-0137289
Nov. 9, 2018 (KR) ........................ 10-2018-0137404

(51) Int. Cl.
*G01N 33/68* (2006.01)
*A61K 38/44* (2006.01)

(52) U.S. Cl.
CPC ......... *G01N 33/6896* (2013.01); *A61K 38/44* (2013.01); *C12Y 108/05001* (2013.01); *C12Y 120/04002* (2013.01); *G01N 2800/2835* (2013.01)

(58) Field of Classification Search
CPC ....... G01N 33/6896; G01N 2800/2835; A61K 38/44; C12Y 108/05001; C12Y 120/04002
See application file for complete search history.

(56) References Cited

FOREIGN PATENT DOCUMENTS

| | | | | | |
|---|---|---|---|---|---|
| JP | 2014217339 | A | * | 11/2014 | |
| KR | 20150094311 | A | | 8/2015 | |
| KR | 101674920 | B1 | | 11/2016 | |
| WO | WO-2010011283 | A2 | * | 1/2010 | ............. A61P 21/02 |

OTHER PUBLICATIONS

Bekris et al (J Geriatr Psychiatry Neurol. Dec. 2010;23(4):213-27) (Year: 2010).*
Bekris et al (Journal of Geriatric Psychiatry and Neurology23(4) 228-242 (2010) (Year: 2010).*
D'Amico et al (Orphanet Journal of Rare Diseases 2011, 6:71) (Year: 2011).*
Nolan et al (Acta Neuropathologica Communications (2016) 4:99) (Year: 2016).*
Valle et al (Front Mol Neurosci. Jan. 23, 2017;10:5) (Year: 2017).*
Zhou et al (PLoS Genet. Oct. 2013;9(10):e1003895) (Year: 2013).*
Su et al (Free Radic Biol Med. Feb. 2014;67:460-70) (Year: 2014).*
Cayman Chemical ("Glutathione assay kit"; Dec. 7, 2016. Retrieved Mar. 1, 2024 from https://cdn.caymanchem.com/cdn/insert/703002.pdf) (Year: 2016).*
Dhar et al (Antioxid Redox Signal. Apr. 1, 2014;20(10):1550-66) (Year: 2014).*
Menon et al (J Biol Chem. Sep. 6, 2013; 288(36): 25769-25779) (Year: 2013).*
Board et al (Identification, characterization, and crystal structure of the Omega class glutathione transferases. J Biol Chem. Aug. 11, 2000;275(32):24798-806) (Year: 2000).*
Lenzi et al., 2014 (NCBI Bookshelf, A Service of the National Library of Medicine, National Institute of Health, Oversight and Review of Clinical Gene Transfer Protocols: Assessing the Role of the Recombinant DNA Advisory Committee. Washington (DC): National Academies Press (US), pp. 1-16) (Year: 2014).*
Shim et al., 2017 (Current Gene Therapy, vol. 17, No. 5, p. 1-18) (Year: 2017).*
Tora et al (The challenges of developing a gene therapy for amyotrophic lateral sclerosis, Expert Review of Neurotherapeutics, 17:4, 323-325) (Year: 2017).*
Sun, S., Ling, SC., Qiu, J. et al. ALS-causative mutations in FUS/TLS confer gain and loss of function by altered association with SMN and U1-snRNP. Nat Commun 6, 6171 (2015). (Year: 2015).*
Scekic-Zahirovic, J., Oussini, H.E., Mersmann, S. et al. Motor neuron intrinsic and extrinsic mechanisms contribute to the pathogenesis of FUS-associated amyotrophic lateral sclerosis. Acta Neuropathol 133, 887-906 (2017). (Year: 2017).*

(Continued)

*Primary Examiner* — Thomas J. Visone
*Assistant Examiner* — Georgiana C Reglas
(74) *Attorney, Agent, or Firm* — Tarolli, Sundheim, Covell & Tummino LLP

(57) ABSTRACT

A method for diagnosing a neurodegenerative disease amyotrophic lateral sclerosis (ALS) is provided, the method includes the steps of measuring a glutathionylation level of a FUS protein from a subject-derived biological sample using a preparation for measuring a glutathionylation level of a FUS protein, comparing the glutathionylation level of the FUS protein with a glutathionylation level of a FUS protein of a normal control sample, wherein an increased glutathionylation level of the FUS protein compared to the normal control sample is indicative of the subject having ALS, and administering omega class glutathione transferase 1 (GSTO1) or omega class glutathione transferase 2 (GstO2) gene or a protein encoding the same to a subject indicated as having ALS.

5 Claims, 46 Drawing Sheets

Specification includes a Sequence Listing.

(56) References Cited

OTHER PUBLICATIONS

Neumann M, Roeber S, Kretzschmar HA, Rademakers R, Baker M, Mackenzie IR. Abundant FUS-immunoreactive pathology in neuronal intermediate filament inclusion disease. Acta Neuropathol. Nov. 2009; 118(5):605-16 (Year: 2009).*
Scekic-Zahirovic et al. Toxic gain of function from mutant FUS protein is crucial to trigger cell autonomous motor neuron loss. EMBO J. May 17, 2016;35(10):1077-97. (Year: 2016).*
Sun Joo Cha, et al., "Protein Glutathionylation in the Pathogenesis of Neurodegenerative Diseases", Oxidative Medicine and Cellular Longevity, vol. 2017, Article ID 2818565, 9 pages, 2017. https://doi.org/10.1155/2017/2818565.
Youngjo Kim, et al., "Omega Class Glutathione S-Transferase: Antioxidant Enzyme in Pathogenesis of Neurodegenerative Diseases", Oxidative Medicine and Cellular Longevity, vol. 2017, Article ID 5049532, 6 pages, 2017. https://doi.org/10.1155/2017/5049532.
Board, P.G., et al., Structure, function and disease relevance of Omega-class glutathione transferases. Arch Toxicol 90, 1049-1067 (2016), 19 pgs. https://doi.org/10.1007/s00204-016-1691-1.
Elsmarieke Van De Giessen, et al., Association study on glutathione S-transferase omega 1 and 2 and familial ALS, Amyotrophic Lateral Sclerosis, 9:2, 2008; 4 pgs., DOI: 10.1080/17482960701702553.
Valle Cristiana, et al.; "Cysteine Modifications in the Pathogenesis of ALS"; Journal, Frontiers in Molecular Neuroscience, vol. 10, 2017; 8 pgs. https://www.frontiersin.org/article/10.3389/fnmol.2017.00005; DOI10.3389/fnmol.2017.00005; ISSN1662-5099.
Professor Ian RA Mackenzie, MD, et al.; "TDP-43 and FUS in amyotrophic lateral sclerosis and frontotemporal dementia"; The Lancet, Neurology, vol. 9, Issue 10, p. 995-1007, Oct. 1, 2010; 35 pgs.
Zhihui Sun, et al.; "Molecular Determinants and Genetic Modifiers of Aggregation and Toxicity for the ALS Disease Protein FUS/TLS"; Research Article—PLOS Biology; plos.org; Apr. 26, 2011; 19 pgs. https://doi.org/10.1371/journal.pbio.1000614.
Yanbo Chen, et al.; "PINK1 and Parkin are genetic modifiers for FUS-induced neurodegeneration"; Human Molecular Genetics, vol. 25, Issue 23, Dec. 1, 2016, pp. 5059-5068, https://doi.org/10.1093/hmg/ddw310.
Jäckel, S., et al.; "Nuclear Import Factor transportin and Arginine Methyltransferase 1 Modify FUS Neurotoxicity in *Drosophila*"; Neurobiology of Disease, vol. 74, Feb. 2015; 2 pgs.
NCBI Reference Sequence: NP_004951.1; RNA-binding protein FUS isoform 1 [*Homo sapiens*]; Jul. 17, 2019; 6 pgs.; https://www.ncbi.nlm.nih.gov/protein/4826734?sat-47&satkey=9884.
GenBank: AF212303.1; *Homo sapiens* glutathione transferase omega (GSTO1) mRNA, complete cds; Jul. 17, 2019; 1 pg.; https://www.ncbi.nlm.nih.gov/nucleotide/AF212303.1?report=genbank&log$=nuclali . . . .
NCBI Reference Sequence: NM_168277.2; *Drosophila melanogaster* glutathione S transferase 02, transcript variant A (GstO2), mRNA; Jul. 17, 2019; 3 pgs.; https://www.ncbi.nlm.nih.gov/nuccore/442631056?sat=46&satkey=145604130.

* cited by examiner

[FIG. 13A]
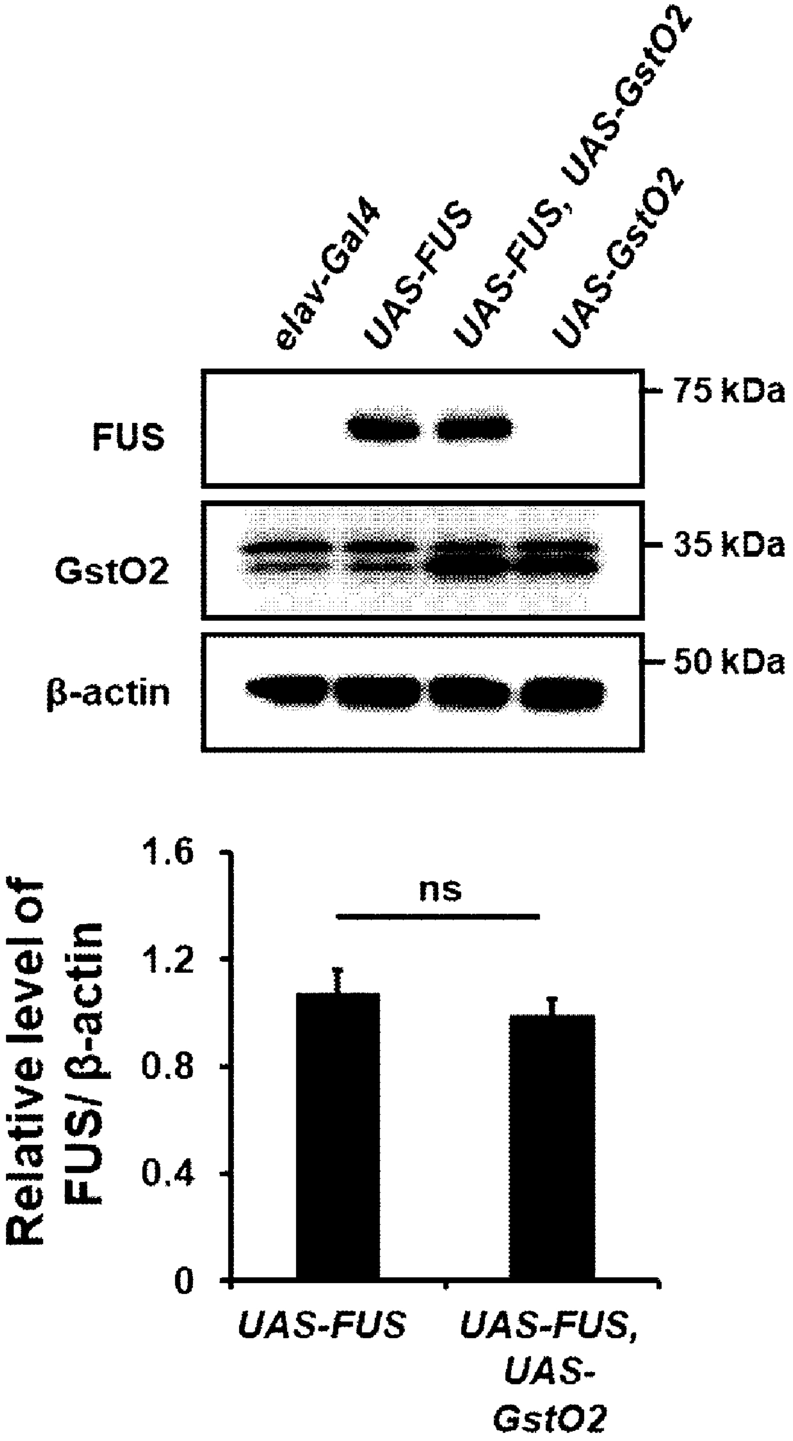

[FIG. 13B]
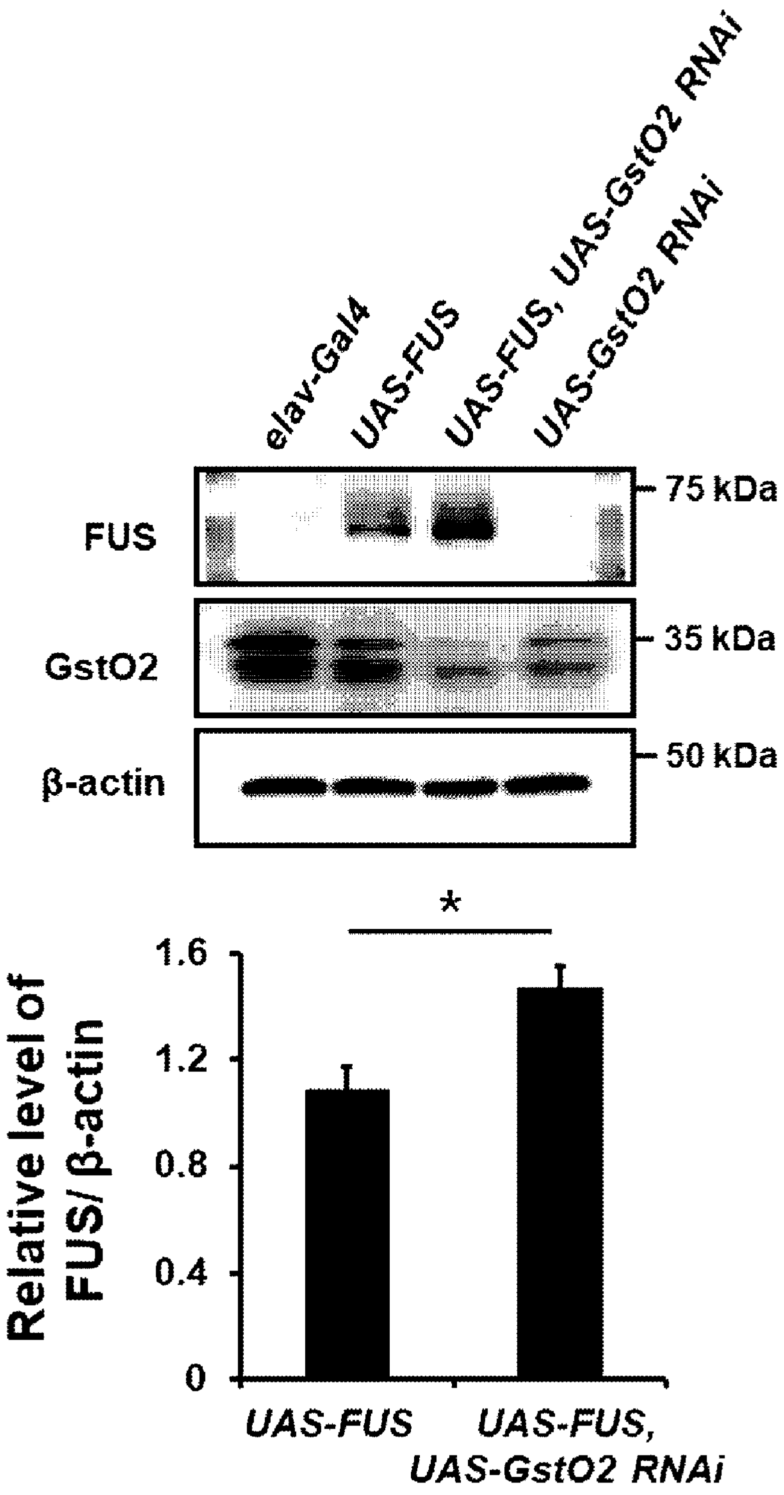

[FIG. 13C]
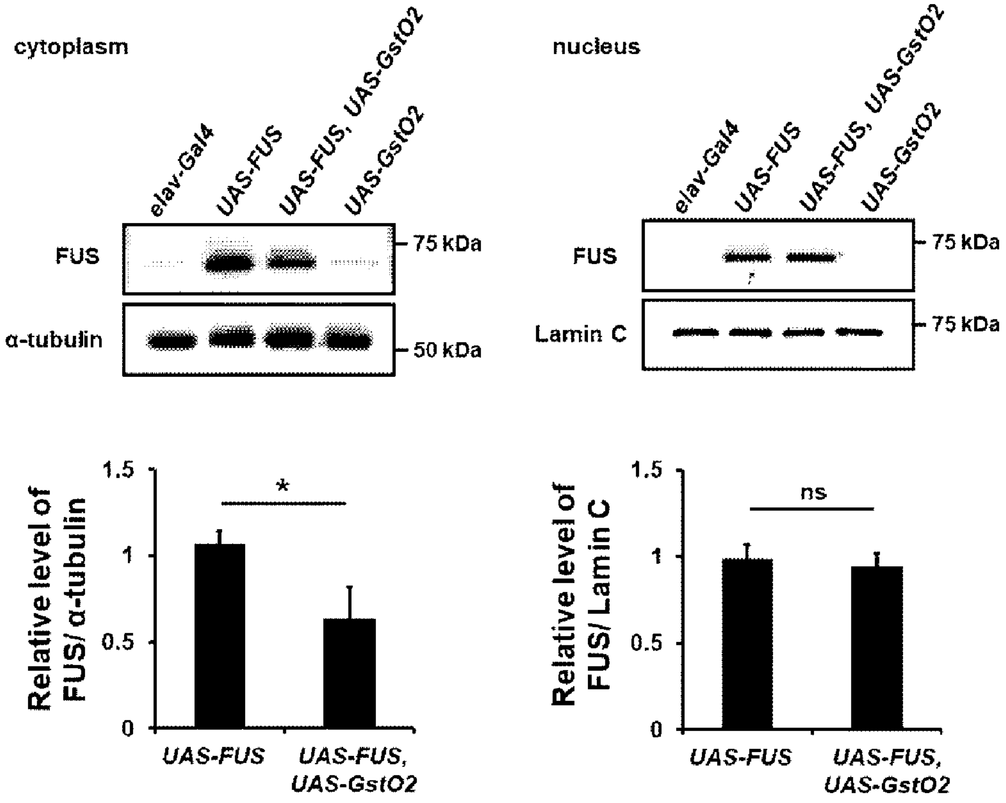

[FIG. 14A]
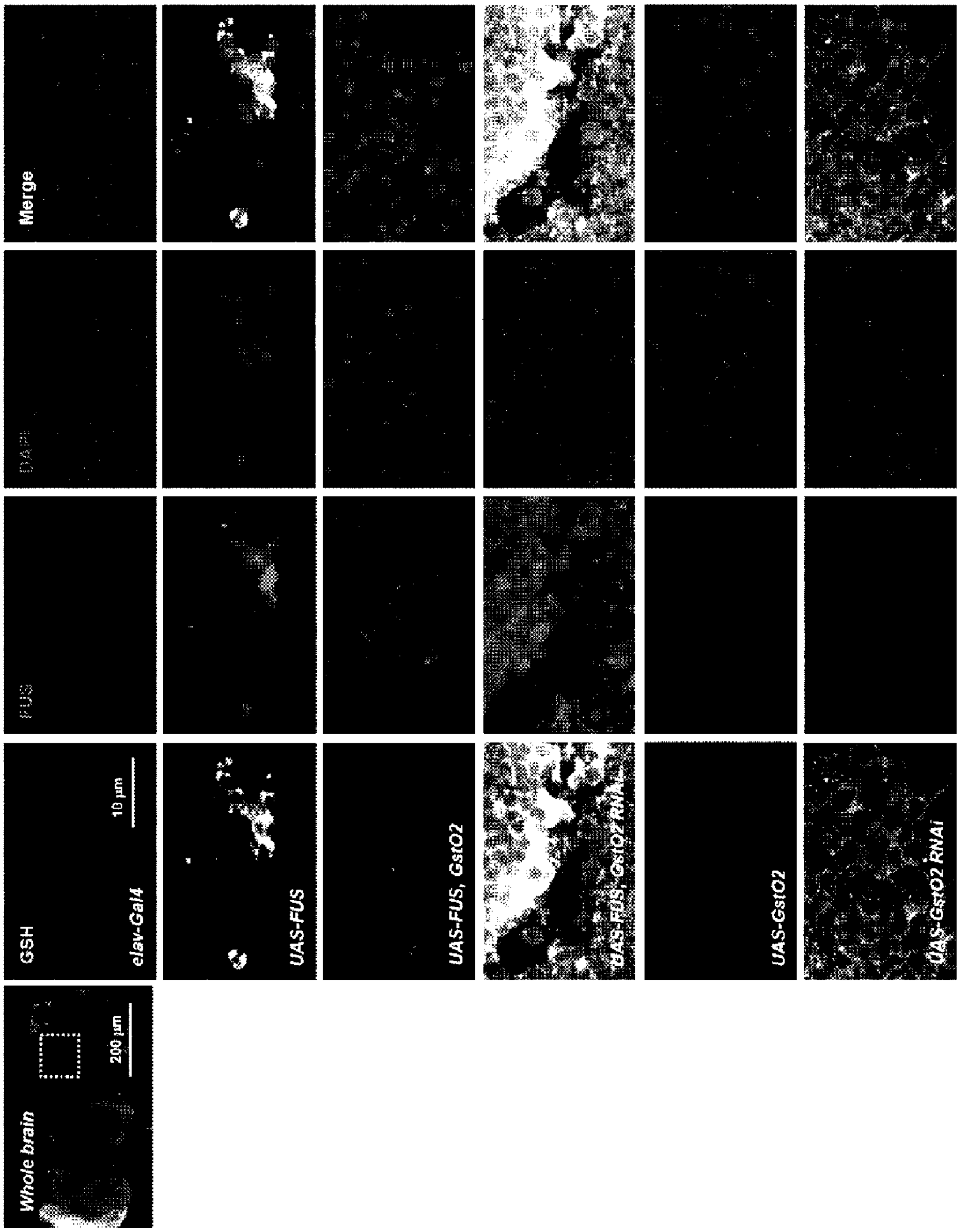

[FIG. 14B]
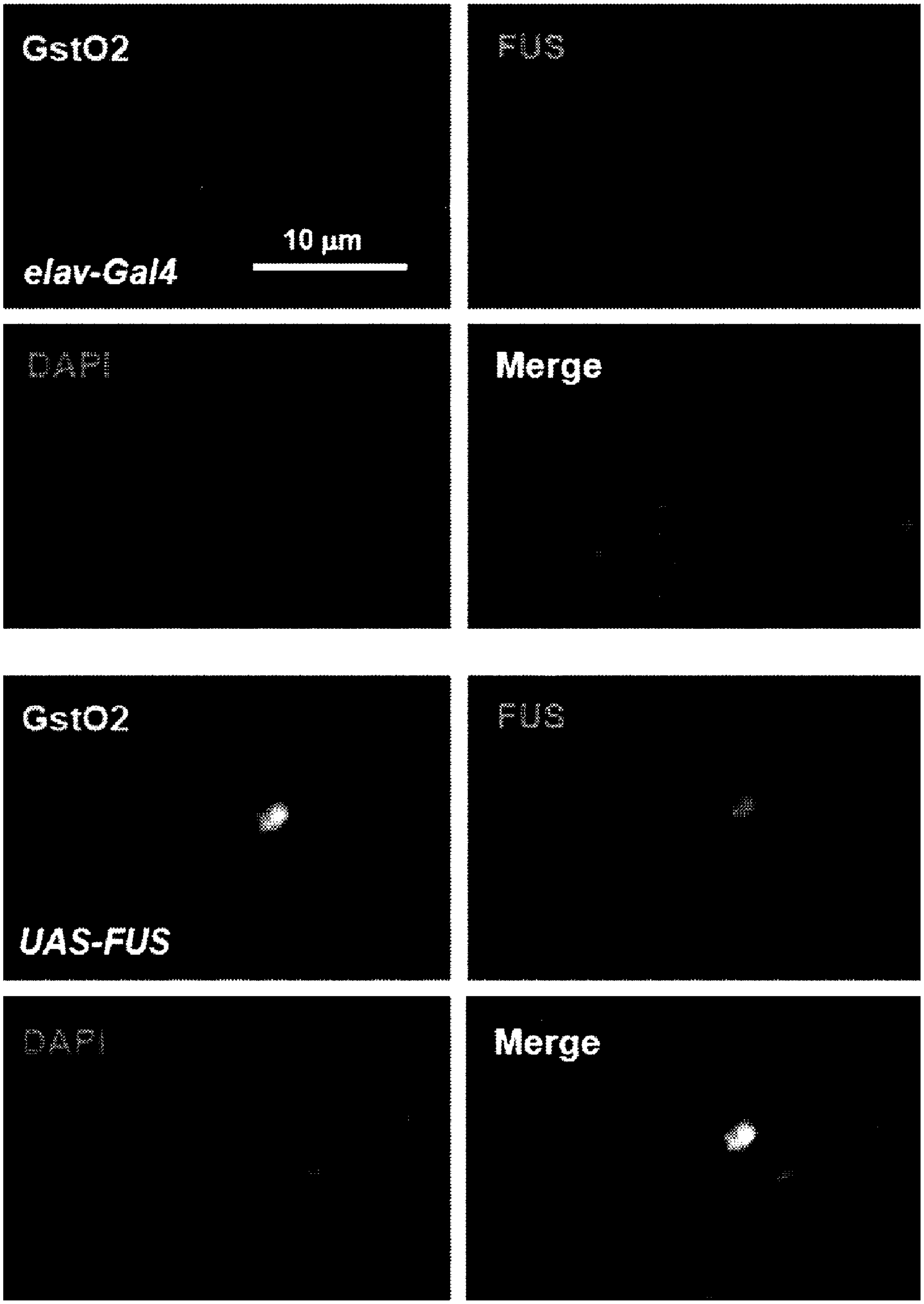

[FIG. 15B]
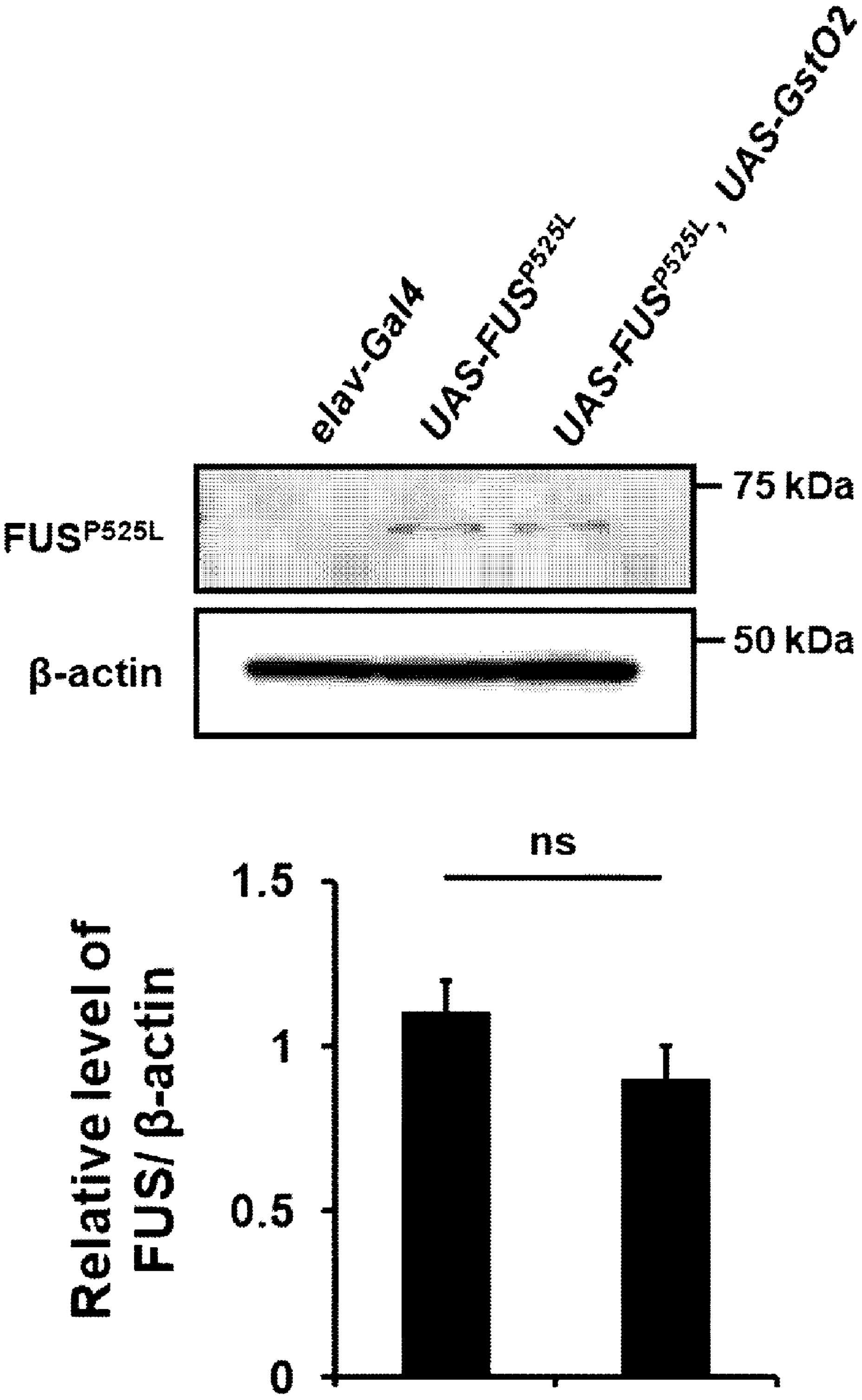

MARKER FOR DIAGNOSING NEURODEGENERATIVE DISEASE, AND THERAPEUTIC COMPOSITION

SEQUENCE LISTING

The instant application contains a Sequence Listing which has been submitted electronically in .txt format and is hereby incorporated by reference in its entirety. Said copy, created on May 6, 2021, is named ISIS030614USPCT.txt and is 10,694 bytes in size.

TECHNICAL FIELD

The present disclosure relates to a marker for diagnosing a neurodegenerative disease and a use thereof, and more particularly, to a marker composition for diagnosing a neurodegenerative disease, which includes a glutathionylated FUS protein, a composition for diagnosing a neurodegenerative disease, which includes a preparation of measuring a glutathionylation level of a FUS protein, a kit for diagnosing a neurodegenerative disease, which includes the composition, and a method of providing information on diagnosis of a neurodegenerative disease using the same.

In addition, the present disclosure relates to a composition for treating a neurodegenerative disease, which includes GstO2, and more particularly, to a composition for preventing or treating a neurodegenerative disease, which includes GstO2 inducing deglutathionylation of a FUS protein.

BACKGROUND ART

Amyotrophic lateral sclerosis (ALS) is a fatal adult-onset neurodegenerative disease which is characterized by the gradual degeneration of motoneurons. ALS causes progressive muscle weakness, leading to fatal muscle atrophy and paralysis, and death within 3 to 5 years after the onset of the disease. ALS may be classified into sporadic ALS whose cause is not known, and familial ALS due to genetic defects in proteins directly related to pathology, such as superoxide dismutase1 (SOD1), transactive response DNA-binding protein-43 (TDP-43), fused in sarcoma (FUS) or TATA-binding protein-associated factor15 (TAF15). It was revealed that mutant-type TDP-43 has toxicity in neurons, and mislocalization of the protein is associated with the onset of ALS.

In addition, protein aggregates are characteristically found in age-related neurodegenerative diseases (NDs) for example, Parkinson's disease (PD), Alzheimer's disease (AD), Huntington's disease (HD) and amyotrophic lateral sclerosis (ALS, also called Lou Gehrig's disease).

Fused-in-Sarcoma (FUS) is a RNA and DNA-binding protein, and it is known that the N-terminus of the FUS protein is associated with transcriptional activity, and the C-terminus thereof is associated with protein and RNA binding. The FUS protein includes recognition sites for AP2, GCF and Sp1, which are transcription factors, and in a recent study, various types of mutant FUS proteins have been identified in patients with ALS or frontotemporal dementia. It was revealed that the mutant FUS protein escaped from its original position in the nucleus and then was located in a stress granule, thereby forming an aggregate.

Meanwhile, FUS mutations were shown in most ALS patients (Mackenzie et al., 2010), a $FUS^{P525L}$ mutation indicates mislocalization in the cytoplasm and is associated with acute FUS-induced ALS (Sun et al., 2011), and wild-type FUS and its variant, $FUS^{P525L}$, are known to exhibit the same phenotype, such as rough eyes, and reduced locomotive activity in *Drosophila* (Chen et al., 2016; Jackel et al., 2015).

Although ALS cannot be diagnosed with magnetic resonance imaging (MRI) or a blood test, it can be diagnosed through a physical examination based on a patient's symptoms and a physical examination by experienced medical personnel. Studies on a method for diagnosing ALS by measuring the expression level of MARCH5 and MFN2 genes or protein activity have been attempted (Korean Patent No. 10-1674920), and there is still a lack of research on a marker or composition for ALS diagnosis related to a FUS protein and an aggregate of the FUS protein.

In addition, little is known about the mechanisms involved in the abnormal location of FUS mutant proteins and aggregate accumulation, which are found in ALS patients or frontotemporal dementia patients, and there are no therapeutic methods based thereon. As described above, various studies have been attempted to develop therapeutic drugs by confirming the formation of FUS aggregates and their action mechanisms (Korean Patent No. 10-1576602), but are still insufficient.

DISCLOSURE

Technical Problem

Therefore, the inventors found that a FUS protein that should usually be located in the nucleus is located in the form of a glutathionylated FUS protein aggregate in the cytoplasm while searching for a novel marker for diagnosing a neurodegenerative disease, and confirmed that the glutathionylated FUS protein can be a novel marker that is able to diagnose a neurodegenerative disease, and thus the present disclosure was completed.

In addition, the present disclosure is devised to solve the above-described problem, and as a result of various studies, it was confirmed that the formation of a protein aggregate by the glutathionylation of a FUS protein known as an ALS-induced protein and its deposition in the cytoplasm of brain neurons cause ALS, and the glutathionylation inhibitory activity of a FUS protein of omega class glutathione transferase (GSTO) was confirmed. Based on this, the present disclosure was completed.

The present disclosure is directed to providing a marker composition for diagnosing a neurodegenerative disease, which includes a glutathionylated FUS protein.

The present disclosure is also directed to providing a composition for diagnosing a neurodegenerative disease, which includes a preparation for measuring the glutathionylation level of a FUS protein and a kit for diagnosing a neurodegenerative disease, which includes the composition.

The present disclosure is also directed to providing a method of providing information for diagnosing a neurodegenerative disease, which includes measuring the glutathionylation level of a FUS protein in a subject-derived biological sample and comparing the glutathionylation level with that of a normal person.

The present disclosure is also directed to providing a pharmaceutical composition for preventing or treating a neurodegenerative disease, which includes GSTO1 or omega class glutathione transferase 2 (GstO2) gene or a protein encoding the gene as an active ingredient.

However, technical problems to be solved in the present disclosure are not limited to the above-described problems, and other problems which are not described herein will be fully understood by those of ordinary skill in the art from the following descriptions.

Technical Solution

To attain the above-described objects, the present disclosure provides a marker composition for diagnosing a neurodegenerative disease, which includes a glutathionylated FUS protein.

In one embodiment of the present disclosure, the neurodegenerative disease may be amyotrophic lateral sclerosis (ALS).

In another embodiment of the present disclosure, the FUS protein may be glutathionylated at a Cys-447 residue.

In addition, the present disclosure provides a composition for diagnosing a neurodegenerative disease, which includes a preparation for measuring the glutathionylation level of a FUS protein.

In one embodiment of the present disclosure, the FUS protein may consist of the amino acid sequence represented by SEQ ID NO: 1.

In one embodiment of the present disclosure, the neurodegenerative disease may be ALS.

In addition, the present disclosure provides a kit for diagnosing a neurodegenerative disease, which includes the composition.

In addition, the present disclosure provides a method for providing information on diagnosis of a neurodegenerative disease, which includes: a) measuring a glutathionylation level of a FUS protein from a subject-derived biological sample and b) comparing the glutathionylation level of the FUS protein with a glutathionylation level of a FUS protein of a normal control sample.

In addition, the present disclosure provides a pharmaceutical composition for preventing or treating a neurodegenerative disease, which includes a GSTO1 or GstO2 gene or a protein encoding the same as an active ingredient.

In one embodiment of the present disclosure, the GSTO1 gene may consist of the base sequence represented by SEQ ID NO: 2.

In another embodiment of the present disclosure, the GSTO1 protein may consist of the amino acid sequence represented by SEQ ID NO: 3.

In still another embodiment of the present disclosure, the GstO2 gene may consist of the base sequence represented by SEQ ID NO: 4.

In yet another embodiment of the present disclosure, the GstO2 protein may consist of the amino acid sequence represented by SEQ ID NO: 5.

In yet another embodiment of the present disclosure, the neurodegenerative disease may be ALS.

In yet another embodiment of the present disclosure, the composition may inhibit the glutathionylation of a FUS protein.

In yet another embodiment of the present disclosure, the glutathionylation of the FUS protein may be glutathionylation at the Cys-447 residue of FUS.

In addition, the present disclosure provides a method of preventing or treating a neurodegenerative disease, which includes administering the composition to a subject.

In addition, the present disclosure provides a use of the composition for preventing or treating a neurodegenerative disease.

Advantageous Effects

The inventors identified that a glutathionylated FUS protein serves as a marker for diagnosing a neurodegenerative disease, and thus a composition for diagnosing a neurodegenerative disease according to the present disclosure will contribute to early diagnosis of a neurodegenerative disease.

In addition, the inventors identified that the glutathionylation of FUS known as an ALS-inducing protein is the ALS pathogenesis mechanism that increases aggregation in the cytoplasm and neurotoxicity, and confirmed that a composition for preventing or treating a neurodegenerative disease according to the present disclosure includes GSTO1 or GstO2, which induces the deglutathionylation of a FUS protein, has an effect of inhibiting brain cytoplasm aggregation and neurocytotoxicity. Therefore, it is expected to be effectively used in preventing, treating or alleviating a neurodegenerative disease.

DESCRIPTION OF DRAWINGS

FIG. 3B is an image showing that a reduced glutathione (GSH) generated by the glutathionylation of a human wild-type FUS protein is located in the cytoplasm of N2a.

FIG. 4B is an image showing that a reduced glutathione (GSH) generated by the glutathionylation of a human mutant $FUS^{P525L}$ protein is located in the cytoplasm of N2a.

FIG. 10C shows the result of confirming FUS and a human mutant $FUS^{P525L}$ protein aggregate in the cytoplasm of N2a.

FIG. 13A shows the result of immunoblotting of a brain extract of FUS-expressing flies according to GstO2.

FIG. 13B shows the result of immunoblotting of a brain extract of FUS-expressing flies according to Gsto2-knockdown.

FIG. 13C shows the result of nuclear/cytoplasmic fraction analysis for FUS-expressing flies according to GstO2.

FIG. 14A shows the result of double immunofluorescence analysis to confirm the regulation of FUS glutathionylation in neurons of FUS-expressing flies according to GstO2.

FIG. 14B shows the result of confirming glutathionylation by endogenous GstO2.

FIG. 15B shows the result of immunoblotting of a brain extract of FUSP525L-expressing flies according to GstO2.

FIG. 16C shows the result of confirming a neuronal death recovery effect according to GSTO1, which is a human homologous chromosome of GstO2.

MODES OF THE INVENTION

Figure 1A:
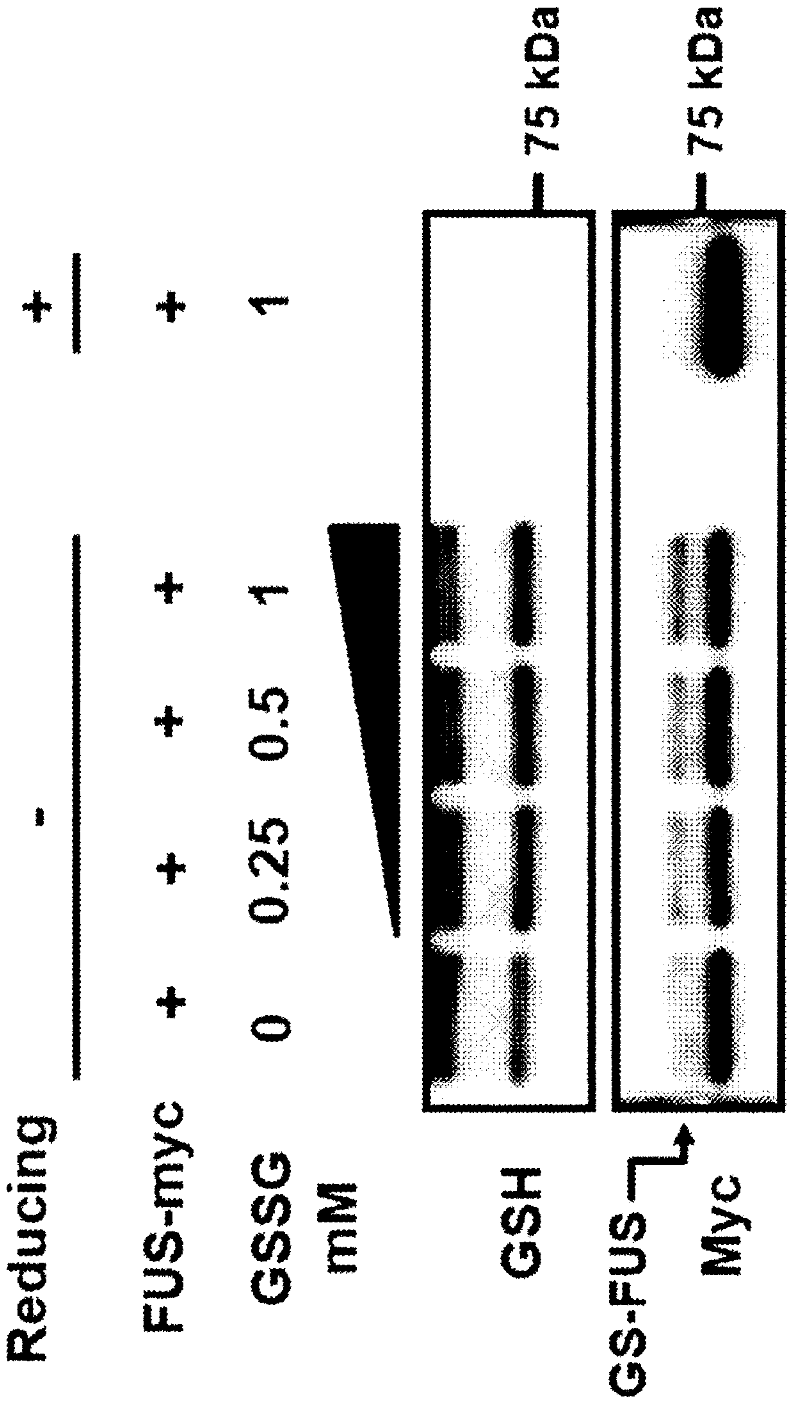
FIG. 1A shows the result of isolating a human FUS protein, which is gluttathionylated depending on the concentration of an oxidized glutathione (GSSG), by sodium dodecyl sulfate-polyacrylamide gel electrophoresis (SDS-PAGE) to confirm the glutathionylation of a human FUS protein.

Hereinafter, the present disclosure will be described in detail.

As a result of various studies on neurodegenerative diseases, the inventors found that the glutathionylation of a FUS protein, which is known as one of the causes of ALS, results in formation of a FUS protein aggregate, and identified that the FUS protein aggregate serves as a marker for diagnosing ALS, and thus the invention was completed.

Therefore, the present disclosure provides a marker composition for diagnosing a neurodegenerative disease, which includes a glutathionylated FUS protein, a composition for diagnosing a neurodegenerative disease, which includes a preparation of measuring a glutathionylation level of a FUS protein, and a kit for diagnosing a neurodegenerative disease, which includes the composition.

The gene encoding a FUS protein according to the present disclosure may consist of the base sequence represented by SEQ ID NO: 1, or the amino acid sequence represented by SEQ ID NO: 2. Here, the gene encoding a FUS protein may include a base sequence having 70% or more, preferably 80% or more, more preferably 90% or more, and most preferably 95% or more sequence homology with the base sequence represented by SEQ ID NO: 1.

The target disease of the present disclosure, "neurodegenerative disease" refers to the generic term for diseases leading to the death of neurons in one or various part(s) of the nervous system. Types of neuron death include necrosis or apoptosis. The target disease includes preferably Alzheimer's disease, mild cognitive impairment, stroke, vascular dementia, frontotemporal dementia, Lewy body dementia, Creutzfeldt-Jacob disease, traumatic head injuries, syphilis, acquired immunodeficiency syndrome, other viral infections, brain abscesses, brain tumors, multiple sclerosis, Parkinson's disease, Huntington's disease, Pick's disease, ALS, epilepsy, and ischemia, and more preferably ALS, but the present disclosure is not limited thereto.

The "fused in sarcoma (FUS) protein" known as one of the causes of a neurodegenerative disease in the present disclosure is a RNA and DNA-binding protein, and here, it is known that the N-terminus of FUS is associated with transcriptional activity, and the C-terminus thereof is associated with protein and RNA binding.

The term "glutathionylation" used herein refers to the formation of a disulfide bond between a cysteine and a reduced glutathione (GSH). The glutathionylation of a protein induces changes in the structure and function of a protein.

As it was described that the formation of a FUS protein aggregate caused by the glutathionylation of a FUS protein known as an ALS-inducing protein and the deposition of the aggregate in the cytoplasm are the causes of ALS, in one embodiment of the present disclosure, by a western blotting analysis using an anti-GSH antibody and an anti-myc antibody, it was confirmed that the glutathionylation of a FUS protein occurs depending on the concentration of an oxidized glutathione (glutathione disulfide; GSSH) in vitro (see Example 2), and a glutathionylated FUS protein aggregate was confirmed in the cytoplasm of a neuron by performing an experiment for confirming whether the glutathionylation of a FUS protein occurs in vivo (see Example 3).

In another embodiment of the present disclosure, an experiment for expressing a human FUS protein and a mutant $FUS^{P525L}$ protein in Neuron2a (N2a) was performed, confirming that the glutathionylation of a human wild-type FUS protein and a mutant $FUS^{P525L}$ protein occurs in mammalian systems in the same manner as described above (see Example 4).

In still another embodiment of the present disclosure, MALDI-mass spectroscopy and sequencing of the RanBP2 zinc-finger domain were performed to confirm that GSSH-induced glutathionylation occurs at Cys-447 of the RanBP2 zinc-finger domain in a FUS protein (see Example 5).

In yet another embodiment of the present disclosure, the analysis of the solubility of a glutathionylated FUS protein and the analysis of the three-dimensional homology model of the RanBP2 zinc-finger domain of a FUS protein were performed to confirm that the glutathionylation of the FUS protein induces the formation of the protein aggregate (see Example 6).

The above results show that glutathionylation occurs at Cys-447 of the RanBP2 zinc-finger domain in the FUS protein, and a glutathionylated FUS protein aggregate is formed, and the aggregate is deposited in the cytoplasm due to low solubility, shown in FIGS. 2 to 4.

The term "diagnosis" used herein refers to, in a broad sense, judgment of the condition of a patient's disease in all aspects. The contents of the judgment include the name of a disease, etiology, a disease type, severity, the details of pathology and the presence of complications. The diagnosis in the present disclosure is determination of the occurrence and stage of progression of a neurodegenerative disease.

Another aspect of the present disclosure provides a method of providing information on diagnosis of a neurodegenerative disease, which includes measuring a glutathionylation level of a FUS protein from a subject-derived biological sample and comparing the glutathionylation level of the FUS protein with a glutathionylation level of a FUS protein in a normal control sample.

The term "method of providing information on diagnosis of a neurodegenerative disease" used herein refers to providing objective basic information required for diagnosis of a neurodegenerative disease as a preliminary step for diagnosis or predicting prognosis, but excluding a doctor's clinical judgment or opinion. The subject-derived biological sample may be, for example, tissue or a cell, but the present disclosure is not limited thereto.

In addition, as a result of various studies on treatment of a neurodegenerative disease, it was confirmed that the formation of a protein aggregate due to the glutathionylation of a FUS protein known as an ALS-inducing protein and the deposition thereof in the cytoplasm of brain neurons cause ALS, and the activity of omega class glutathione transferase (GSTO) for inhibiting the glutathionylation of a FUS protein was confirmed. Therefore, the present disclosure was completed.

Therefore, the present disclosure provides a pharmaceutical composition for preventing or treating a neurodegenerative disease, which includes GSTO1 or omega class glutathione transferase 2 (GstO2) gene or a protein encoding the gene as an active ingredient.

The GSTO1 gene according to the present disclosure may consist of the base sequence represented by SEQ ID NO: 2 (Human GSTO1 NCBI Accession: NM_004832.2), or the amino acid sequence represented by SEQ ID NO: 3 (Human GSTO1 NCBI Accession: NP_004823.1). Here, the GSTO1 gene may include a base sequence having 70% or more, preferably 80% or more, more preferably 90% or more, and most preferably 95% or more sequence homology with the base sequence represented by SEQ ID NO: 2.

In addition, the GstO2 gene according to the present disclosure may consist of the base sequence represented by SEQ ID NO: 4 (*Drosophila* GstO2 NCBI Accession: NM_168277.2), or the amino acid sequence represented by SEQ ID NO: 5 (*Drosophila* GstO2 NCBI Accession: NP_729388.1). Here, the GstO2 gene may include a base sequence having 70% or more, preferably 80% or more, more preferably 90% or more, and most preferably 95% or more sequence homology with the base sequence represented by SEQ ID NO: 4.

The term "glutathionylation" used herein is the result of a disulfide bond between a cysteine and a reduced glutathione (GSH), which is known to bring about changes in the structure and function of a protein.

As described above in the present disclosure, it was confirmed that the formation of a protein aggregate by the glutathionylation of a FUS protein known as an ALS-inducing protein and the deposition thereof in the cytoplasm of brain neurons cause ALS. Therefore, in one embodiment of the present disclosure, as a result of culturing FUS in the presence of GSSG, it was confirmed that, as the GSH content increases, not only does the content of glutathionylated FUS increase, but also FUS is glutathionylated at Cys-447 (see Example 7), and due to the FUS glutathionylation, the formation of a FUS aggregate was specifically confirmed (see Example 8).

In another embodiment of the present disclosure, as a protein capable of regulating pathology due to glutathionylated FUS, GstO was identified, and it was confirmed that GstO2 has an effect of alleviating phenotypic defects and mitochondrial division and a functional disorder due to FUS overexpression in *Drosophila* (see Examples 9 and 10).

In still another embodiment of the present disclosure, not only the GstO2-induced effect of inhibiting the formation of a FUS aggregate in *Drosophila* neurons was confirmed, but also GstO2-induced regulation of FUS glutathionylation in *Drosophila* neurons was specifically confirmed (see Examples 11 and 12). In addition, it was confirmed that flies exhibiting an ALS phenotype due to the expression of FUS mutant $FUS^{P525L}$ also show the same effects as the GstO2-overexpressing FUS (see Example 13). Finally, the inventors confirmed the neurocytotoxicity inhibitory effect of GSTO1, which is a human homologous chromosome of GstO2 in order to confirm whether the recovery effect of GstO2 on FUS-induced neurocytotoxicity is also applied to a mammalian system, demonstrating that the effect of improving FUS insolubility and FUS-induced apoptosis is also specifically confirmed in a mammalian neuron model with ALS (see Example 14).

From these results, it can be inferred that GSTO1 or GstO2 induces FUS deglutathionylation, and exhibits an inhibitory effect on cytoplasmic FUS aggregation and neurotoxicity, indicating that GSTO1 or GstO2 can be effectively used as a therapeutic agent for a neurodegenerative disease.

The pharmaceutical composition according to the present disclosure may include a GSTO1 or GstO2 gene or a protein encoding the gene as an active ingredient, and may also include a pharmaceutically acceptable carrier. The pharmaceutically acceptable carrier is generally used in formulation, and includes saline, distilled water, Ringer's solution, buffered saline, cyclodextrin, a dextrose solution, a maltodextrin solution, glycerol, ethanol, liposomes, etc., but the present disclosure is not limited thereto. If needed, the pharmaceutically composition may further include other conventional additives including an antioxidant, a buffer, etc. In addition, by additionally adding a diluent, a dispersant, a surfactant, a binder or a lubricant, the pharmaceutical composition may be formulated as an injectable form such as an aqueous solution, an emulsion or a suspension, a pill, a capsule, a granule or a tablet. Suitable pharmaceutically acceptable carriers and their formulations may be formulated according to each ingredient using a method disclosed in the Remington's Pharmaceutical Science. The pharmaceutical composition of the present disclosure is not limited in dosage form, and thus may be formulated as an injection, an inhalant, a dermal preparation for external use, or an oral preparation.

The pharmaceutical composition of the present disclosure may be administered orally or non-orally (e.g., intravenously, subcutaneously, percutaneously, nasally or intratracheally) according to a desired method, and a dose of the pharmaceutical composition of the present disclosure may be selected according to a patient's condition and body weight, severity of a disease, a dosage form, an administration route and duration by those of ordinary skill in the art.

The pharmaceutical composition of the present disclosure is administered at a pharmaceutically effective amount. The "pharmaceutically effective amount" used herein refers to an amount sufficient for treating a disease at a reasonable benefit/risk ratio applicable for medical treatment, and an effective dosage may be determined by parameters including a type of a patient's disease, severity, drug activity, sensitivity to a drug, administration time, an administration route and an excretion rate, the duration of treatment and drugs simultaneously used, and other parameters well known in the medical field. The pharmaceutical composition of the present disclosure may be administered separately or in combination with other therapeutic agents, and may be sequentially or simultaneously administered with a conventional therapeutic agent, or administered in a single or multiple dose(s). In consideration of all of the above-mentioned parameters, it is important to achieve the maximum effect with the minimum dose without a side effect, and such a dose may be easily determined by one of ordinary skill in the art.

Specifically, the effective amount of the composition according to the present disclosure may vary according to a patient's age, sex or body weight, and generally, 0.001 to 150 mg, and preferably 0.01 to 100 mg per kg of body weight may be administered daily or every other day, or one to three times a day. However, the effective amount may be increased or decreased depending on the route of administration, the severity of obesity, sex, a body weight or age, and thus it does not limit the scope of the present disclosure in any way.

Meanwhile, as another aspect of the present disclosure, the present disclosure provides a method of preventing, regulating or treating a neurodegenerative disease, which includes administering the pharmaceutical composition to a subject.

The term "prevention" used herein refers to all actions that inhibit a neurodegenerative disease or delay the onset thereof by administration of the pharmaceutical composition according to the present disclosure.

The term "treatment" used herein refers to all actions involved in alleviating or beneficially changing symptoms of neurodegenerative disease by administration of the pharmaceutical composition according to the present disclosure.

The term "subject" used herein refers to a target in need of a prevention, regulation or treatment of a disease, and more specifically, a mammal such as a human or a non-human primate, a mouse, a rat, a dog, a cat, a horse, or a cow.

Hereinafter, to help in understanding the present disclosure, exemplary examples will be suggested. However, the following examples are merely provided to more easily understand the present disclosure, and not to limit the present disclosure.

EXAMPLES

Example 1. Experiment Preparation and Experimental Methods 1-1. Preparation of *Drosophila melanogaster*

All *Drosophila* stocks were stored under a standard food condition, a normal temperature (25° C.) and a normal humidity condition (60%), and *Drosophila* crossing was carried out according to standard procedures, and all offspring were raised at 25° C.

1-2. Cell Culture

Mouse neuroblastoma, Neuro2a cells, were cultured in DMEM (Life Technologies) containing 10% fetal bovine serum (FBS; Gibco) and a penicillin-streptomycin solution (50 mg/mL; Gibco) at 37° C. and 5% $CO_2$/95% air conditions.

1-3. In Vitro Glutathionylation Assay

The full-length protein of myc-tag human FUS (0.51 μg) purified from HEK293 (OriGene) cells was incubated in 50 mM Tris-HCl (pH 7.5) in the presence of various concentrations of an oxidized glutathione (glutathione disulfide, GSSG) at 25° C., and one hour after incubation, the sample was placed on ice, and 3×non-reducing LDS sample buffer (Invitrogen) was added. Afterward, the sample was isolated by 12% SDS-PAGE and subjected to western blotting analysis using mouse anti-GSH (1:1,000; ViroGen Corp.) and mouse anti-myc (1:1,000; Millipore) antibodies.

1-4. Transformed Flies

UAS-FUS and UAS-$FUS^{P525L}$ cell lines were obtained from Nancy M. Bonini (University of Pennsylvania), and a UAS-GstO2 cell line was obtained according to a previous document (Kim et al., 2012; Kim and Yim, 2013). In addition, UAS-GSTO1 RNAi (BL34727, v26711), UAS-GstO2 RNAi (v109255), and UAS-GstO3 RNAi (v105274) cell lines were obtained from the Bloomington *Drosophila* Stock Center and the Vienna *Drosophila* RNAi Center, a UAS-mitoGFP cell line was obtained from H. J. Bellen (Baylor College of Medicine), and a pan-neuronal driver, elav-Gal4, muscle-specific driver, mhc-Gal4, motoneuron-specific driver and D42-Gal4 cell lines were also obtained from the Bloomington *Drosophila* Stock Center and the Vienna *Drosophila* RNAi Center. Here, W1118 flies were used as a control according to a genetic background.

1-5. Transfection

N2a cells were plated in a 6-well plate, and transfected with 4 μg of pCMV6-FUS-green fluorescent protein (GFP)-labeled human wild-type FUS or pCMV6-$FUS^{P525L}$-GFP-labeled mutant $FUS^{P525L}$ using a Lipofectamine 3000 reagent (Invitrogen) according to the manufacturer's manual. Here, an empty pCMV6-AC-GFP plasmid was used as a negative control.

1-6. Generation of Stable Cell Line

N2a cells in a 24-well plate were transfected with 1 μg of human GSTO1 cDNA using a Lipofectamine 3000 reagent (Invitrogen), and for 2 days after transfection, stable transformants were selected in the presence of G418 (600 μg/mL). Here, the overexpression of a GSTO1 protein in the stable transformant was confirmed through an immunoblotting assay.

1-7. Total Brain Immunostaining

The adult brain of a 7-day-old adult male fly was fixed with 4% formaldehyde in a fixation buffer (100 mM PIPES, 1 mM EGTA, 1% Triton X-100, 2 mM $MgSO_4$, pH 6.9), blocked with a washing buffer (50 mM Tris-HCl, 150 mM NaCl, 0.1% Triton X-100 and 0.5 mg/mL BSA, pH 6.8) containing 10 mg/mL BSA, and then incubated with primary antibodies diluted with a blocking buffer at 4° C. for 12 hours, and here, the used antibodies are as follows:

Rabbit anti-FUS (1:100, Bethyl Laboratories), mouse anti-FUS (1:50, Santa Cruz Biotechnology), rabbit anti-GstO2 (1:20), and mouse anti-GSH.

Afterward, the sample was incubated with an Alexa 488-conjugated secondary antibody (1:200, Invitrogen), a Cy3-conjugated secondary antibody (1:200, Jackson Immuno Research Laboratories) and DAPI (1:500, Sigma-Aldrich), and the brain was washed three times for 10 minutes with a washing buffer, and fixed with a SlowFade™ Gold antifade reagent (Invitrogen). Here, all images were obtained using a Carl Zeiss confocal microscope LSM710).

1-8. Immunohistochemistry

Cells were fixed with 4% paraformaldehyde in phosphate-buffered saline (PBS) for 30 minutes, and washed three times for 10 minutes with PBS containing 0.3% Triton X-100 (PBST). Afterward, the cells were incubated for 1 hour at 25° C. with a blocking buffer (PBST containing 5% normal goat serum (NGS)) and primary antibodies diluted with a blocking buffer at 4° C. for 12 hours. Here, the used antibodies are as follows:

Mouse anti-GSH (1:100; ViroGen Corp.), rabbit anti-FUS (1:100; Bethyl Laboratories), mouse anti-GFP (1:200; Roche) and rabbit anti-cleavedcaspase-3 (1:500, Cell Signaling).

After incubation with primary antibodies, the cells were washed three times for 10 minutes with PBST, and incubated with secondary antibodies diluted in PBST at 1:2000 at 25° C. for 1 hour. Here, the used secondary antibodies are as follows:

Alexa-594-conjugated goat anti-rabbit IgG, Alexa-488-conjugated goat anti-rabbit IgG, Alexa 594-conjugated goat anti-mouse IgM and Alexa-488-conjugated goat anti-mouse IgG (Jackson Immuno Research Laboratories).

Afterward, the samples were observed using a Leica confocal microscope.

Afterward, for analysis of a neuromuscular junction (NMJ) in *Drosophila,* 3rd instar larvae were dissected, and fixed with 4% formaldehyde in PBS for 15 minutes. Subsequently, the samples were washed with 0.1% Triton X-100-containing PBS three times for 10 minutes, blocked with 5% BSA in PBST, and incubated with primary antibodies at 4° C. for 12 hours. Here, FITC-conjugated anti-HRP (Jackson Immuno Research Laboratories) was used at 1:150, and fixed by treating SlowFade™ Gold antifade reagent (Invitrogen), and all images were obtained using a Leica TCS SP5 AOBS confocal microscope.

1-9. Homology Modeling

The 3D structure of the FUS ZnF domain (32 amino acid residues, 422-RAGDWKCPNPTCENMNFSWR-NECNQCKAPKPD-453) was predicted and created in order to predict the structure and function of a protein using I-TASSER server based on Molegro Molecular Viewer 2.5.0 (Molegro ApS, Aarhus C, Denmark).

1-10. In Vitro Protein Aggregation Assay

After in vitro glutathionylation, a sample was subjected to heat-block at 37° C., centrifuged at 4° C. for 30 minutes under a condition of 20,000×g, thereby being divided into supernatant and pellet fractions. The pellet was washed with 50 mM Tris-HCl (pH 7.5) five times for 10 minutes, and lysed with a reducing agent in an LDS sample buffer (2% SDS; Invitrogen). In both fractions, FUS was detected with rabbit anti-FUS (1:1000; Bethyl Laboratories) antibodies by western blotting analysis.

1-11. External Eye Microscopy

An eye image of adult *Drosophila* was taken with a digital camera by fixing the head on a slide glass. Here, 5-day-old male Drosophilae were used for an experiment. Meanwhile, the image was taken using a Leica MZ10 F stereomicroscope and a Leica DFC450 camera system.

1-12. Locomotive Activity and Lifespan Assays

For larval crawling assay, to remove food waste remaining on 3rd instar larvae, the larvae were washed with PBS, dried on a clean filter, and placed on a 2% grape juice-agar petri dish to allow the larvae to crawl for 90 seconds. Here, to quantify larval crawling behavior, the larvae were tracked and distance was measured using Image J software, and the results for at least 10 larvae were averaged for each transgenic line.

Afterward, for a climbing assay, ten male Drosophilae in each age group were anesthetized with carbon dioxide, put into column vials, and then transferred to empty vials to be incubated at room temperature for 1 hour and acclimated to the environment, and the number of Drosophilae climbing up to the top of the vial within 10 seconds was counted. Here, the experiment was independently repeated four times for each transgenic line every five minutes, and all of the climbing experiments were performed at 25° C.

Finally, for a lifespan assay, twenty male Drosophilae of each genotype (>150 Drosophilae) were put into respective vials and maintained at 25° C., and then all groups were transferred into new vials, followed by counting the number of dead Drosophilae.

1-13. Immunoblot Analysis

A protein extract for western blotting analysis was prepared by homogenizing heads of ten 14-day-old male Drosophilae in an LDS sample buffer (Invitrogen), and the total protein extract was isolated using a 4% to 12% gradient SDS-PAGE gel and transferred to a PVDF membrane (Millipore), and the membrane was blocked with Tris-buffered saline containing 4% skim milk or 4% bovine serum albumin (BSA) for 1 hour, and incubated with primary antibodies at 4° C. for 12 hours.

Here, the primary antibodies used herein are as follows: Rabbit anti-FUS (1:1000, Bethyl Laboratories), rabbit anti-*Drosophila* Marf (1:1000, Leo Pallanck, a gift from the University of Washington, Seattle, WA), mouse anti-Opal (1:1000; mouse anti-UQCRC2 (1:1000, Abcam), mouse anti-ATP5A (1:10000, Abcam), mouse anti-*Drosophila* GstO2 (1:1000), rabbit anti-lamin C (Developmental Studies Hybrodoma Bank, DSHB), rabbit anti-α-tubulin (1:2000, Sigma), and rabbit anti β-actin (1:4000, Cell Signaling).

Blots were washed in TBS containing 0.1% Tween-20 (TBST) and incubated with secondary antibodies, and primary antibodies were detected with HRP-conjugated secondary antibodies using a goat anti-rabbit IgG HRP conjugate and a goat anti-mouse IgG HRP conjugate (1:2000, Millipore). Here, detection was carried out suing an ECL-Plus kit (Amersham).

Subsequently, the protein extract was homogenized in an RIPA buffer (Cell Signaling) containing a protease-phosphatase inhibitor cocktail (Roche), and mixed with a LDS sample buffer (Invitrogen) in combination with a reducing agent. Afterward, a protein sample was separated with a 4% to 12% Bis-Tris gel (Novex), transferred to a PVDF membrane (Novex), and subjected to western blotting analysis using rabbit anti-TurboGFP (1:2000, OriGene), mouse anti-GSTO1 (1:1000, Proteintech), rabbit anti-DDK (1:1000, OriGene) and rabbit anti-α-tubulin (1:2000, Sigma) primary antibodies.

1-14. Image and Morphology of Mitochondria

To confirm the image of mitochondria in muscle tissue of the chest, 7-day-old adult male Drosophilae were dissected in PBS, fixed with 3% formaldehyde in a fixation buffer (100 mM PIPES, 1 mM EGTA, 1% Triton X-100 and 2 mM $MgSO_4$, pH 6.9) for 25 minutes, and washed with a washing buffer (50 mM Tris-HCl, 150 mM NaCl, 0.1% Triton X-100 and 0.5 mg/mL BSA, pH 6.8). Afterward, the resulting sample was fixed with a SlowFade™ Gold antifade reagent (Invitrogen), and photographed using a CarlZeiss confocal microscope (LSM710).

Afterward, to confirm the image of mitochondria in the motoneurons of a limb, 7-day-old adult male Drosophilae were dissected in PBS, and a front limb was fixed with 4% formaldehyde in a fixation buffer (100 mM PIPES, 1 mM EGTA, 1% Triton X-100 and 2 mM $MgSO_4$, pH 6.9) for 25 minutes, washed with PBST, fixed with a SlowFade™ Gold antifade reagent (Invitrogen), followed by acquiring an image using a CarlZeiss confocal microscope (LSM710).

1-15. Blue Native Polyacrylamide Gel Electrophoresis (BN-PAGE)

Mitochondria were isolated from 14-day-old male adult Drosophilae using a mitochondrial isolation kit (Pierce) according to the manufacturer's protocols, and the purified mitochondria extract was resuspended in 60 μL of 1×Native PAGE sample buffer (Invitrogen) containing 2% n-dodecyl-β-D-maltoside (DDM), 1% Digitonin and a protease inhibitor (Halt). Subsequently, the sample was incubated on ice for 15 minutes and centrifuged at 12,000×g. A mitochondrial protein concentration in a supernatant was detected, and the supernatant (20 μg) was mixed with a 0.5% G-250 sample additive, followed by BN-PAGE using a 3% to 12% Native PAGE Bis-Tris gel (Invitrogen) at 4° C. Here, an anode running buffer was used for the outside of a gel, and a cathode running buffer was used for the inside of a gel. After PAGE, western blotting analysis was carried out with mouse anti-NDUFS3 (1:5000, Abcam), mouse anti-UQCRC2 (1:1000, Abcam), and mouse anti-ATP5A (1:10000, Abcam) antibodies.

1-16. Measurement of Mitochondrial Superoxide

Mitochondrial ROS generation in *Drosophila* was detected using a mitochondrial oxygen free radical indicator, mitoSOX-Red (Invitrogen), according to the manufacturer's protocol. More specifically, muscle tissue cut from the chest of 11-day-old *Drosophila* in cold PBS was incubated with 5 μM MitoSOX-Red in DMSO at 25° C. for 20 minutes, washed with cold PBS three times, the muscle tissue sample was rapidly fixed with a SlowFade™ Gold antifade reagent (Invitrogen), and then observed using a Carl Zeiss confocal microscope (LSM710) within 15 minutes. Here, fluorescence intensity was quantified using Image J software.

1-17. ATP assay

To inhibit ATPase enzyme activity, the chests of 28-day-old Drosophilae were homogenized in 100 μL of an extraction buffer (6M Guanidine-HCl, 100 mM Tris, 4 mM EDTA, pH 7.8), an extract was immediately lyophilized in liquid nitrogen, and heated to denature an ATP synthase. Afterward, the sample was centrifuged at 20,000×g for 15 minutes, a supernatant was transferred to a new tube and diluted with an extraction buffer (1/100), the sample was added to each well of a 96-well plate and mixed with a luminescent solution of an Enliten ATP assay kit (Promega), and luminescence was measured using a Glomax microplate reader (Promega) every ten seconds. Afterward, a supernatant was diluted with an extraction buffer (1/2), and a protein concentration was measured using a BCA protein assay kit (Pierce). Afterward, the measured concentration was divided by the total protein concentration, thereby measuring a relative ATP level compared to the standard.

1-18. Protein Oxidation Assay

Protein oxidation detection was detected using an OxyBlot protein oxidation detection kit (Millipore) according to the manufacture's protocols. Specifically, the chests of 28-day-old Drosophilae were homogenized in a lysis buffer containing 6% SDS-containing 2% β-mercaptoethanol, the homogenate was centrifuged at 20,000×g for 30 minutes, followed by discarding pellet debris, and a denatured protein was derivatized with 2, 4-dinitrophenylhydrazine (DNPH) at 25° C. and neutralized with a neutralization solution. The DNPH-labeled protein was then subjected to SDS-PAGE, and transferred to a PVDF membrane (Millipore), and then the membrane was analyzed with an anti-DNP antibody (1:150, Millipore), a signal was detected using a goat anti-rabbit IgG HRP-conjugated secondary antibody (1:300; Millipore). Here, detection was carried out using an ECL-Plus kit (Amersham), and a band density was measured using the Image J software.

1-19. Nuclear/Cytoplasmic Fractionation Assay

Twenty heads of male Drosophilae were lysed in a nuclear extract kit reagent (Active Motif) according to the manufacturer's protocols, and protein extracts obtained from different cell fractions were mixed with a SDS loading buffer and heated, followed by western blotting analysis through SDS-PAGE.

1-20. Protein Solubility Assay

Total proteins were fractionated according to solubility using several modified protocols previously disclosed (Woo et al., 2017), and 20 heads of 7 to 14-day-old Drosophilae were homogenized in a lysis buffer without SDS (50 mM Tris-HCl, 150 mM NaCl, 5 mM EDTA, 0.1% NP-40, and 10% glycerol, pH 7.5). Subsequently, the homogenized sample was centrifuged at 100,000×g and 4° C. for 30 minutes, and a supernatant, as a soluble fraction, was obtained. In addition, the remaining pellet was additionally extracted with 50 μL of a 2×buffer containing 2% SDS and sonicated, followed by heating at 95° C. for 10 minutes. In this process, a supernatant was obtained into insoluble fractions.

1-21. GSH/GSSG Contents

The oxidized form (glutathione sulfide, GSSG) and reduced form of glutathione (GSH) were quantified using a glutathione assay kit (Cayman Chemical) according to the manufacturer's protocols, and more specifically, the total glutathione from 10 heads of 10-day-old Drosophilae was homogenized in 50 μL of 50 mM MES buffer, the sample was centrifuged at 10,000×g for 15 minutes, and a supernatant was transferred to a new tube. Afterward, the same amount of MPA reagent was added to the sample, and then the mixture was maintained at room temperature for 5 minutes. The mixture was centrifuged at 2,000×g for 2 minutes, and then vortexed as soon as 2.5 μL of TEAM reagent was added. Subsequently, the resultant was put into each well of a 96-well plate, and an MES buffer, a cofactor mixture, an enzyme mixture and a DTNB mixture were added. Afterward, 405 nm absorbance was measured using a Glomax microplate reader (Promega), 2.5 μL of TEAM reagent was added, an oxidized glutathione (GSSG) was measured using the same method as the total glutathione assay. In addition, 2-vinylpyridine was added, followed by incubation at 25° C. for 1 hour, and a supernatant was diluted in an extraction buffer (1/10) and then a protein concentration was measured using a BCA protein assay kit (Pierce) through the same method as the total glutathione assay. To obtain values obtained by calculating levels of the oxidized glutathione (GSSG) and the reduced glutathione (GSH), compared to the standard level, the obtained protein concentration was divided by a total protein concentration.

Example 2. Confirmation of In Vitro Glutathionylation of FUS Protein

In this example, to confirm whether in vitro glutathionylation of a FUS protein occurs, the oxidized glutathione (glutathione disulfide, GSSH) was added to a myc-labeled human FUS recombinant full-length protein and incubated, separation through sodium dodecyl sulfate-polyacrylamide gel electrophoresis (SDS-PAGE) was performed, and western blotting analysis was performed using a mouse anti-GSH antibody and a mouse anti-myc antibody.

Figure 1B:
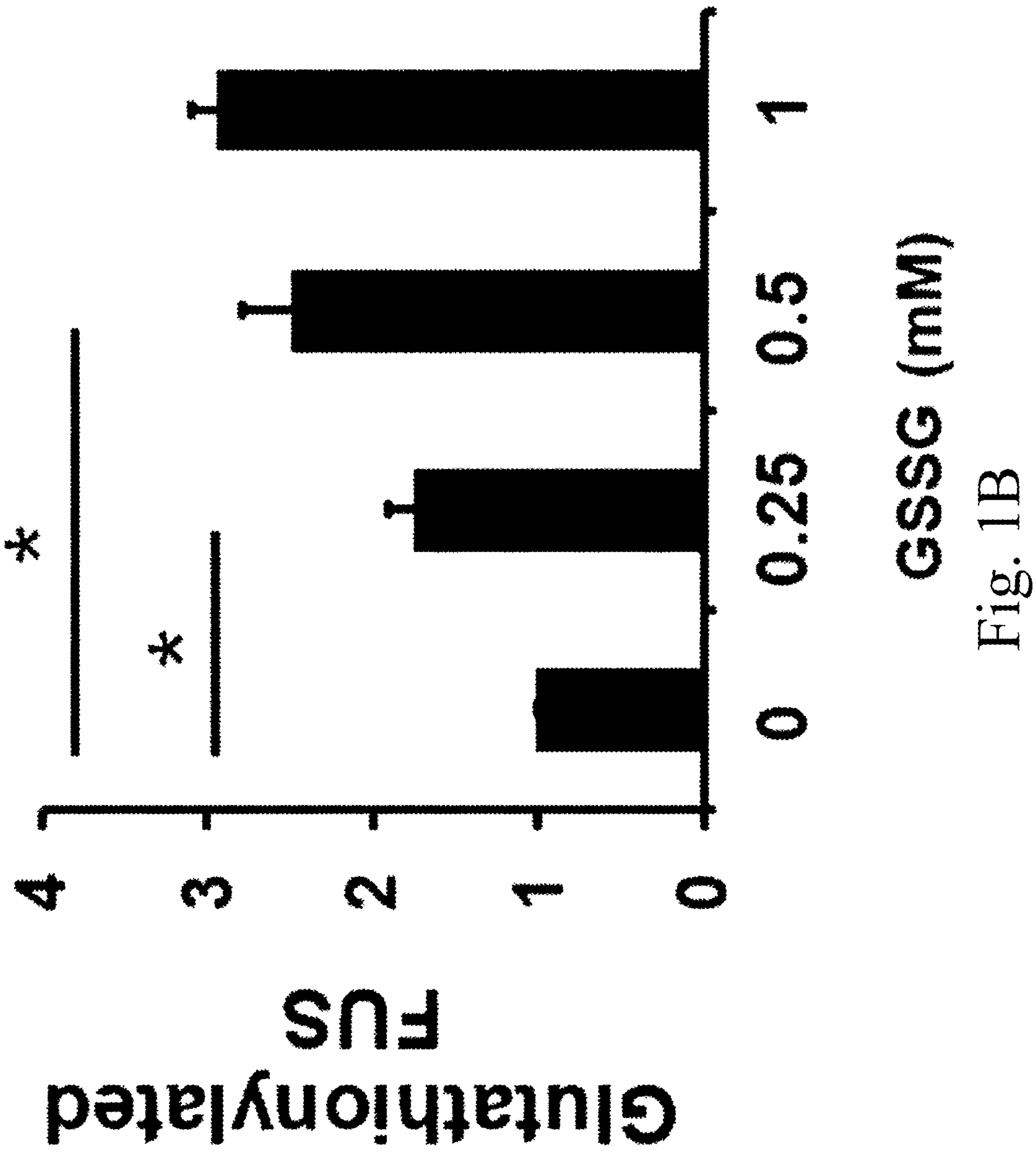
FIG. 1B shows the result of quantitative analysis of the isolated protein based on the concentration of an oxidized glutathione (GSSG) to quantitatively analyzed the glutathionylation of a human FUS protein.

As a result, as shown in FIGS. 1A and 1B, as the concentration of the oxidized glutathione (Glutathione disulfide, GSSH) increases (0 mM, 0.25 mM, 0.05 mM and 1 mM), it was confirmed that a larger amount of a glutathionylated FUS protein is detected. From the result, it was confirmed that the glutathionylation of a FUS protein occurs in vitro depending on the concentration of the oxidized glutathione (glutathione disulfide, GSSH).

Example 3. Confirmation of In Vivo Glutathionylation of FUS Protein

To confirm whether the glutathionylation of FUS protein occurs in vivo, a human FUS protein specifically expressed in neurons was expressed in *Drosophila* neurons using an elav-Gal4 driver. Specifically, a pCMV6-FUS-GFP-labeled human wild-type FUS protein was transfected into *Drosophila*. A region stained with DAPI represents the location of the nucleus.

Figure 2A:
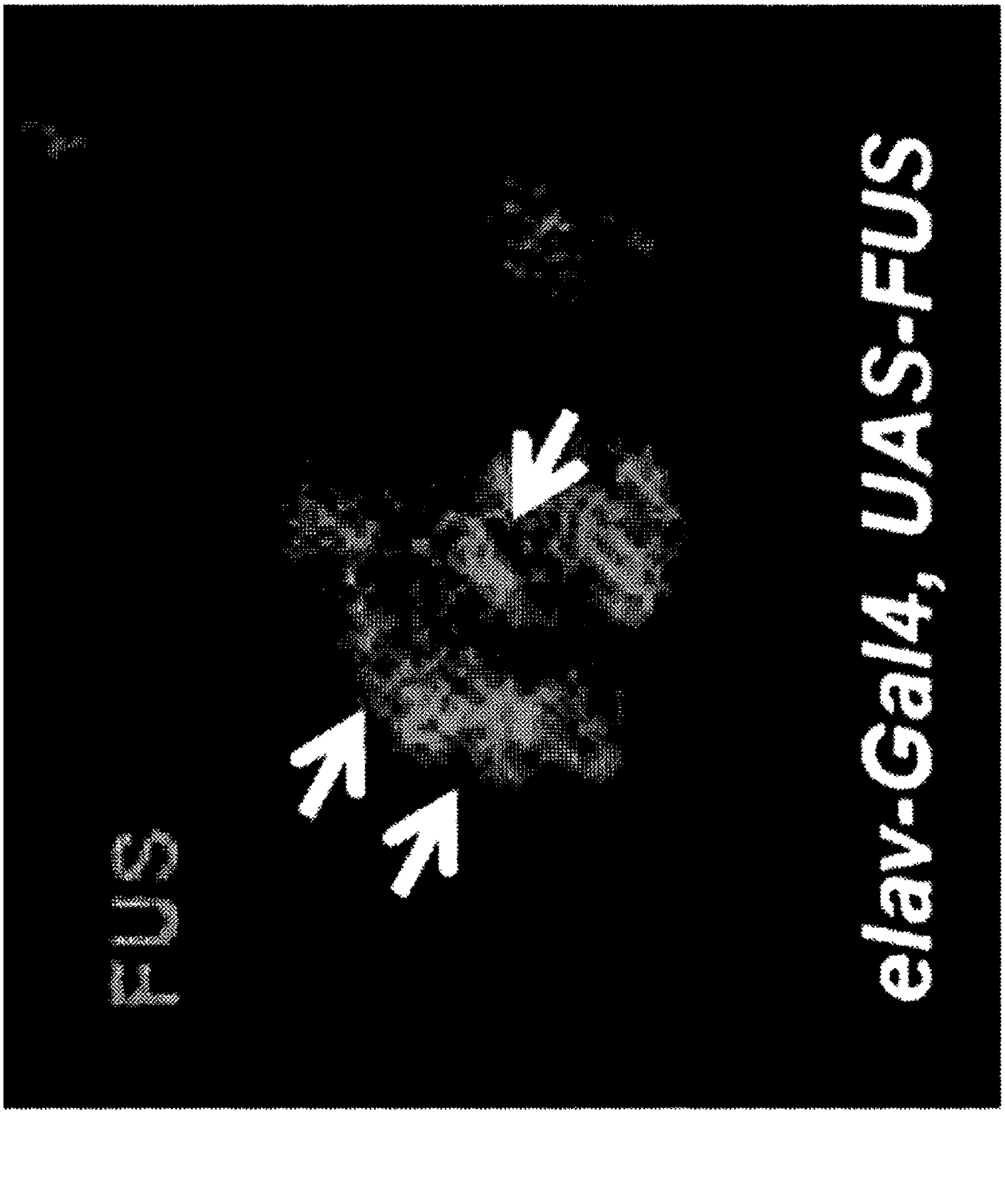
FIG. 2A is an image showing that an overexpressed human FUS protein aggregate is located in the cytoplasm of *Drosophila* brain neurons to confirm the intracellular location of the human FUS protein.
Figure 2B:
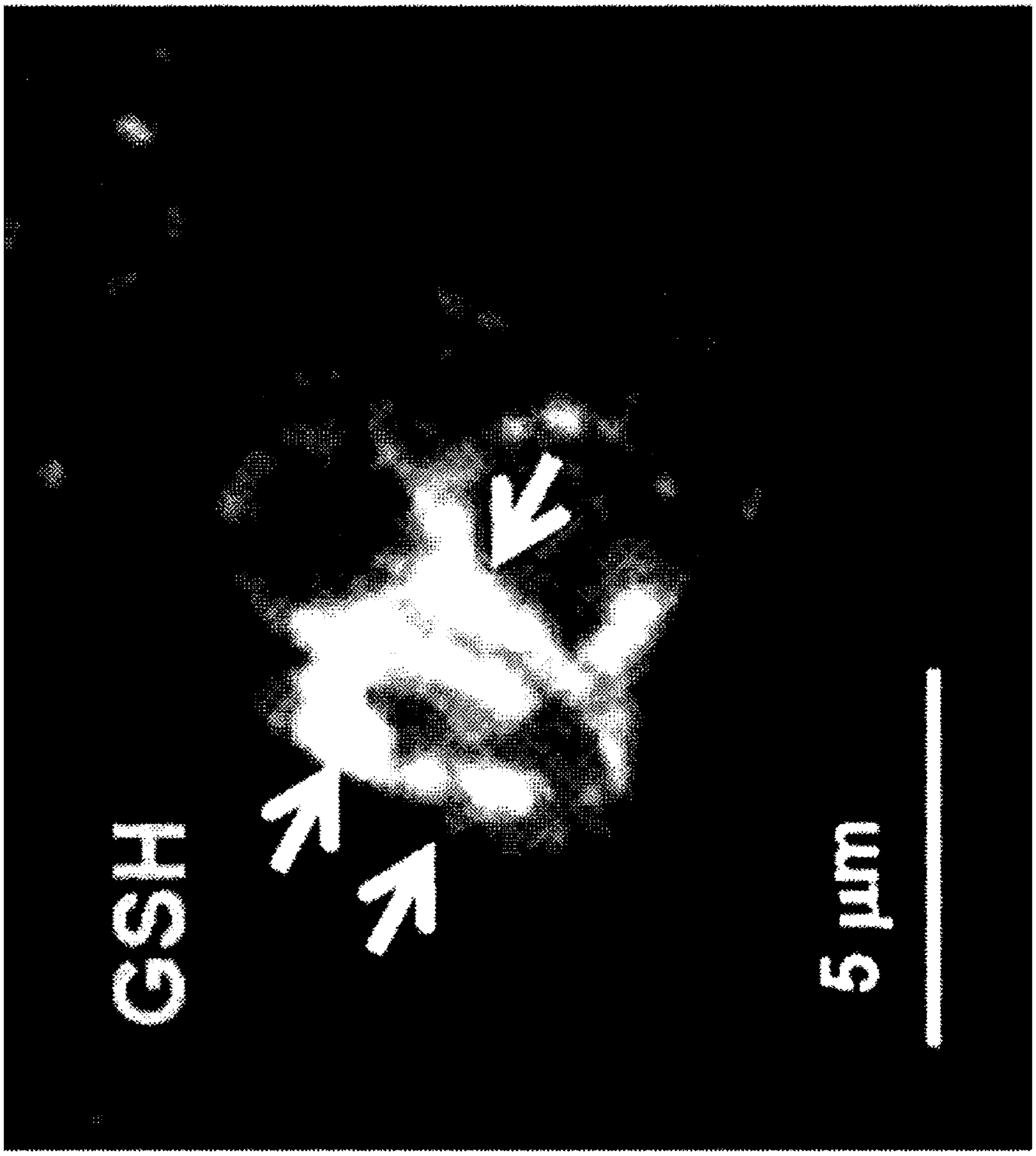
FIG. 2B is an image showing that a reduced glutathione (GSH) generated by glutathionylation of a FUS protein is located in the cytoplasm of *Drosophila* brain neurons.
Figure 2C:
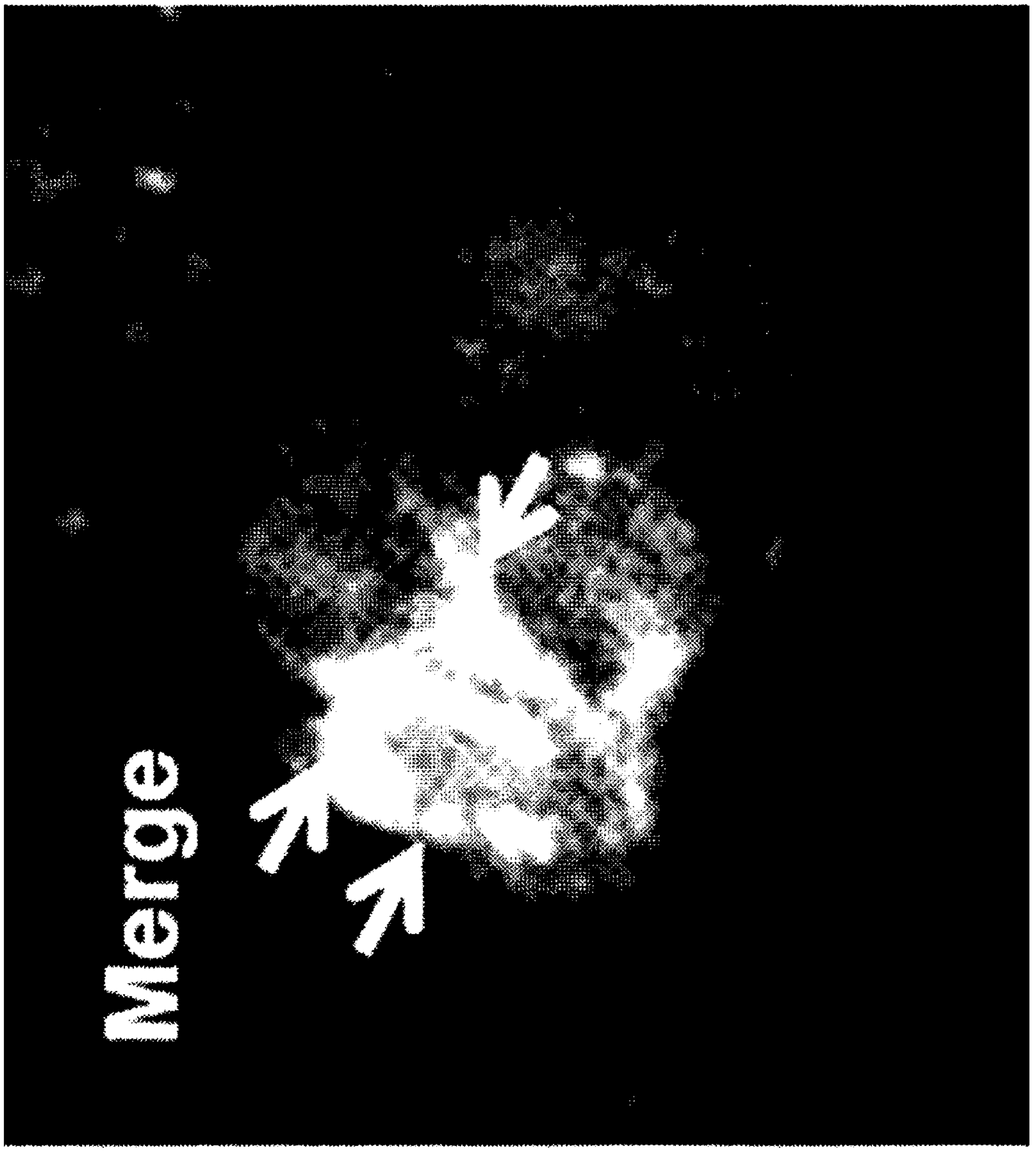
FIG. 2C is an image showing that a human FUS protein aggregate and a reduced glutathione (GSH) are located in the cytoplasm of *Drosophila* brain neurons to confirm the intracellular locations of the human FUS protein aggregate and the reduced glutathione (GSH).

As a result, the human wild-type FUS protein is located mainly in the nucleus of neurons of the brain of *Drosophila*, but as indicated by the arrows of FIG. 2A, when the human wild-type FUS protein is overexpressed, it was confirmed that a large amount of human wild-type FUS protein aggregates are observed in the cytoplasm (green). In addition, as indicated by the arrows of FIG. 2B, it was confirmed that the reduced glutathione (GSH) is observed in the cytoplasm (red). In addition, as indicated by the arrows of FIG. 2C in which FIGS. 2A and 2B are combined, it was confirmed that the FUS protein aggregate in the neuron cytoplasm of the brain is observed at the same location as the reduced glutathione (GSH). The above result means that both of a human wild-type FUS protein glutathionylated by the oxidized glutathione (glutathione disulfide, GSSH) and the reduced glutathione (GSH) generated by glutathionylation are present in the cytoplasm in vivo.

Example 4. In vitro glutathionylation of FUS protein in mammalian system

In this example, to confirm whether the glutathionylation of a human wild-type FUS protein and a human mutant $FUS^{P525L}$ protein occurs in a mammalian system, a human wild-type FUS protein and a human mutant $FUS^{P525L}$ protein were expressed (transfected) in a mouse neuroblastoma cell line Neuron2a (N2a). The region stained with DAPI represents the location of the nucleus.

Figure 3A:
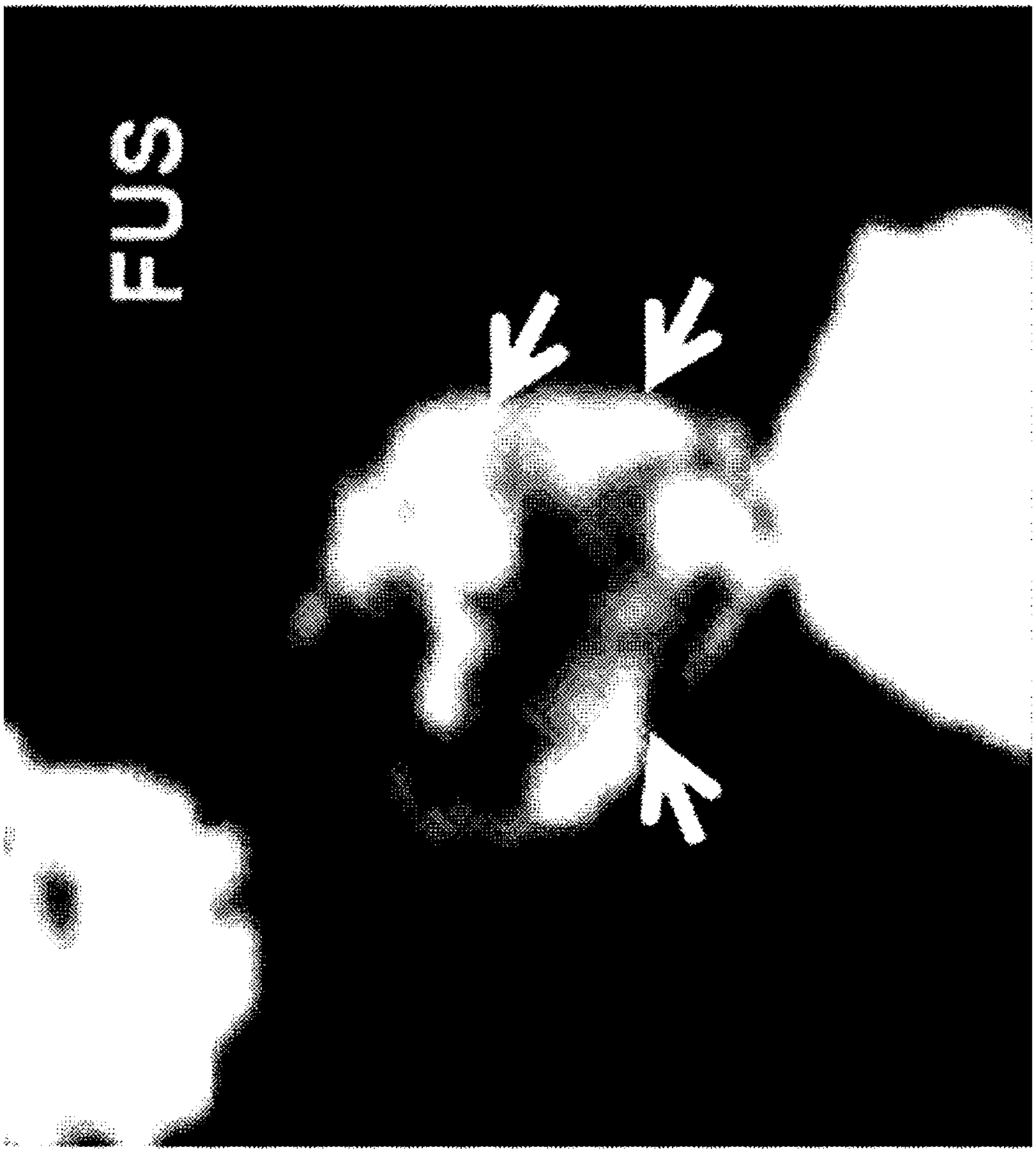
FIG. 3A is an image showing that a human wild-type FUS protein aggregate is located in the cytoplasm of N2a to confirm the intracellular location of the human wild-type FUS protein aggregate.
Figure 3B:
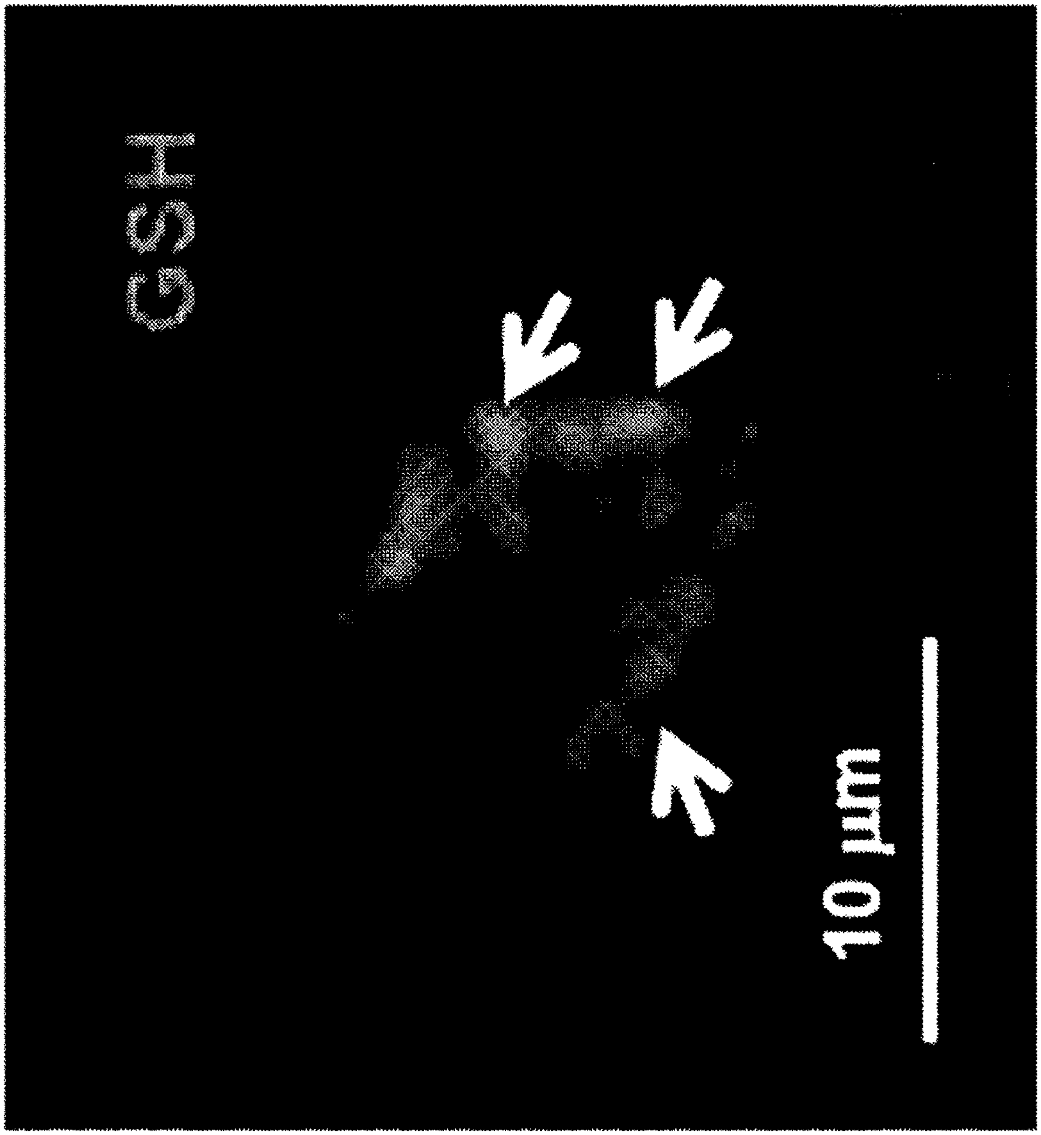
Figure 3C:
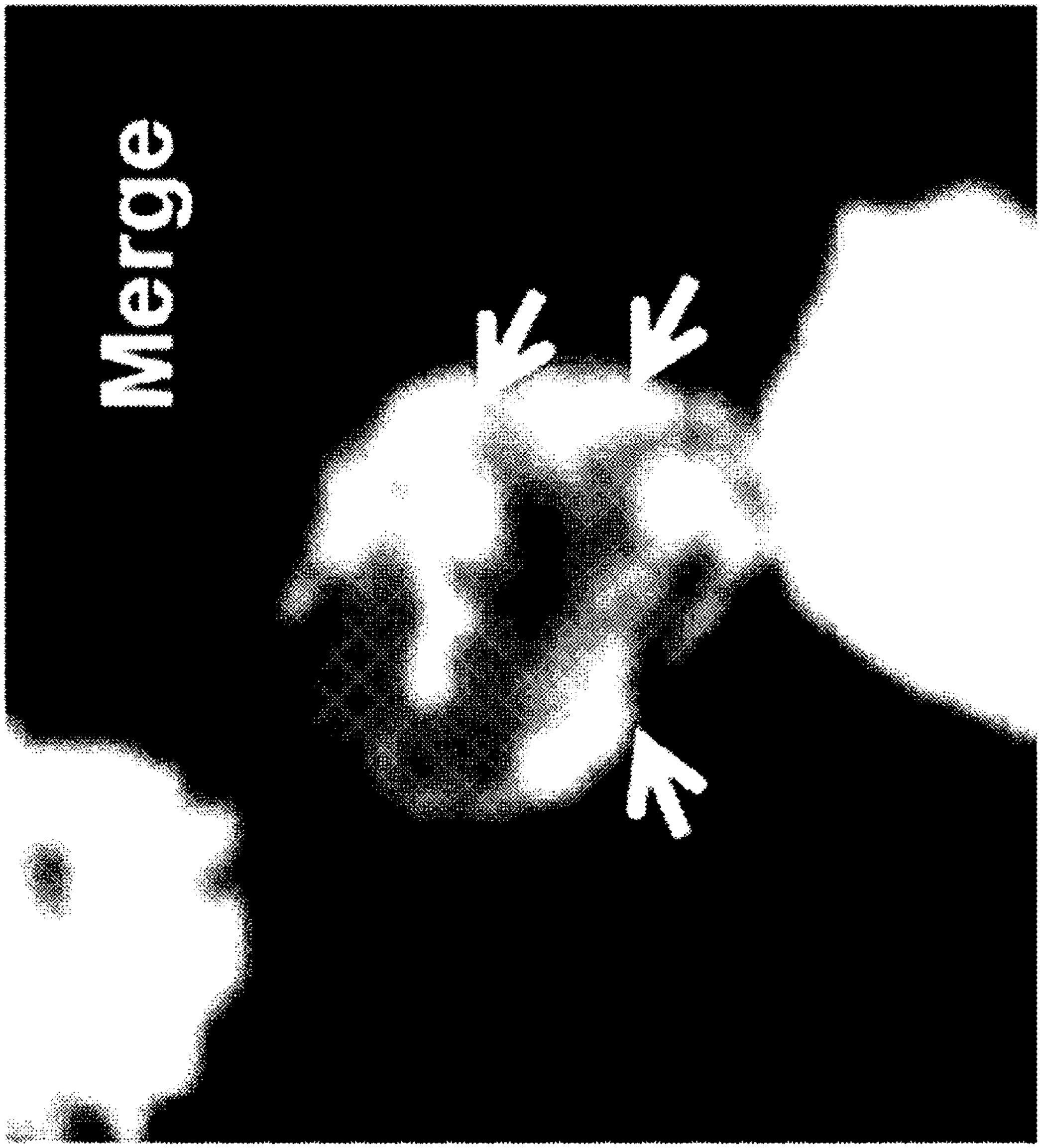
FIG. 3C is an image showing that a human wild-type FUS protein aggregate and a reduced glutathione (GSH) are located in the cytoplasm of N2a to confirm the intracellular locations of the human wild-type FUS protein aggregate and the reduced glutathione (GSH).
Figure 4A:
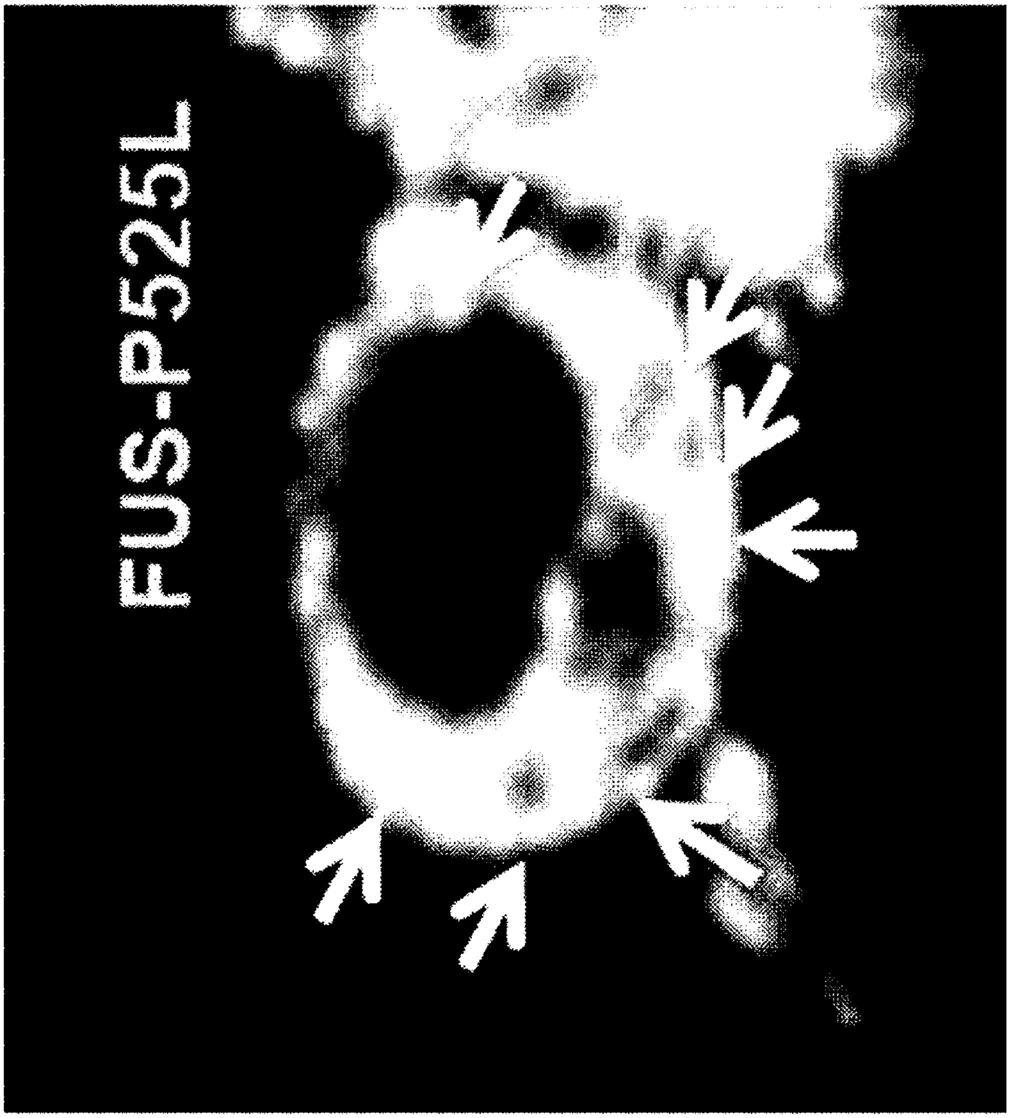
FIG. 4A is an image showing that a human mutant $FUS^{P525L}$ protein aggregate is located in the cytoplasm of N2a to confirm the intracellular location of the human mutant $FUS^{P525L}$ protein aggregate.
Figure 4B:
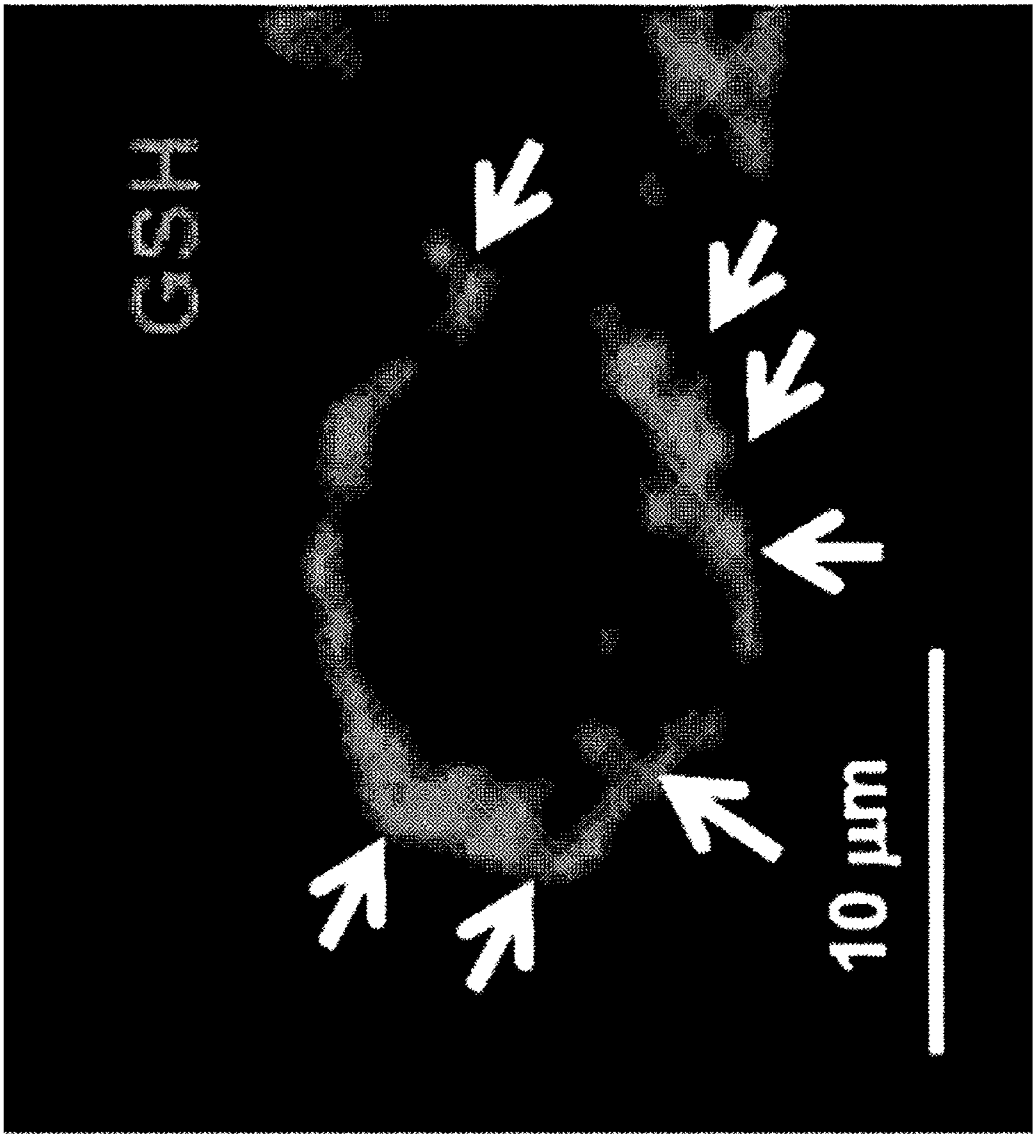
Figure 4C:
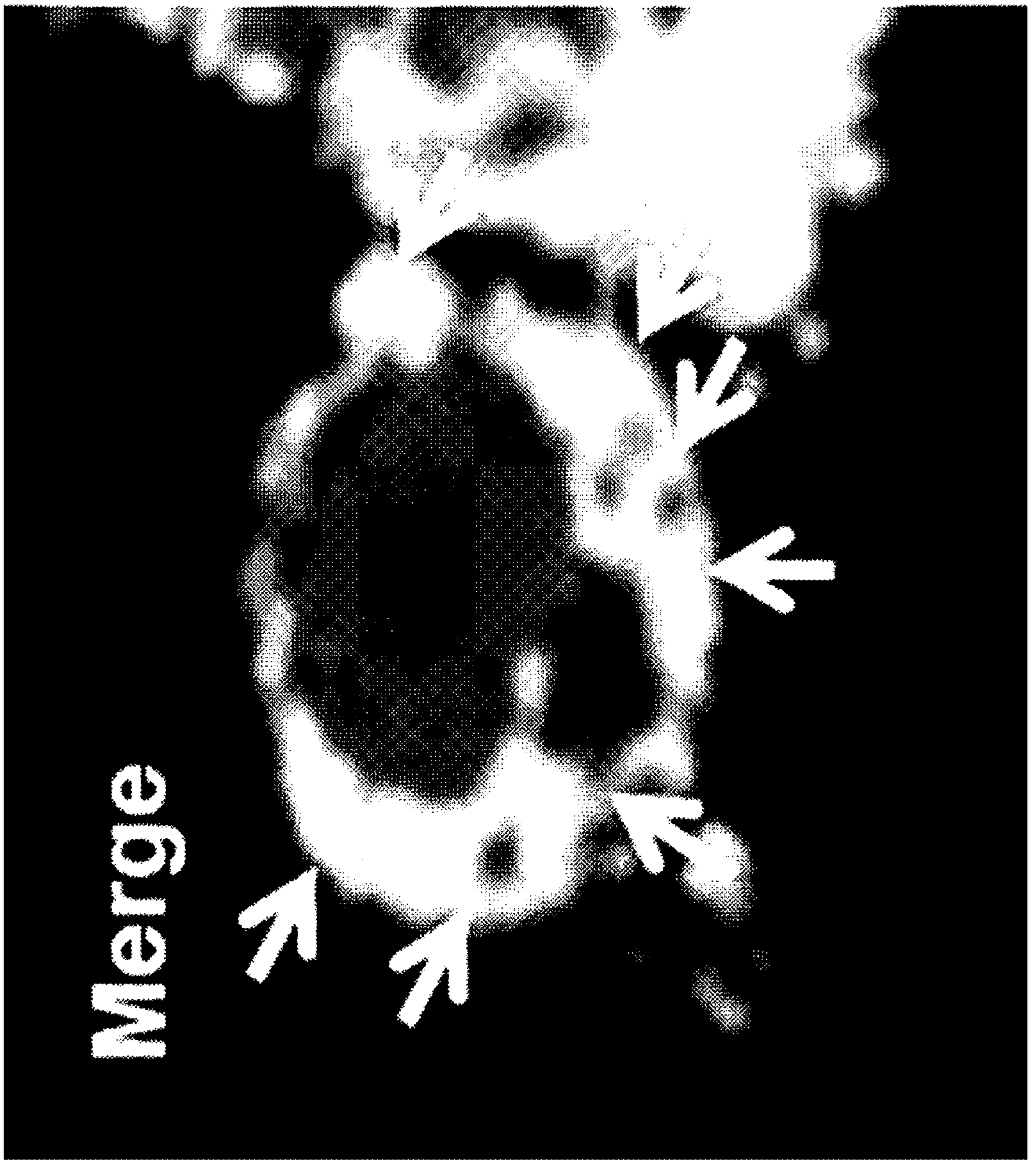
FIG. 4C is an image showing that a human mutant $FUS^{P525L}$ protein aggregate and a reduced glutathione (GSH) are located in the cytoplasm of N2a to confirm the intracellular locations of the human mutant $FUS^{P525L}$ protein aggregate and the reduced glutathione (GSH).

Asa result, as indicated by the arrows of FIG. 3A, it was confirmed that a large amount of human wild-type FUS protein aggregates are observed in the cytoplasm (green). In addition, as indicated by the arrows of FIG. 3B, it was confirmed that the reduced glutathione (GSH) is observed in the cytoplasm (red). As indicated by the arrows of FIG. 3C in which FIGS. 3A and 3B are combined, it was confirmed that a positive signal of the reduced glutathione (GSH) is mainly detected in the cytoplasm in which the human wild-type FUS protein aggregates are present. In addition, as indicated by the arrows of FIG. 4A, it was confirmed that a large amount of the human mutant $FUS^{P525L}$ protein aggregates are observed in the cytoplasm (green). In addition, as indicated by the arrows of FIG. 4B, it was confirmed that the reduced glutathione (GSH) is observed in the cytoplasm (red). As indicated by the arrows of FIG. 4C in which FIGS. 4A and 4B are combined, it was confirmed that a positive signal of the reduced glutathione (GSH) is mainly detected in the cytoplasm in which the human mutant $FUS^{P525L}$ aggregates are present. From the above results, it was confirmed that the glutathionylation of a human FUS protein in the *Drosophila* body also occurs in a mammalian system.

Example 5. Confirmation of Location at which Glutathionylation of FUS Protein Occurs 5-1. Confirmation of Location at which Glutathionylation of FUS Protein by Mass Spectrometry In this example, to confirm a location at which glutathionylation in a human FUS protein occurs, in vitro glutathionylation of a myc-labeled human FUS protein was induced, and the glutathionylated human FUS protein was detected using a Coomassie stained gel. Afterward, a human FUS protein band was cut from the gel and digested with trypsin, followed by performing Matrix Assisted Laser Desorption/Ionization (MALDI)-mass spectrometry.

Figure 5:
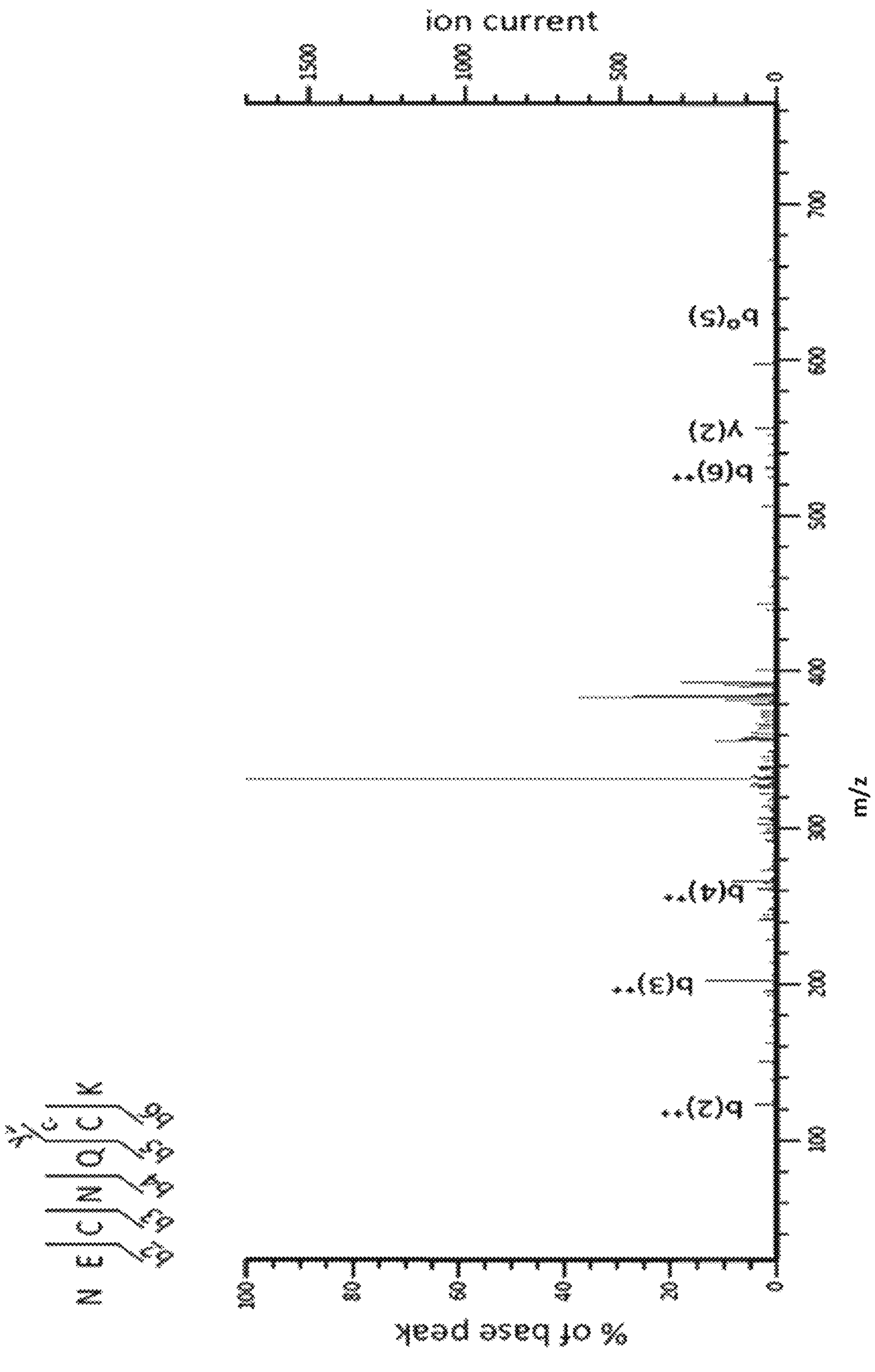
FIG. 5 shows the result of MALDI-mass spectrometry to confirm a specific location of the glutathionylation of a FUS protein.
Figure 6:
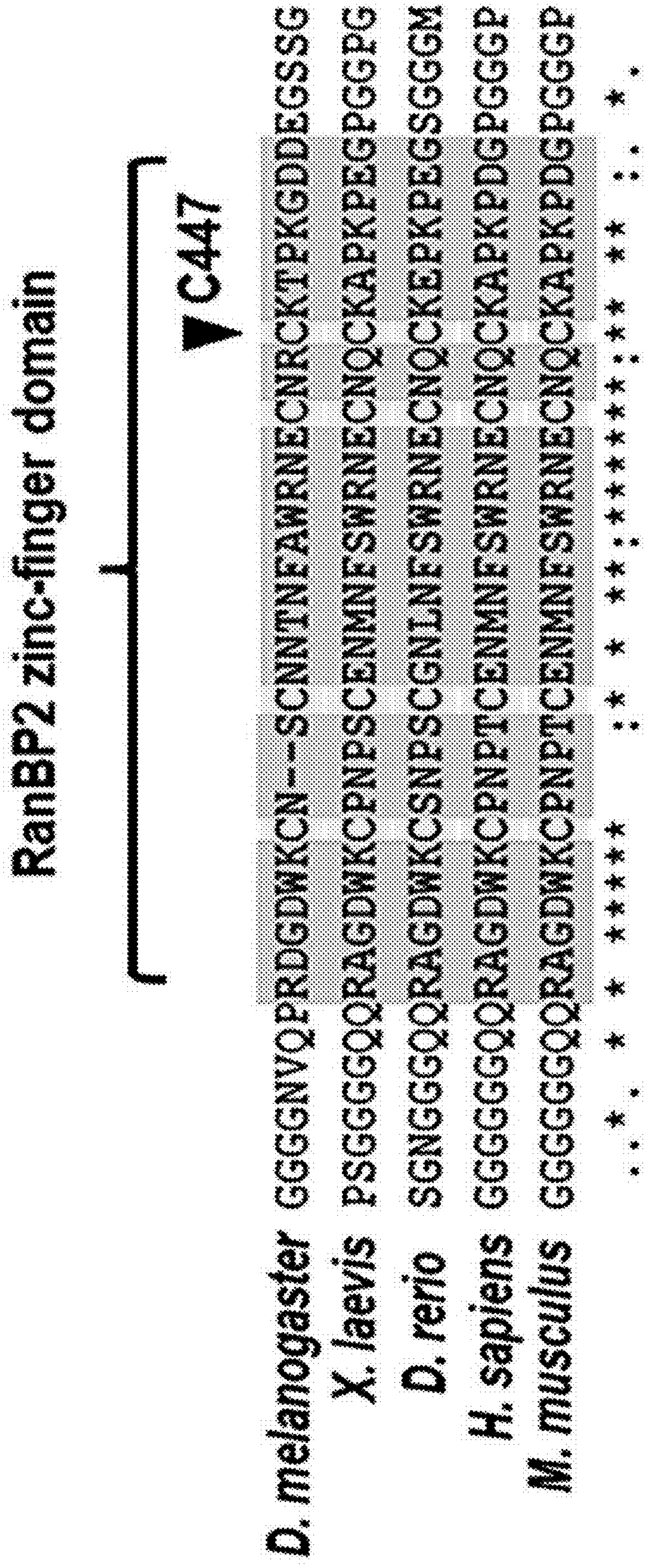
FIG. 6 shows the result of analyzing RanBP2 zinc-finger domains of *D. melanogaster, X. laevis, D. rerio, M. musculus*, and a human (*H. sapiens*) to confirm whether the cysteine sequence of the RanBP2 zinc-finger domain in the FUS protein is conserved between species.

As a result, as shown in FIG. 5, amino acid peptides having a mass difference of 305 Da were detected by mass spectrometry. This is a mass corresponding to one reduced glutathione (GSH moiety), and when the MALDI-mass spectrometry graphs in FIG. 5 are summarized, as indicated by the arrows of FIG. 6, it was confirmed that the glutathionylation of a human FUS protein occurs at the Cys-447 site of the RanBP2 zinc-finger domain.

5-2. Confirmation Whether of Sequence of RanBP2 Zinc-Finger Domain in FUS Protein is Conserved Between Species s The RanBP2 zinc-finger domain of a FUS protein includes four cysteines. To confirm whether the cysteine sequence among the sequence of the RanBP2 zinc-finger domain is conserved in eukaryotes, the sequences of the RanBP2 zinc-finger domains of *D. melanogaster, X. laevis*, a zebrafish (*D. rerio*), a mouse (*M. musculus*) and a human (*H. sapiens*) were analyzed.

As a result, as shown in FIG. 12, it was confirmed that all of the four cysteines of the RanBP2 zinc-finger domain are conserved in *D. melanogaster, X. laevis*, a zebrafish (*D. rerio*), a mouse (*M. musculus*) and a human (*H. sapiens*).

Figure 7:
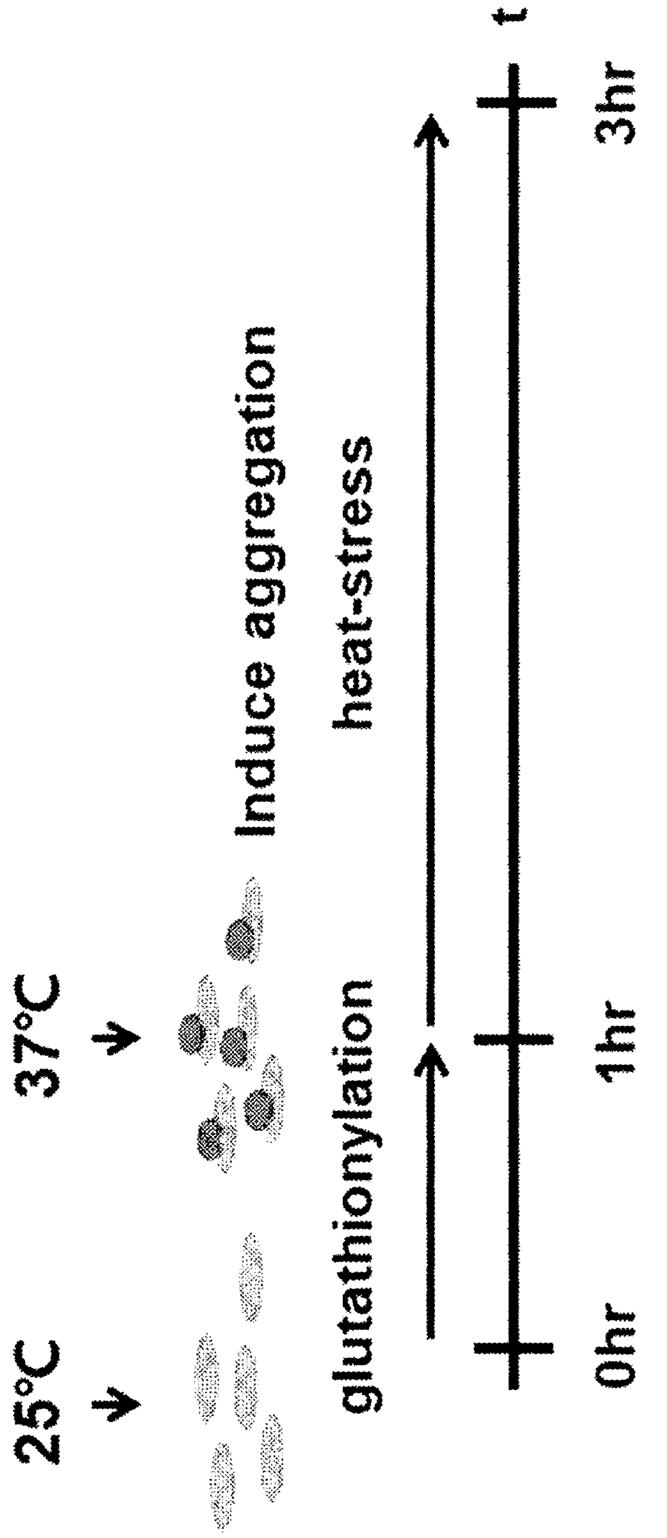
FIG. 7 schematically shows an experiment for forming a FUS protein aggregate.

Example 6. Confirmation of Formation of Aggregate According to Glutathionylation of FUS Protein 6-1. Analysis of Solubility of Glutathionylated FUS As confirmed in Examples 1 to 3, the glutathionylated human FUS protein aggregate is observed in the cytoplasm of neurons of the *Drosophila* brain, as confirmed in Example 5, glutathionylation occurs at Cys-447 of the RanBP2 zinc-finger domain in FUS proteins. Based on this example, to confirm whether the glutathionylation of FUS proteins affects the formation of FUS protein aggregates, an experiment of measuring the solubility of a glutathionylated FUS protein was carried out. Specifically, as shown in FIG. 7, the oxidized glutathione (glutathione disulfide, GSSH) was added to a myc-labeled human FUS protein purified from HEK293 cells to induce the glutathionylation of a human FUS protein, and then exposed to protein toxic stress, that is, heat-stress. The solubility of the glutathionylated human FUS protein was measured at different points of time through western blotting analysis by quantifying the human FUS protein in fractions of a supernatant and pellet of each sample.

Figure 8:
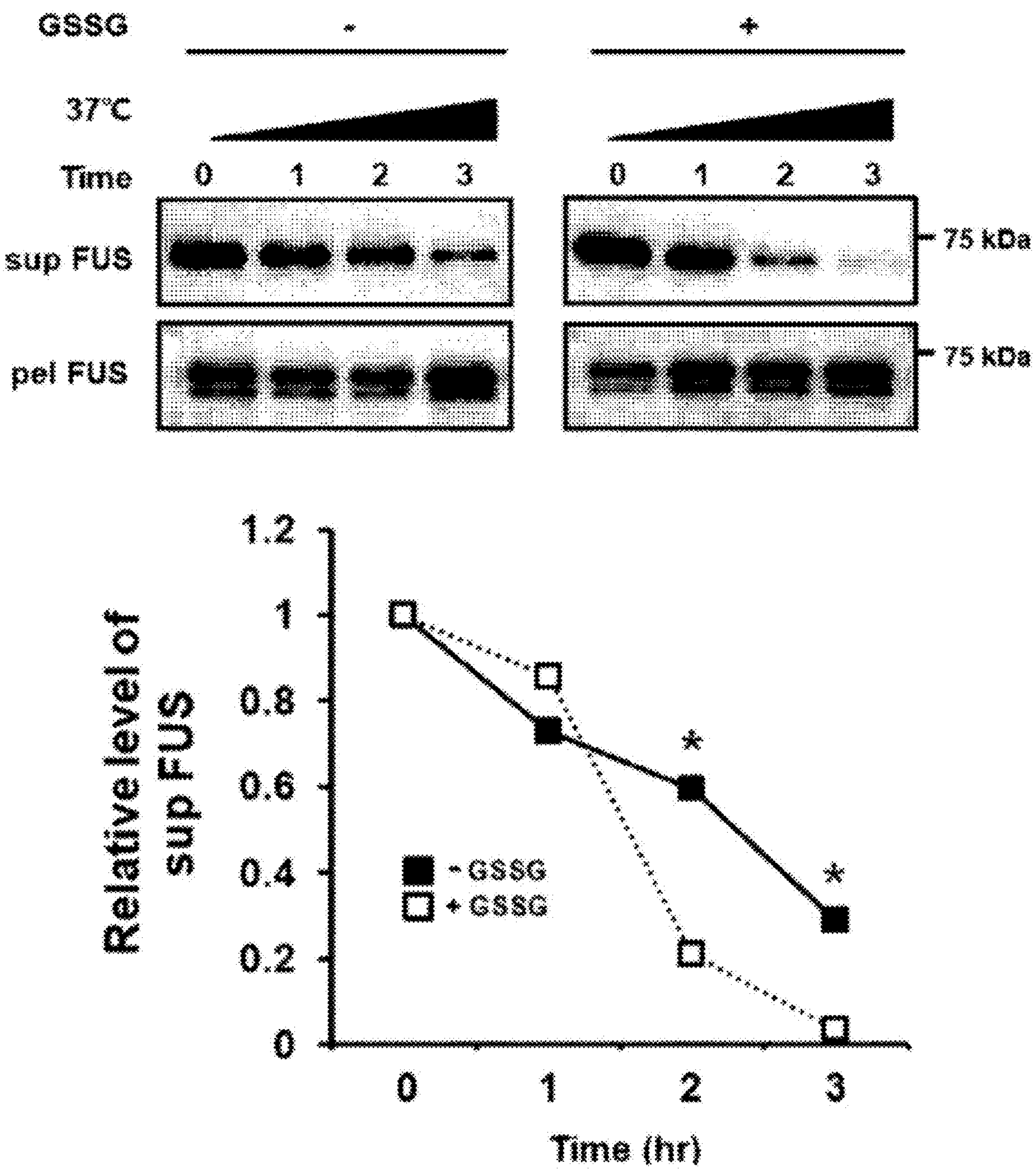
FIG. 8 shows the comparison of the solubility of a glutathionylated FUS protein aggregate and an unglutathionylated FUS protein through western blotting analysis.

As a result, as shown in FIG. 8, it was confirmed that a soluble fraction of the human FUS protein without addition of the oxidized glutathione (glutathione disulfide, GSSH) maintained a high level of solubility at 37° C. for 2 hours.

In addition, as a result of measuring the solubility of the soluble fraction of the glutathionylated human FUS protein under the above-described conditions by adding the oxidized glutathione (glutathione disulfide, GSSH), it was confirmed that the degree of solubility dramatically decreased from 90% to 20%.

Summarizing the above result and the result of Example 5, it was confirmed that the glutathionylation of a FUS protein induces the formation of a FUS protein aggregate.

6-2. Analysis of Three-Dimensional Homologous Model of RanBP2 Zinc-Finger Domain of FUS To obtain the structural basis for the relative location of the Cys-447 residue, the three-dimensional homology model of the RanBP2 zinc-finger domain in a human FUS protein was created using an I-TASSER server, and the RanBP2 zinc-finger domain model was used to search for a protein having a structurally homologous region in the protein database bank (PDB).

Figure 9:
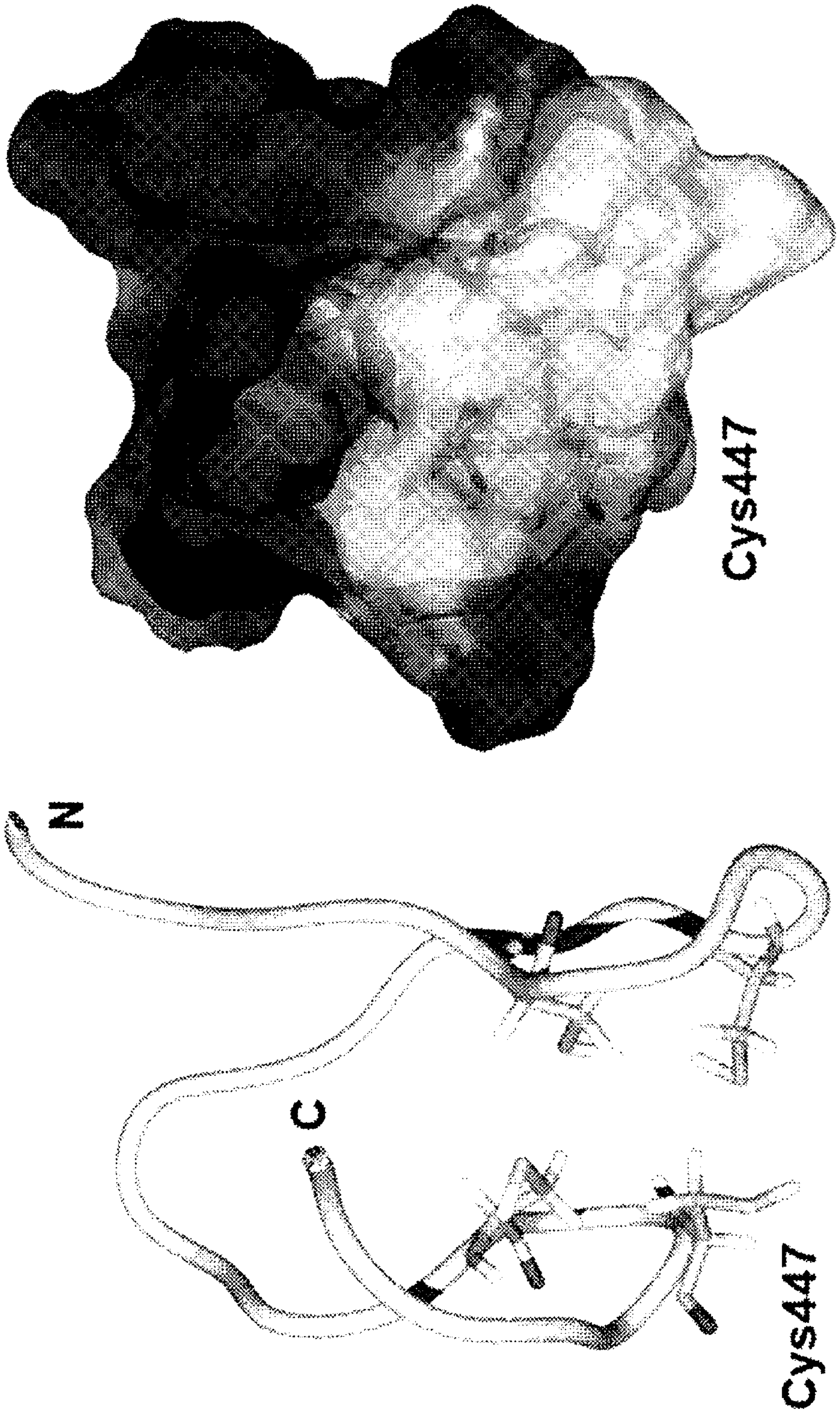
FIG. 9 shows a three-dimensional homology model of the RanBP2 zinc-finger domain of a FUS protein and the relative location of Cys-447.

As a result, as shown in FIG. 9, it was confirmed that the Cys-447 residue in the RanBP2 zinc-finger domain is exposed at the surface for oxidative modification. Based on the structure of the predicted three-dimensional homology model, high susceptibility of Cys-447 in glutathionylation of a human FUS protein was suggested, and the possibility of the structural change in the RanBP2 zinc-finger domain was proven.

Example 7. Confirmation of FUS Glutathionylation

Glutathionylation is a result of a disulfide bond between a cysteine and reduced glutathione (GSH), which is known to lead to changes in the structure and function of a protein.

Figure 10A:
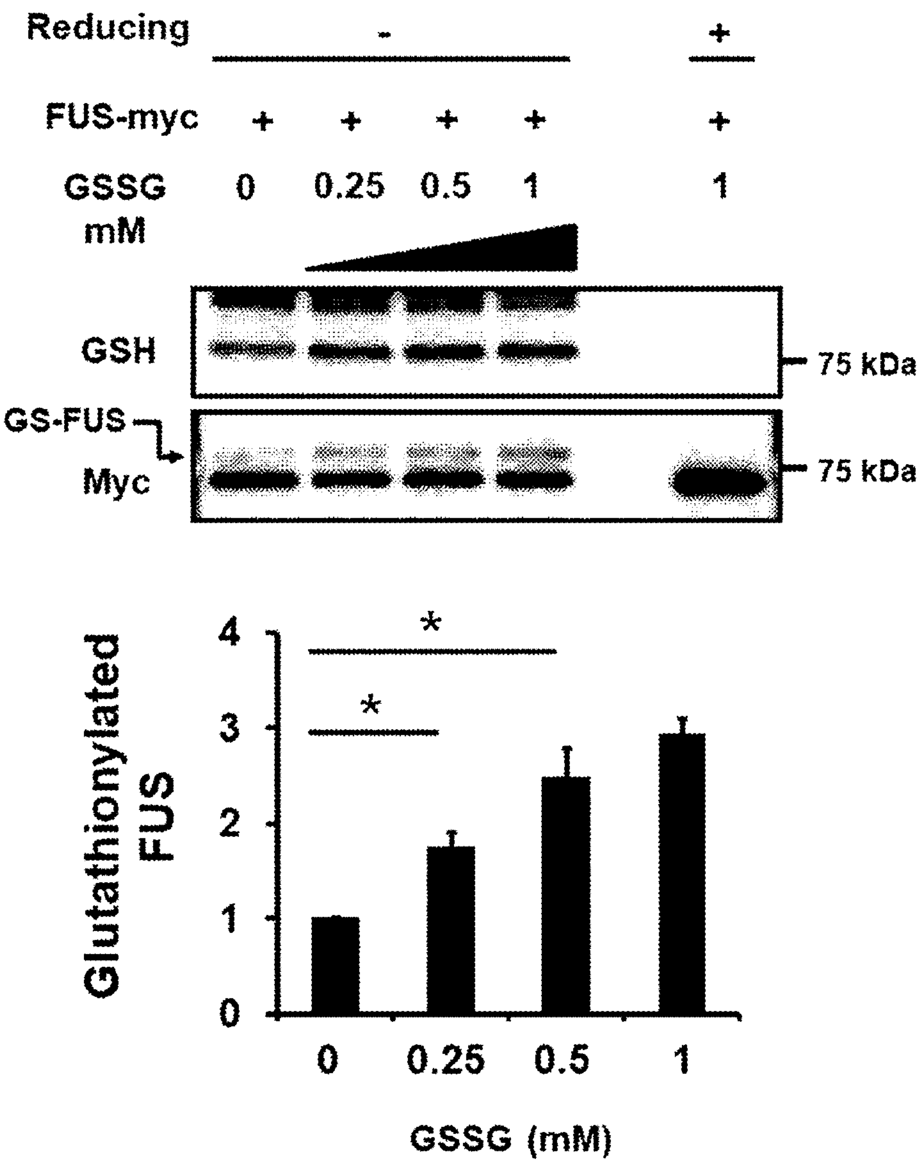
FIG. 10A shows the result of confirming the glutathionylation of a FUS protein in the presence of GSSG.

To confirm whether FUS glutathionylation occurs, as a result of analyzing in vitro glutathionylation, as shown in FIG. 10A, it was confirmed that a wild-type FUS protein is glutathionylated in the presence of various concentrations of the oxidized glutathione (GSSG), and in addition, as a result of confirming the FUS glutathionylation by western blotting analysis using anti-GSH and anti-myc antibodies, it was confirmed the glutathionylated FUS is reduced into FUS by treatment of 2-mercaptoethanol that cleaves a mixed disulfide bond or a reducing agent such as dithiothreitol. That is, it was demonstrated that the glutathionylation of a FUS protein occurs depending on a GSSG concentration.

In addition, to confirm in vivo FUS glutathionylation, human FUS specifically expressed in neurons were expressed in *Drosophila* neurons using an elav-Gal4 driver.

Figure 10B:
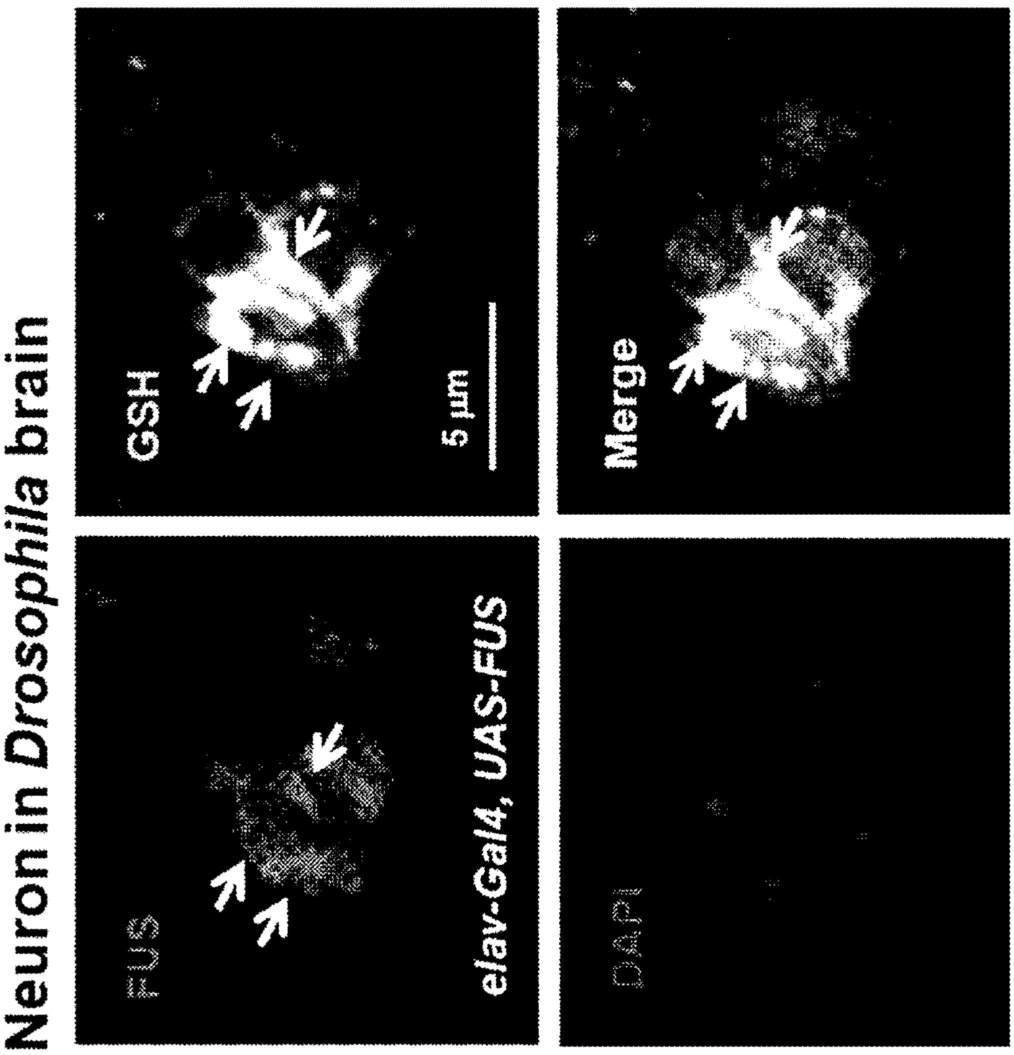
FIG. 10B shows the result of confirming that a glutathionylated FUS protein is located in the cytoplasm of a *Drosophila* brain neuron.

As a result, as indicated by the white arrows of FIG. 10B, it was confirmed that the FUS protein was mainly limited in the nucleus of a neuron, but a large amount of cytoplasmic FUS aggregates were observed in neurons of the FUS-overexpressing fly brain. In addition, interestingly, it was confirmed that the cytoplasmic and mislocalized FUS are commonly localized with GSH in the brain tissue as shown in the result of the in vitro research.

Figure 10C:
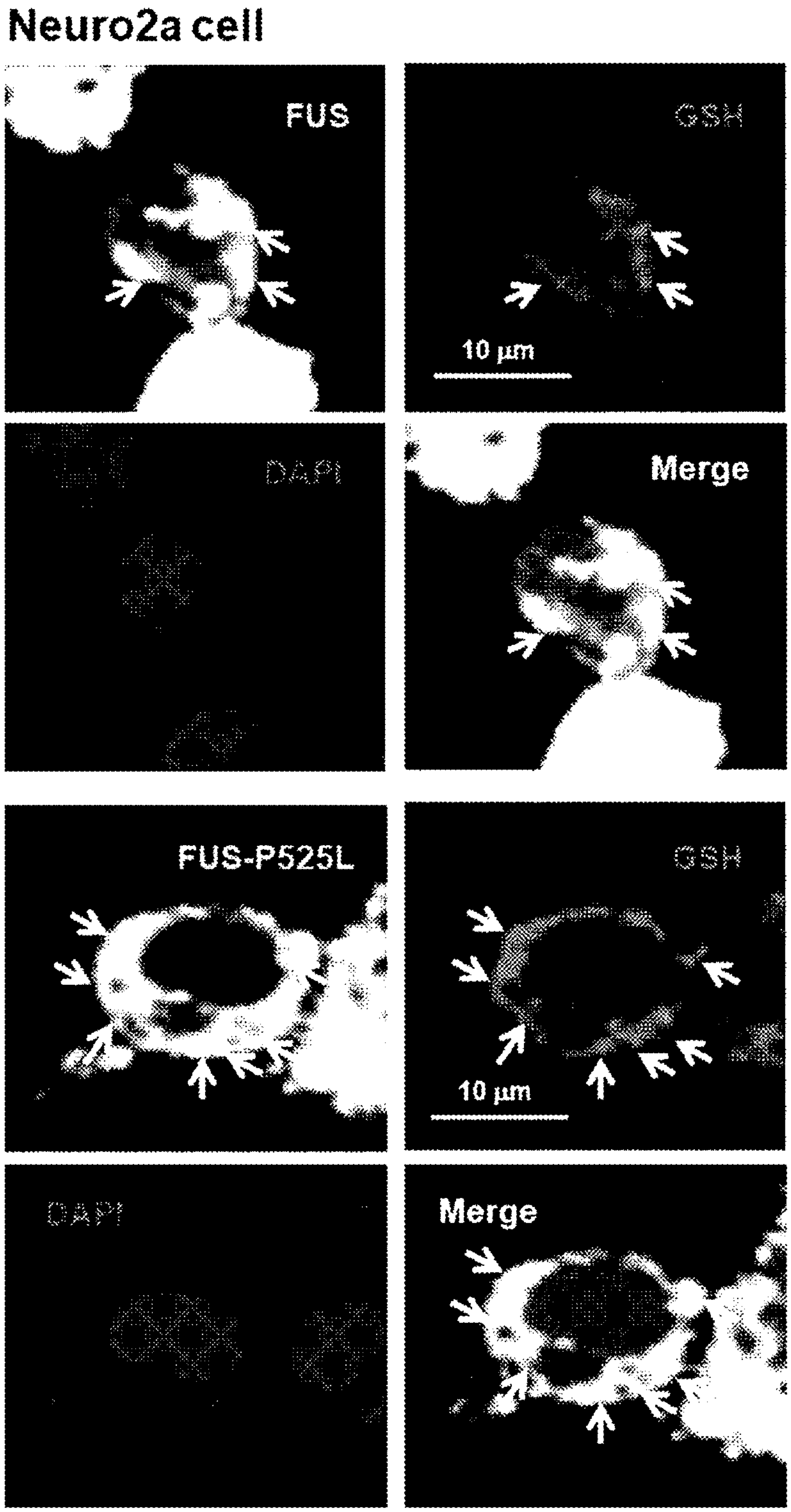

Subsequently, to confirm whether the glutathionylation of FUS and its mutant $FUS^{P252L}$ also shows the above-described result in a mammalian system, as a result of expressing human FUS and $FUS^{P525L}$ in a mouse neuroblastoma cell line, Neuron2a (N2a), as shown in FIG. 10C, it was confirmed that a GSH-positive signal is localized to the FUS or $FUS^{P525L}$ aggregate.

Therefore, it was confirmed that FUS and $FUS^{P525L}$ are glutathionylated both in vitro and in vivo.

Finally, to identify a glutathionylation site, the glutathionylation of myc-tagged human FUS was induced in vitro, and a band was detected using a Coomassie stained gel. The FUS protein band was cut from the gel, digested with trypsin and subjected to analysis through MALDI-mass spectrometry.

As a result, as shown in FIG. 5, peptides having a mass difference of 305 Da indicating one GSH moiety were detected through mass spectrometry. The RanBP2 zinc-finger (ZnF) domain of FUS has four cysteines, and may be sensitive to in vivo oxidative stress.

In addition, the FUS sequence relating to cysteine conservation in eukaryotes was investigated, confirming that all four cysteines are well conserved from flies to humans, and among these, a glutathionylation site in the RanBP2-type ZnF domain, Cys-447, (FIG. 7, arrows) was confirmed.

Therefore, it was confirmed that human FUS is specifically glutathionylated at the Cys-447 residue

Example 8. Confirmation of Formation of Aggregate According to FUS Glutathionylation Post-translational modification is known as a main mediator in pathogenic protein aggregation in various neurodegenerative diseases including amyotrophic lateral sclerosis (ALS). As shown in FIG. 1B, the inventors previously confirmed that the cytoplasmic or mislocalized FUS protein was commonly localized along with GSH in the *Drosophila* brain. The experimental background indicates that Cys-477 glutathionylation possibly induces the generation of a FUS aggregate in the ZnF domain of FUS. Therefore, it was predicted that the FUS aggregation in the cytoplasm can be regulated by FUS glutathionylation.

To confirm whether FUS glutathionylation at the Cys-477 residue regulates the aggregation of a FUS protein, a solubility test for FUS was carried out.

More specifically, glutathionylation was induced by addition and incubation of the myc-tagged human FUS protein purified from HEK293 cells along with GSSG, and exposed to heat shock to give protein toxic stress (see FIG. 7).

FUS solubility was evaluated by quantifying FUS proteins in fractions of the supernatant and pellet of each sample through western blotting analysis at different points of time.

As a result, as shown in FIG. 8, while a FUS protein which was not treated with GSSG can remain high soluble at 37° C. for 2 hours, it was confirmed that the solubility of a soluble fraction of the FUS protein after glutathionylation was induced by GSSG treatment dramatically decreased from 90% to 20% compared to the FUS protein which is not treated with GSSG after 2 hours.

This shows that FUS glutathionylation significantly induces the formation of an aggregate, and the FUS glutathionylation of the Cys-447 residue induces protein aggregation, and as a main determinant for the formation of FUS aggregates, a hypothesis that can support cysteine glutathionylation can be proven.

In addition, to further evaluate the structural basis on the relative location of Cys-447 residue, a three-dimensional homology model of the human FUS ZnF domain was created using I-TASSER server, and the FUS ZnF domain model was used to search for a protein having a structurally homologous region in the PDB.

As a result, as shown in FIG. 9, it was confirmed that the Cys-447 residue in the ZnF domain is exposed at the surface for oxidative modification, suggesting that the high susceptibility of Cys-447 to glutathionylation can be proven, and a structural change in the ZnF domain is possible.

Example 9. Confirmation of Effect of GstO2 on Inhibiting Neurocytotoxicity Due to FUS To reduce pathology caused by glutathionylated FUS, an exact molecular mechanism and a protein, which can regulate a glutathionylation process was intended to be identified, and omega class glutathione transferase (GSTO) was selected as a potential candidate.

According to previous reports, human GSTO1 is known to serve as a deglutathionylation enzyme, and the inventors reported previously that GstO2, which is a *Drosophila* homologous chromosome of the human GSTO1, inhibits neurotoxicity by regulating the glutathionylation of the β subunit of ATP synthase in a *Drosophila* PD model (Kim et al., 2012).

Based on the above background knowledge, the inventors used *Drosophila* as a genetic tool to identify a novel role and regulatory factor for glutathionylation in the pathogenesis of ALS induced by FUS. First, it was intended to confirm whether increased GstO2 can reduce phenotypes caused by the overexpression of human FUS in *Drosophila*.

More specifically, to evaluate the functional relationship between GstO2 and FUS in *Drosophila*, transformed *Drosophila* exhibiting GstO2 overexpression and eye-specific Gal4 or GMR-Gal4-induced FUS expression was produced.

Meanwhile, according to a recent study using a *Drosophila* genetic approach, FUS expression in the eyes of an adult insect is known to exhibit a rough eye phenotype, and like a previous report, FUS expression showed a rough eye phenomenon, and it was confirmed that ommatidial tissue was disrupted.

Figure 11A:
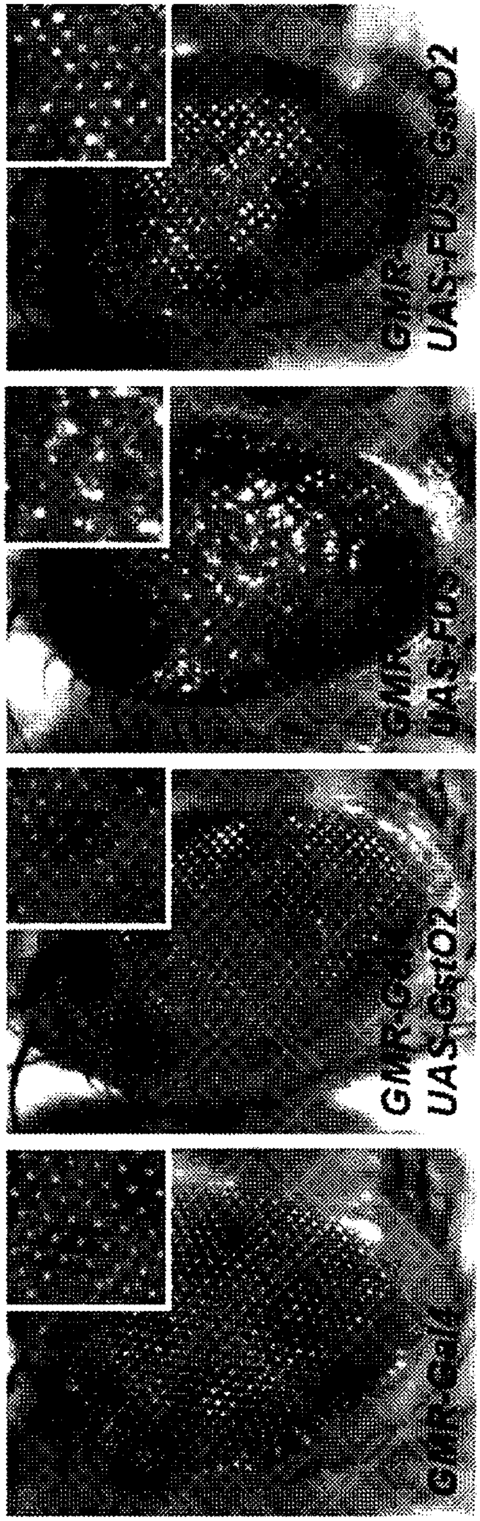
FIG. 11A shows the result of confirming the eye phenotype of FUS-expressing flies according to GstO2.

However, it was confirmed that coexpression of FUS and GstO2 significantly recovers a rough eye phenotype, and a change in disrupted eyes was not found in a fly only expressing GstO2 (FIG. 11A). These results show that GstO2 genetically interacts with FUS in *Drosophila.*

Next, to confirm the locomotive activity defect mechanism by FUS expression using pan-neuronal Gal4 and elav-Gla4, a larval crawling assay was performed to investigate the locomotive activity of larvae expressing FUS in neurons.

Figure 11B:
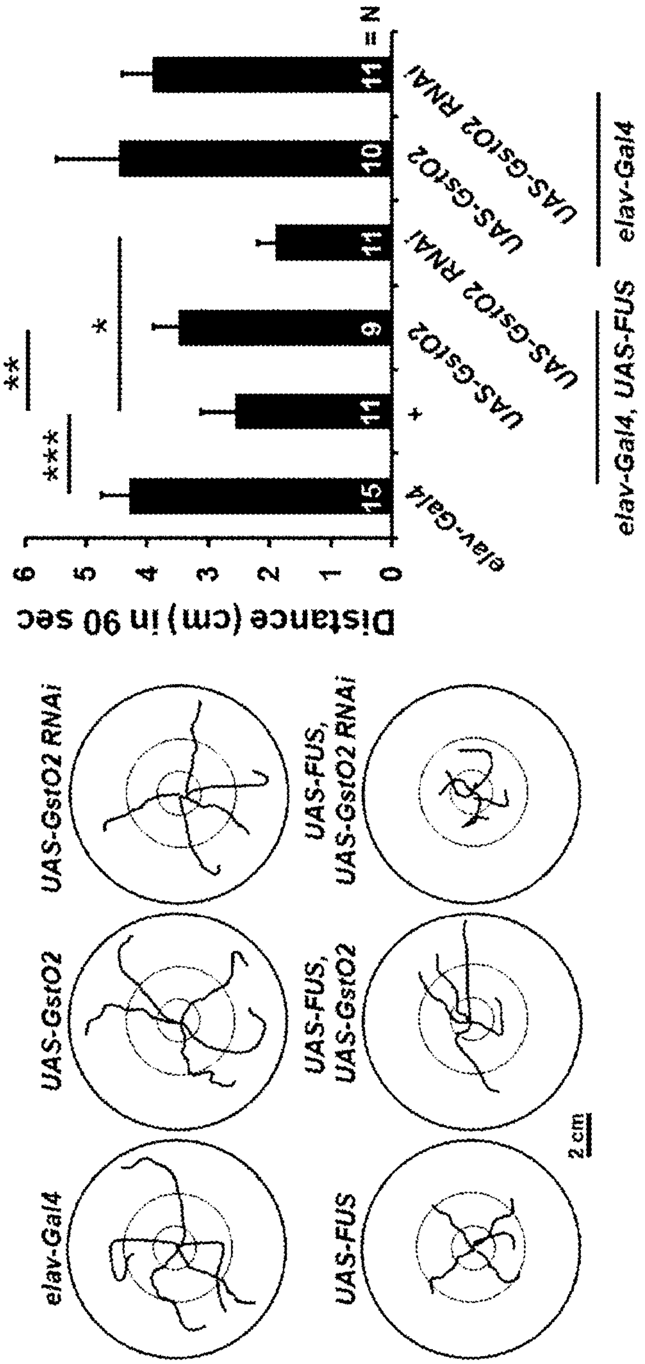
FIG. 11B shows the result of confirming the larva crawling activity of FUS-expressing flies according to GstO2.

As a result, as shown in FIG. 11B, it was confirmed that the *Drosophila* expressing FUS in neurons has greatly decreased locomotive activity compared to a control, and when coexpressing GstO2, it was confirmed that the *Drosophila* expressing FUS in neurons has improved larval crawling behavior. On the other hand, it was confirmed that larva expressing GstO2-knockdown FUS loses crawling behavior. Meanwhile, it was confirmed that the overexpression or knockdown of GstO2 alone does not have any effect on larval crawling behavior.

From these results, the inventors investigated the number of synaptic boutons at a neuron muscular junction (NMJ) to confirm whether a larval locomotive activity defect results from a defect in the NMJ.

Figure 11C:
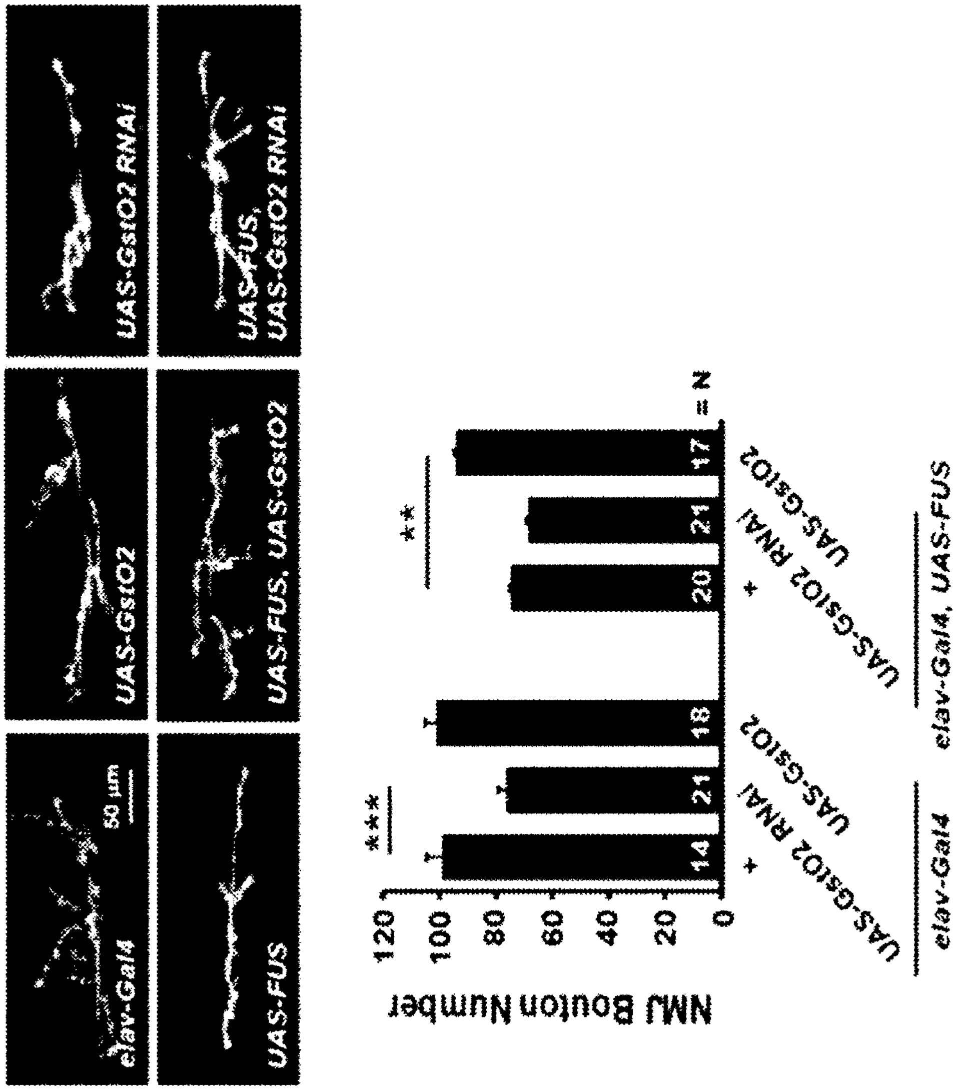
FIG. 11C shows the result of confirming the number of synaptic boutons at a neuromuscular junction (NMJ) of FUS-expressing flies according to GstO2.

As a result, as shown in FIG. 11C, it was confirmed that the total bouton number is considerably reduced at the NMJ of the fly expressing FUS under the regulation of elav-Gal4, but this phenotype is considerably recovered by coexpression of GstO2. However, GstO2 alone did not have the effect of inhibiting a decrease in the number of boutons, but it was confirmed that flies expressing GstO2-knockdown FUS were not decreased in the number of boutons at the NMJ.

Figure 11D:
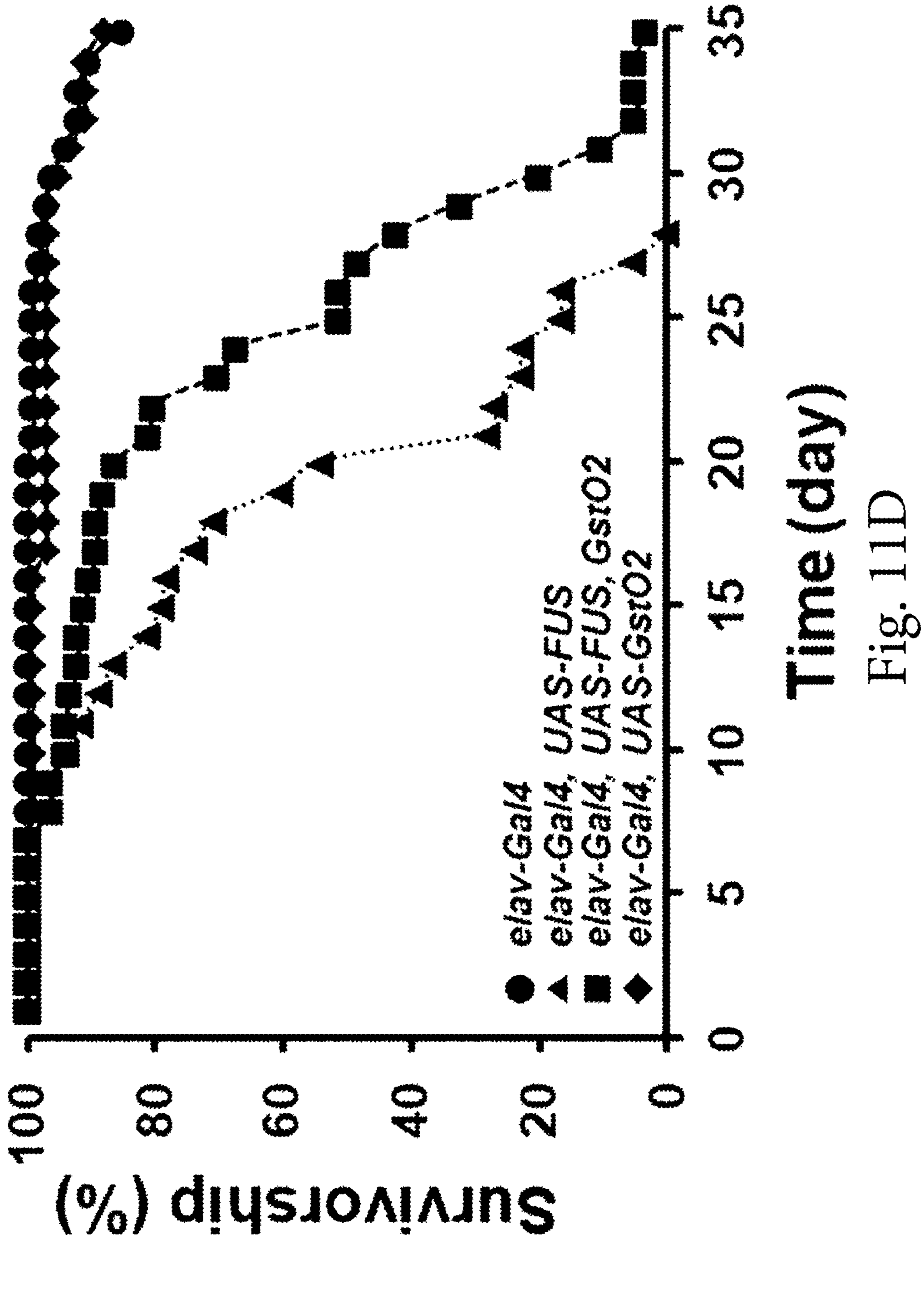
FIG. 11D shows the result of confirming the lifespan of FUS-expressing flies according to GstO2.
Figure 11E:
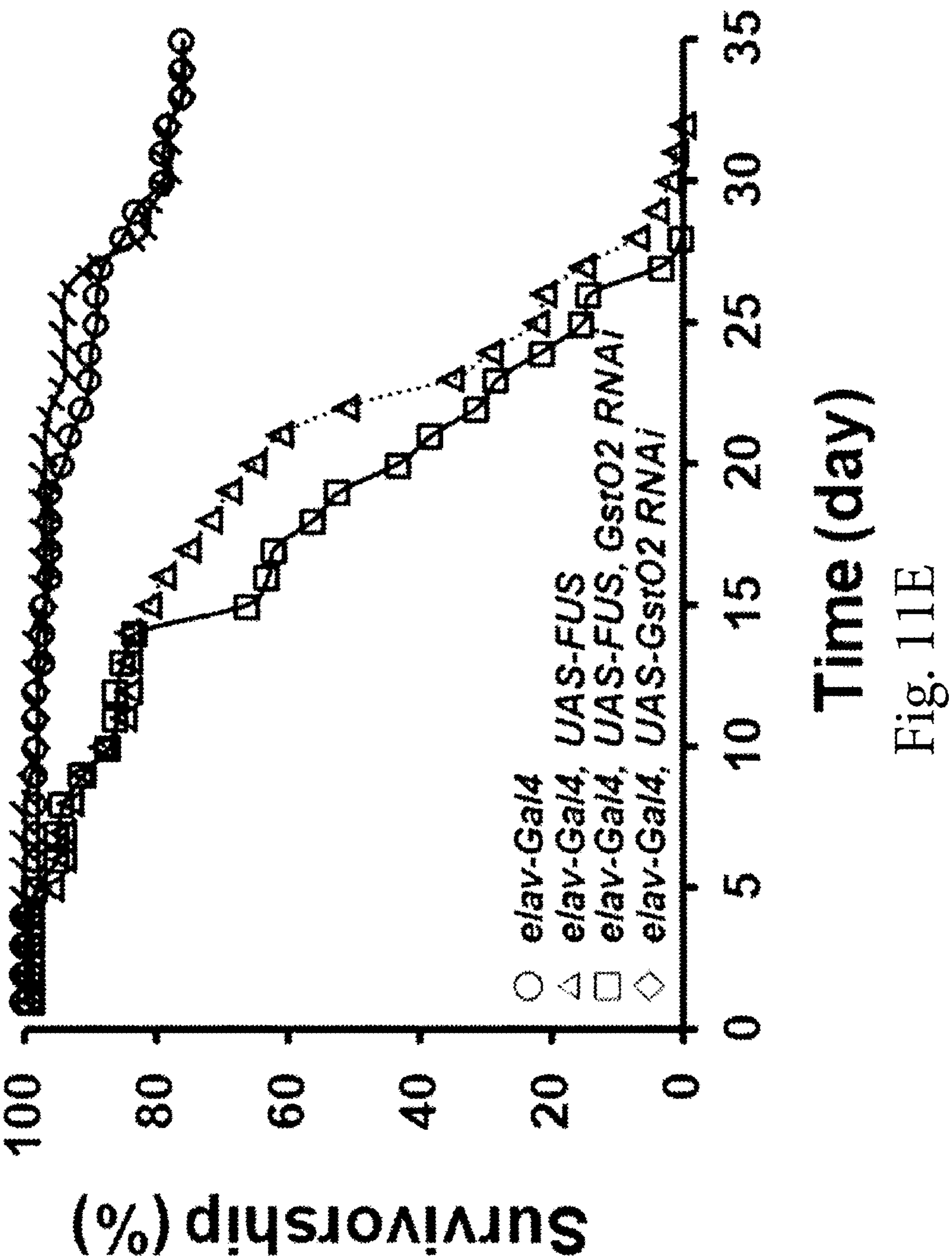
FIG. 11E shows the result of confirming the lifespan of FUS-expressing flies according to GstO2-knockdown.

In addition, as shown in FIG. 11D, it was confirmed that the expression of FUS in neurons greatly shortens a lifespan, but the lifespan is restored by the coexpression of GstO2. However, as shown in FIG. 11E, in FUS-expressing flies, GstO2-knockdown not only partially shortened a lifespan, and but also was not affected by GstO2 RNAi, either.

Figure 11F:
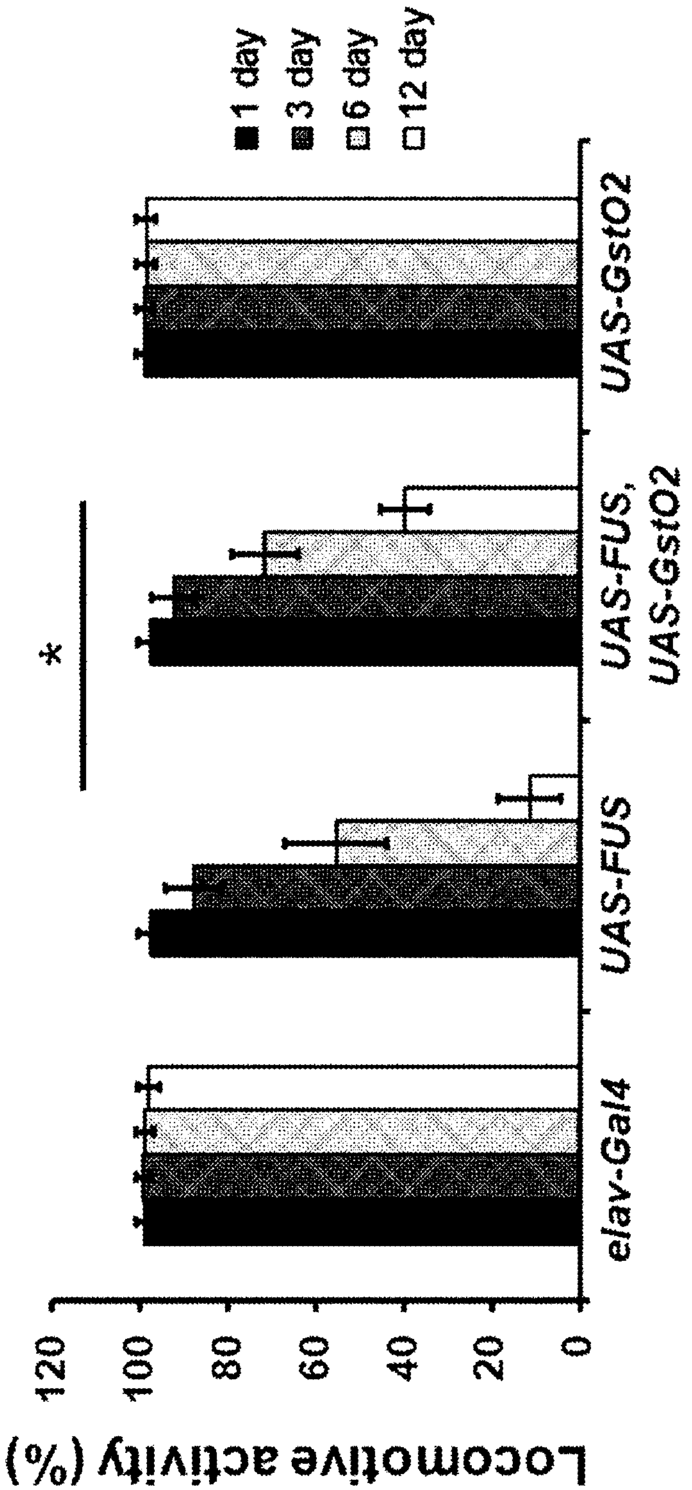
FIG. 11F shows the result of confirming the climbing activity of FUS-expressing flies according to GstO2.

Meanwhile, a negative geotaxis assay is an assay for evaluating the dysfunction of the nervous system in research on various neurodegenerative diseases including ALS, and as a result of applying it to the *Drosophila* model system according to the present disclosure, as shown in FIG. 11F, consistent with previous research, it was confirmed that FUS-expressing flies exhibited significantly reduced climbing activity compared to an age-matched control, but it was confirmed that a climbing defect was significantly inhibited in the case of FUS-expressing flies in which GstO2 is coexpressed in neurons. Here, it was confirmed that GstO2 overexpression alone does not affect climbing capacity.

Therefore, from the data, it was confirmed that FUS-induced neurotoxicity can be remarkably inhibited or reinforced through the regulation of GstO2 expression.

Example 10. Confirmation of FUS-Induced Mitochondrial Dynamics and Inhibition of OXPHOS Dysfunction Due to GstO2

It is known that abnormal mitochondria are consistently observed in animal models of ALS (Dal Canto and Gurney, 1994; Magrane et al., 2014). In addition, the overexpression of mutant FUS in motoneurons led to mitochondrial division (Tradewell et al., 2012), the expression of wild-type and mutant FUS in NSC34 motoneurons reduced mitochondrial ATP production (Stoica et al., 2016). Although mitochondrial dysfunction remains a common feature of ALS in various previous studies, it has not yet been proven that, in FUS-induced proteinopathy, mitochondrial dynamics and the dysfunction of the oxidative phosphorylation (OXPHOS) system are the major causes for ALS pathology. Therefore, the inventors confirmed in previous research that mitochondrial division is reinforced in muscles or motoneurons in FUS-expressing flies, and Marf instability caused by a mitochondrial fusion protein results in unbalanced mitochondrial dynamics (Altanbyek et al., 2016).

On the basis of the above research results, it was intended to confirm whether GstO2 expression induces mitochondrial division in FUS-expressing flies, and to this end, the GstO2 effect on thoracic muscles in FUS-expressing flies was characterized.

To characterize the GstO2 effect, a FUS-expressing *Drosophila* line were crossed with muscle-specific Gal4 and Mhc-Gal4, and then the mitochondria were visualized by expression of mitochondria-targeted GFP (mitoGFP).

Figure 12A:
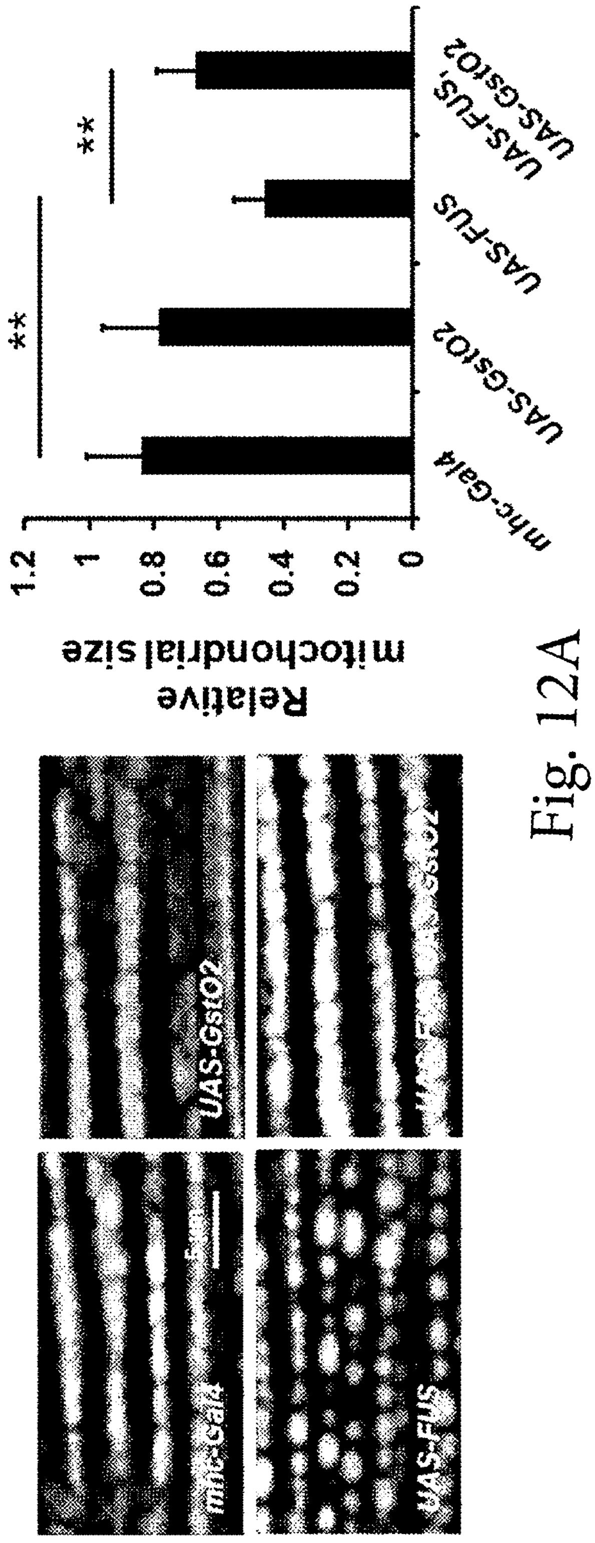
FIG. 12A shows the result of confirming the mitochondrial size of FUS-expressing flies according to GstO2.

As a result, as shown in FIG. 12A, in the FUS-expressing flies, it was confirmed that the mitochondrial size is much smaller than that of the control and fragmentary mitochondria were identified, and in a group overexpressing GstO2 alone, a detectable change in mitochondrial morphology could not be found. However, in the FUS-expressing flies, when GstO2 was coexpressed, it was confirmed that the mitochondrial size is dramatically recovered.

Subsequently, to confirm whether GstO2 restores mitochondrial morphology in motoneurons, GstO2 was overexpressed using motoneuron-specific Gal4 and D42-Gal4, along with mitoGFP.

Figure 12B:
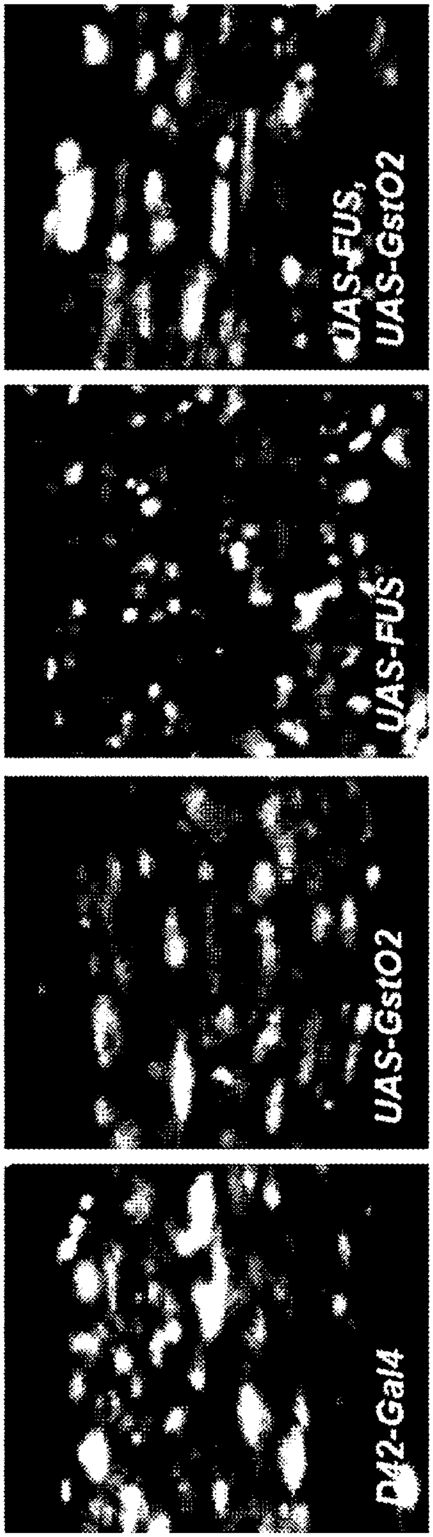
FIG. 12B shows the result of confirming the morphology of mitochondria of FUS-expressing flies according to GstO2.

As a result, as shown in FIG. 12B, consistent with the GstO2 recovery effect on mitochondria divided in muscles of FUS-expressing flies, it was confirmed that FUS expression in motoneurons of legs of adult flies increases mitochondrial division. However, such a phenotype was also confirmed to be inhibited by coexpression of GstO2.

In addition, it was investigated whether mitochondrial division was caused by the dysfunction of a protein that regulates mitochondrial dynamics. The inventors confirmed in previous research that Marf expression reduced in FUS-expressing flies induces excessive division of mitochondria (Altanbyek et al., 2016), and evaluated whether the Marf expression is changed by GstO2.

Figure 12C:
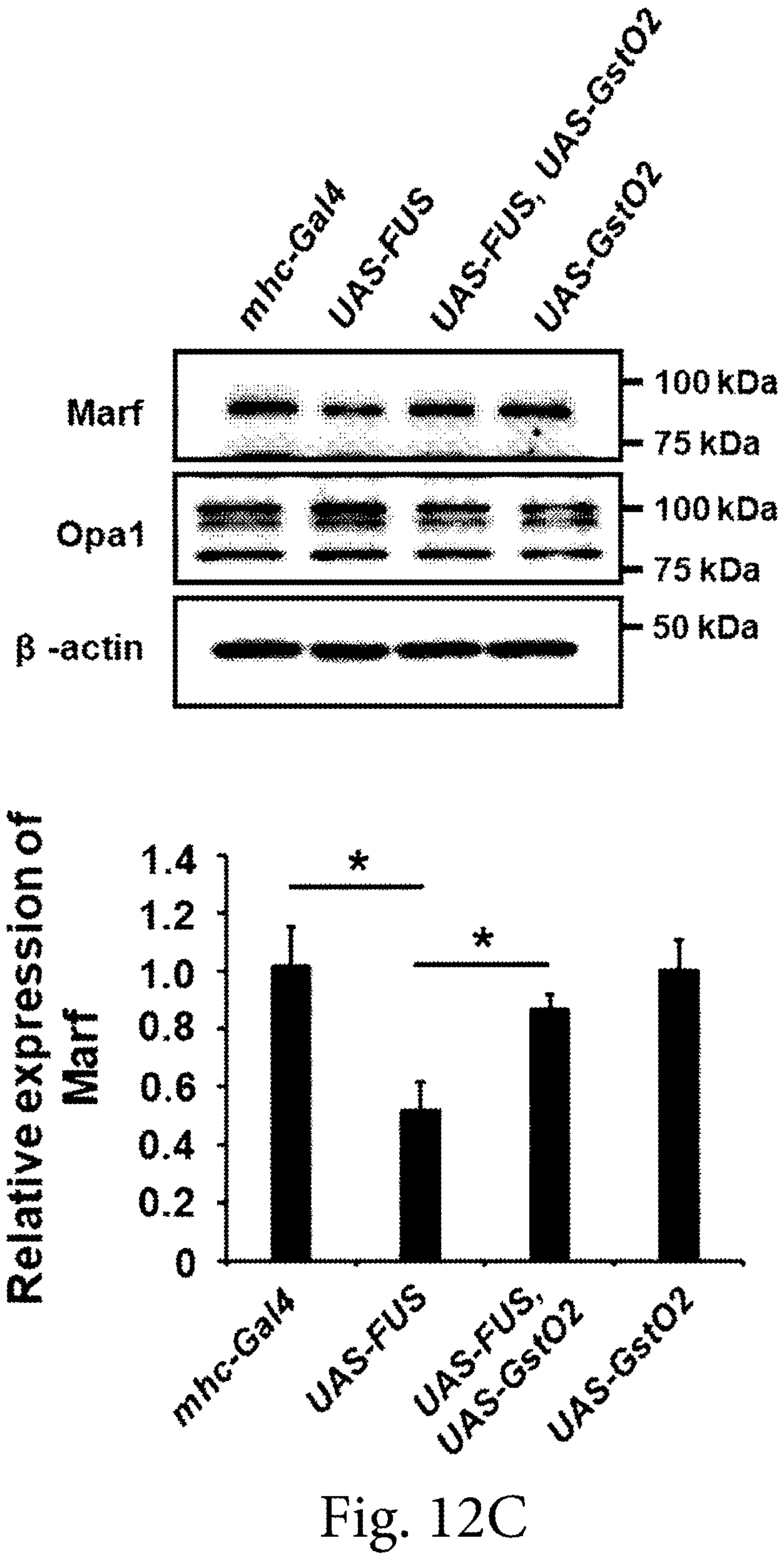
FIG. 12C shows the result of confirming the Marf expression of FUS-expressing flies according to GstO2.

As a result, as shown in FIG. 12C, in FUS flies coexpressing GstO2, it was confirmed that Marf expression is sufficiently increased, but an Opal level is maintained as is.

Subsequently, to confirm whether the morphological change of the mitochondria in FUS overexpression affects the OXPHOS system, the functional relevance of unbalanced mitochondrial dynamics in FUS-induced ALS was evaluated. More specifically, the content of a mitochondria complex was measured in the electron transport chain (ETC) indirectly measured by analyzing levels of various complex subunits of the FUS-expressing flies.

Figure 12D:
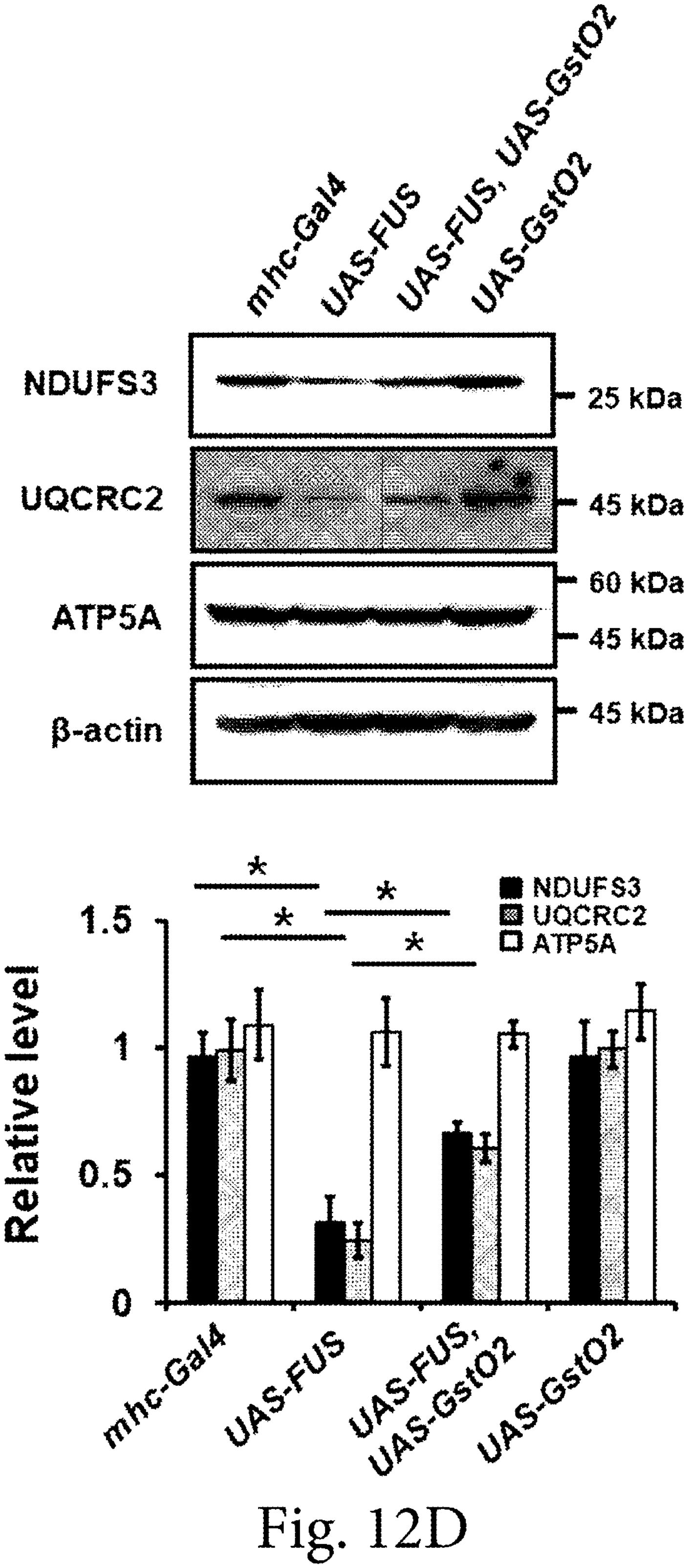
FIG. 12D shows the result of confirming the content of a mitochondria complex of FUS-expressing flies according to GstO2.

As a result, as shown in FIG. 12D, it was confirmed that FUS-expressing flies are remarkably decreased in the complex I subunit NDUFS3 and the complex III subunit UQCRC2, but have almost no change in the α-subunit of the complex V ATP5A. Meanwhile, since antibodies cross-reacting with any one of complex II and IV subunits in *Drosophila* could not be found, their contents could not be measured. Here, it was confirmed that GstO2 overexpression using FUS restores the concentrations of NUDFS3 and UQCRC2 to levels similar to those of the control.

To further research a complex assembly, blue native gel electrophoresis (BN-PAGE) was performed on the mitochondria purified from thoracic tissue in adult flies.

Figure 12E:
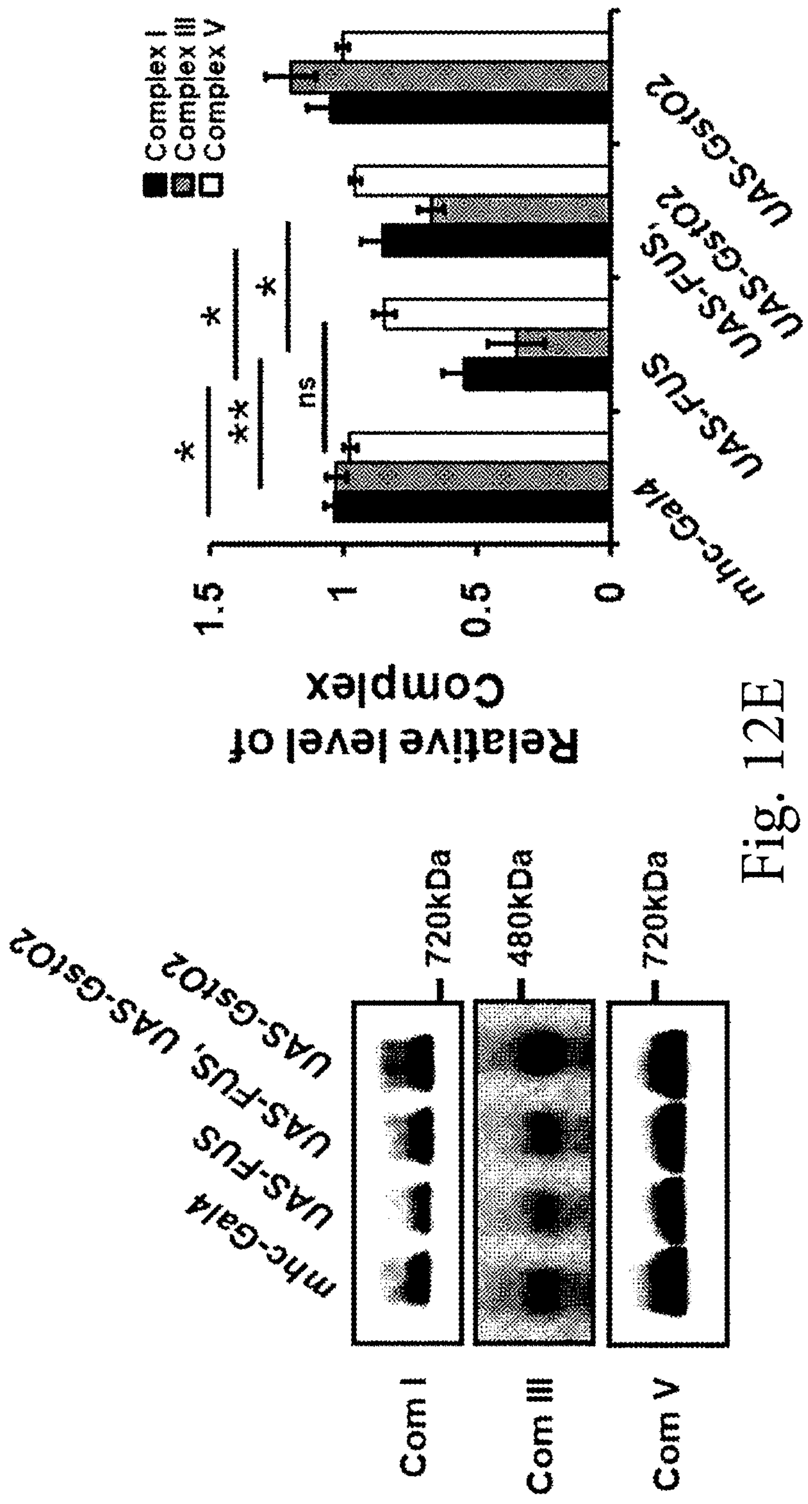
FIG. 12E shows the result of BN-PAGE performed on FUS-expressing flies according to GstO2.

As a result, as shown in FIG. 12E, consistent with the effect of reducing the expression of complex I and III subunits in FUS-expressing flies, BN-PAGE showed that the levels of assembly complexes I and III are reduced in the FUS-expressing flies. Particularly, although the dissociation of FUS-induced complexes I and III may be alleviated by the overexpression of GstO2, it was confirmed that the state of complex V assembly does not change even in all mutant lines.

Subsequently, to confirm whether GstO2 can restore mitochondrial functionality, the mitochondrial production of reactive oxygen species (ROS) FUS-expressing flies was measured using mitoSOX.

Figure 12F:
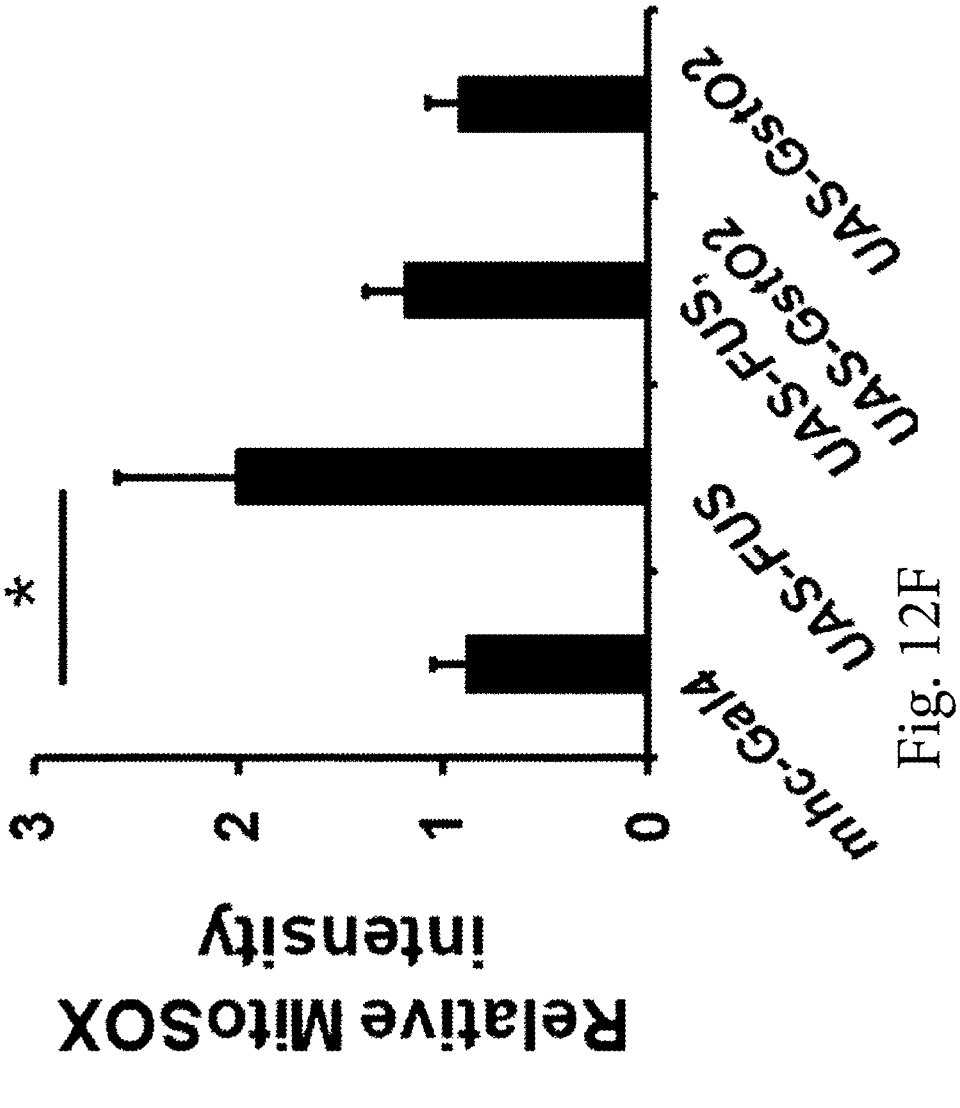
FIG. 12F shows the result of confirming the ROS production of FUS-expressing flies according to GstO2.

As a result, as shown in FIG. 12F, it was confirmed that ROS production increases in FUS-expressing flies, and is recovered by GstO2 expression.

Figure 12G:
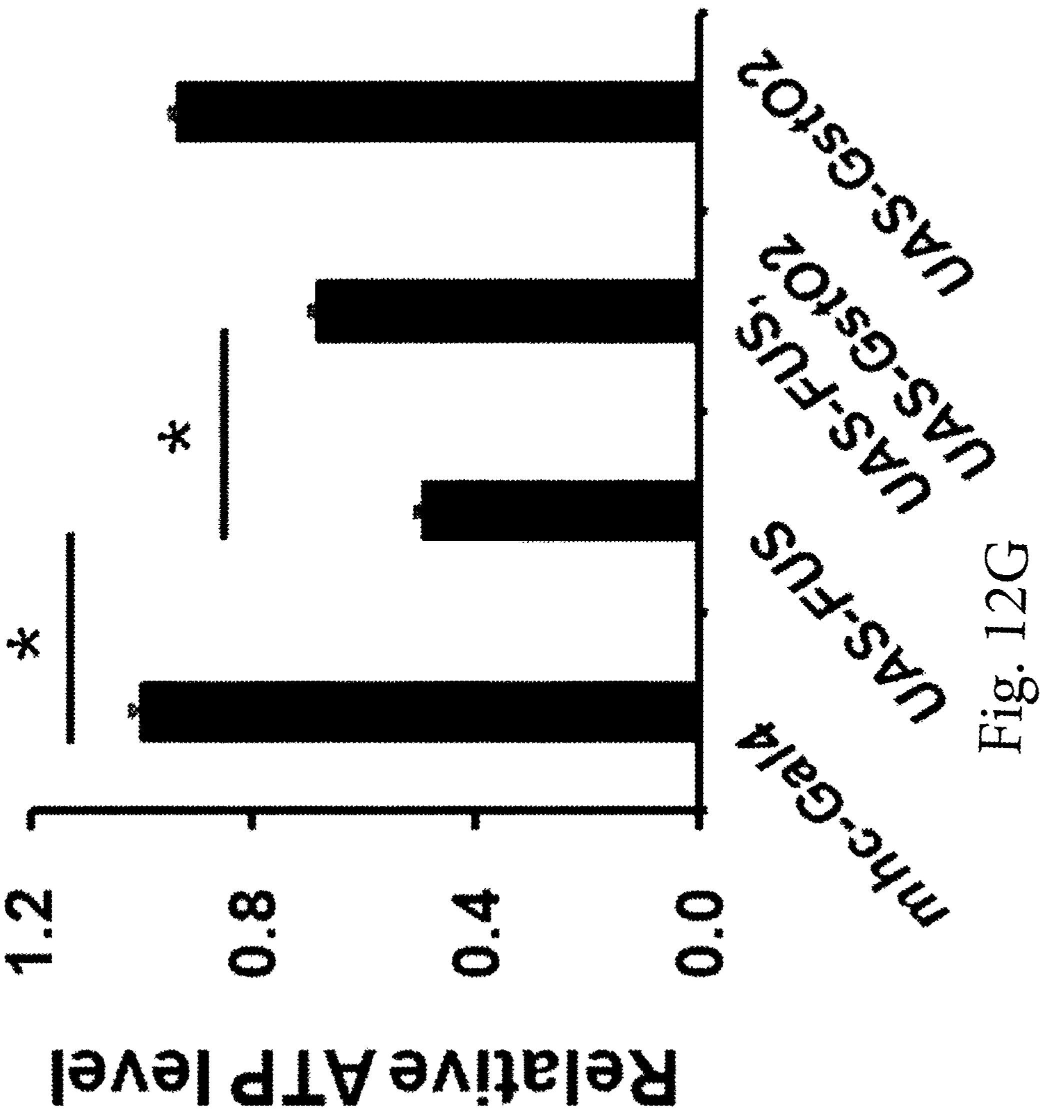
FIG. 12G shows the result of confirming the ATP level of FUS-expressing flies according to GstO2.

In addition, the mitochondria produce cellular energy in the form of ATP, and it was confirmed that the ATP level is remarkably reduced in the FUS-expressing flies compared to the control (FIG. 12G).

The amount of an oxidized protein in the cytoplasm was measured to confirm whether GstO2 can reduce an increase in oxidative stress in the cytoplasm.

Figure 12H:
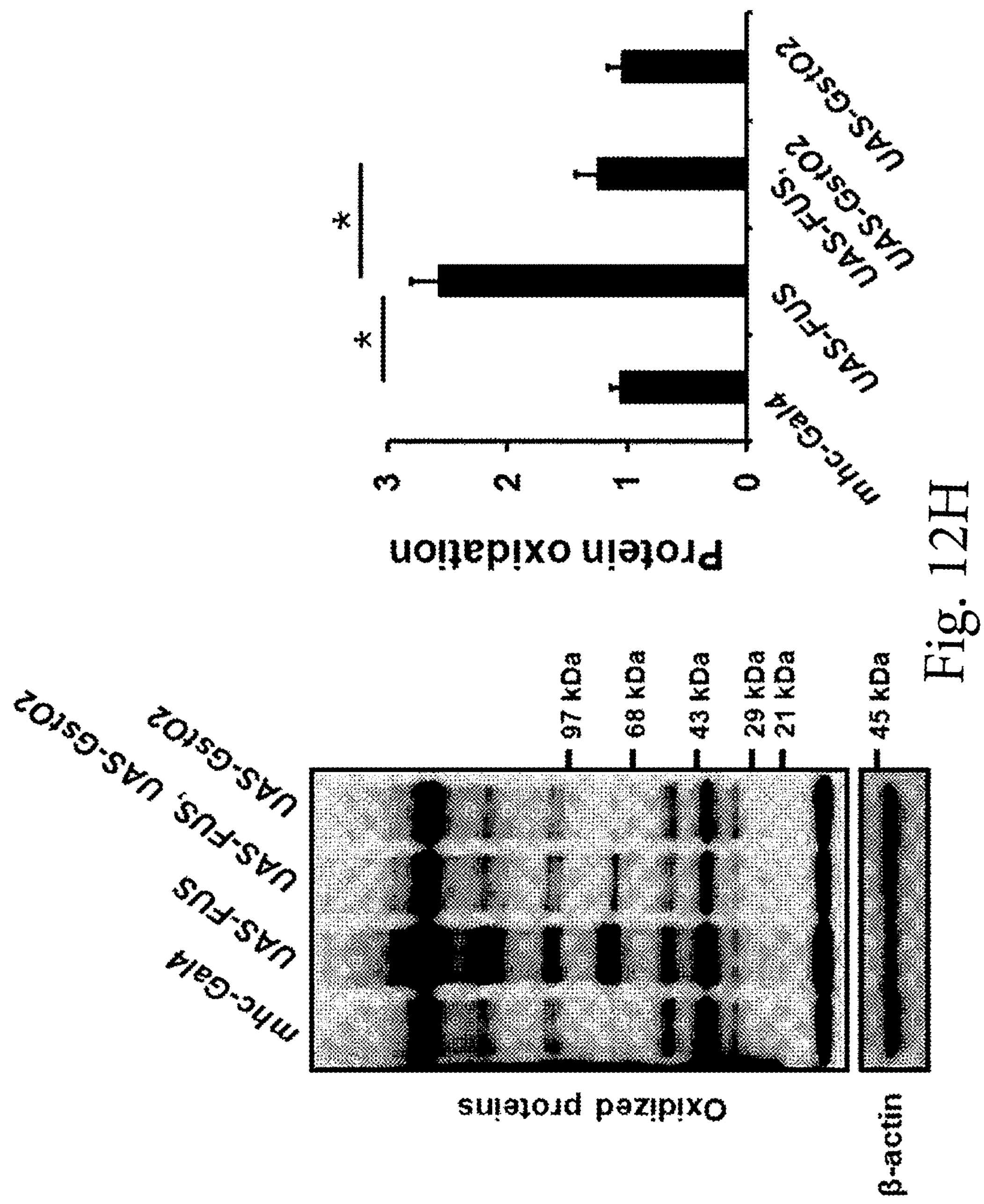
FIG. 12H shows the result of measuring the amount of oxidized protein in the cytoplasm in FUS-expressing flies according to GstO2.

As a result, as shown in FIG. 12H, it was observed that the oxidized protein was increased in the FUS-expressing flies, and it was confirmed that it is restored by GstO2 expression.

Therefore, it was confirmed that FUS-induced oxidative stress in the cytoplasm and unbalanced dynamics and the dysfunction of the mitochondria are remarkably prevented by GstO2.

Example 11. Confirmation of Inhibitory Effect of GstO2 on Formation of FUS Aggregate in *Drosophila* Neurons The above results that confirm that all defective phenotypes caused by FUS expression in *Drosophila* are suppressed by GstO2 overexpression show that GstO2 can promote a decrease in FUS, which is a pathogen, in neurons.

Therefore, to confirm the effect of inhibiting the formation of a FUS aggregate in GstO2-mediated *Drosophila* neurons, according to the immunoblotting result for the brain extract of a FUS-expressing adult fly, it was confirmed that coexpression of GstO2 does not affect a FUS level (see FIG. 13A), but as shown in FIG. 13B, it was confirmed that GstO2 knockdown increases FUS proteins in FUS-expressing flies.

Subsequently, to confirm whether GstO2 expression inhibits FUS mislocalization in brain tissue, nuclear/cytoplasmic fraction analyses were performed to measure FUS levels in the cytoplasm and nucleus.

As a result, as shown in FIG. 13C, in GstO2-FUS coexpression, it was confirmed that the FUS protein level was reduced in the cytoplasmic fraction, but not in the nuclear fraction. Therefore, it was confirmed that GstO2 can serve as a FUS toxicity inhibitor by reducing the level of FUS protein in the cytoplasm.

To further examine the effect of GstO2 on FUS aggregation in transgenic flies, fly heads of various genotypes were collected, and after dissolution in a modified lysis buffer, they were separated into detergent-soluble and insoluble fractions.

Figure 13D:
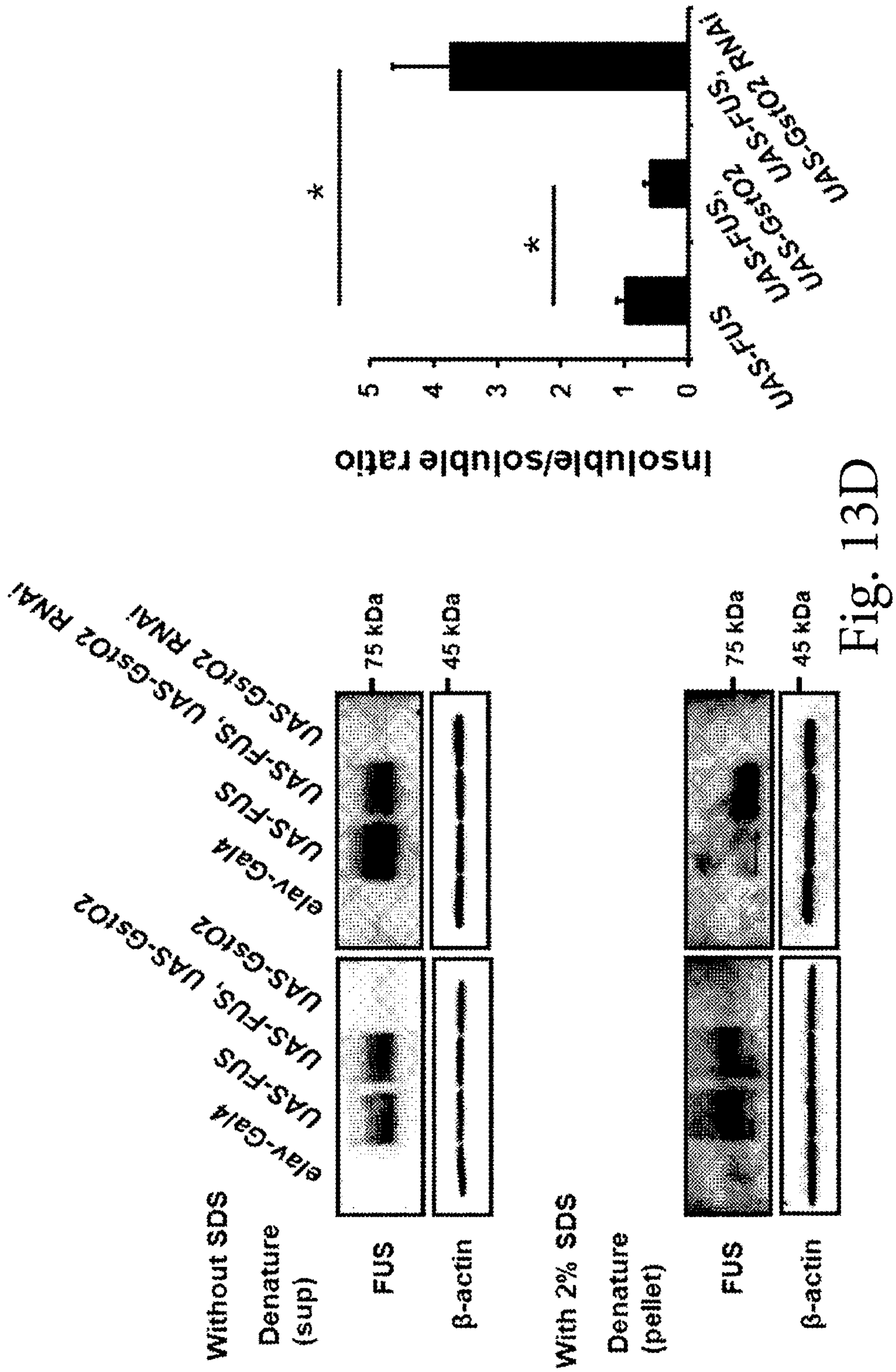
FIG. 13D shows the result of analyzing solubility to confirm a FUS aggregate of FUS-expressing flies according to GstO2.

As a result, as shown in FIG. FIG. 13D, it was confirmed that the flies coexpressing GstO2 and FUS significantly increased a FUS level in the soluble fraction, and decreased a FUS level in the insoluble fraction. On the other hand, it was confirmed that the neuron-specific knockdown of GstO2 induces FUS conversion from the soluble fraction into the insoluble fraction. In addition, compared to the FUS-expressing flies, through quantification of soluble and insoluble FUS, it can be seen that, in the GstO2-coexpressing flies, an insoluble/soluble FUS ratio was reduced to >40%, whereas in the GstO2 knockdown FUS-expressing flies, an insoluble/soluble FUS ratio greatly increased.

Figure 13E:
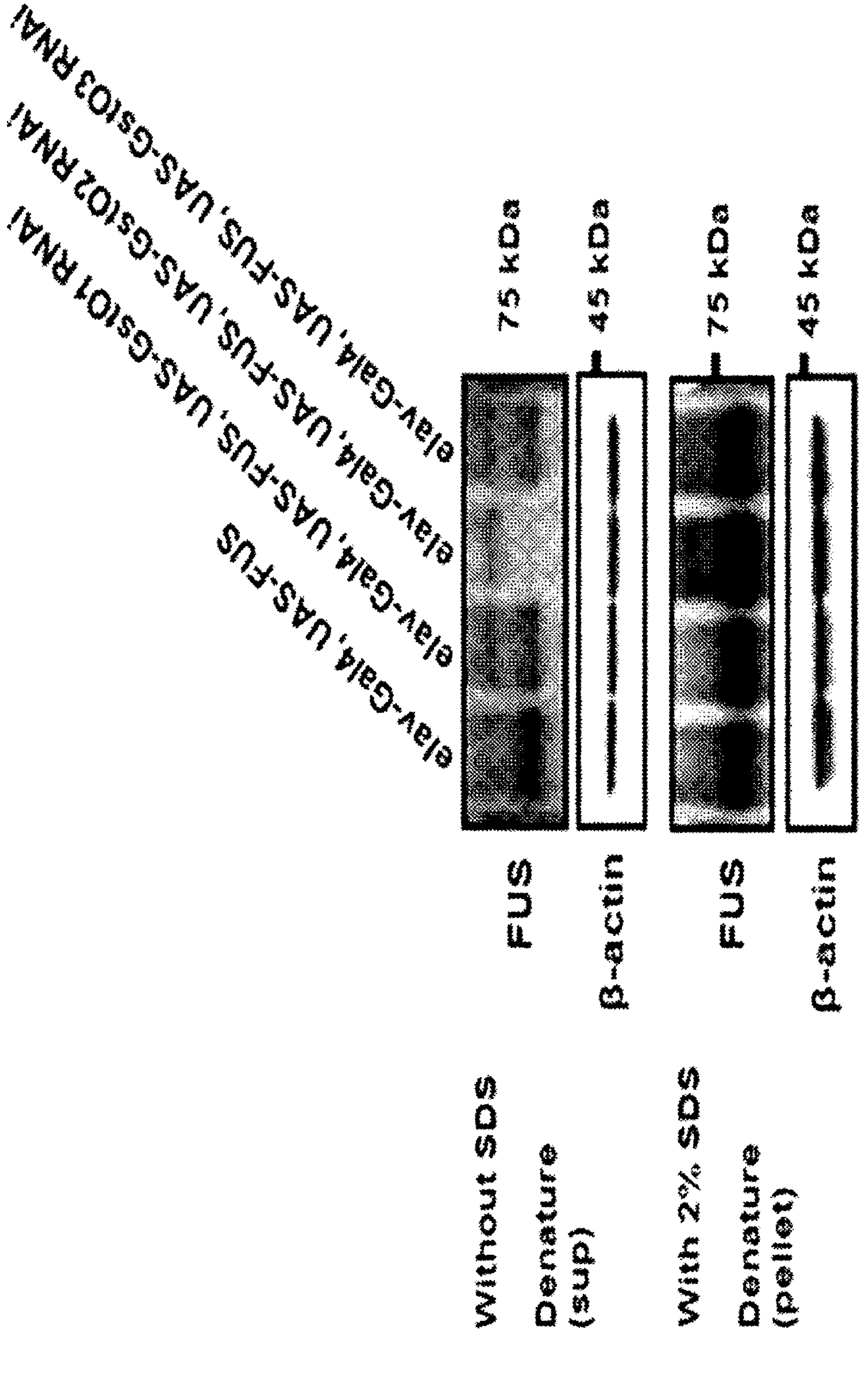
FIG. 13E shows the result of analyzing solubility to confirm a FUS aggregate according to GSTO1 or GstO3 knockdown.

On the other hand, as shown in FIG. 13E, the knockdown of either GSTO1 or GstO3 was not sufficient to improve FUS aggregation, as confirmed by immunoblotting.

Therefore, it is shown that GstO2 in the GstO family has a protective function in FUS-induced ALS by regulating the formation of a FUS aggregate in the cytoplasm.

The increased FUS expression in the cytoplasm is known to promote the binding of FUS and the mitochondria, and induce mitochondrial dysfunction (Deng et al., 2015), and to confirm whether GstO2 regulates the FUS level of the mitochondria, after coexpression of FUS and GstO2 in fly muscle tissue, the FUS level from the purified mitochondria was assessed by western blotting.

Figure 13F:
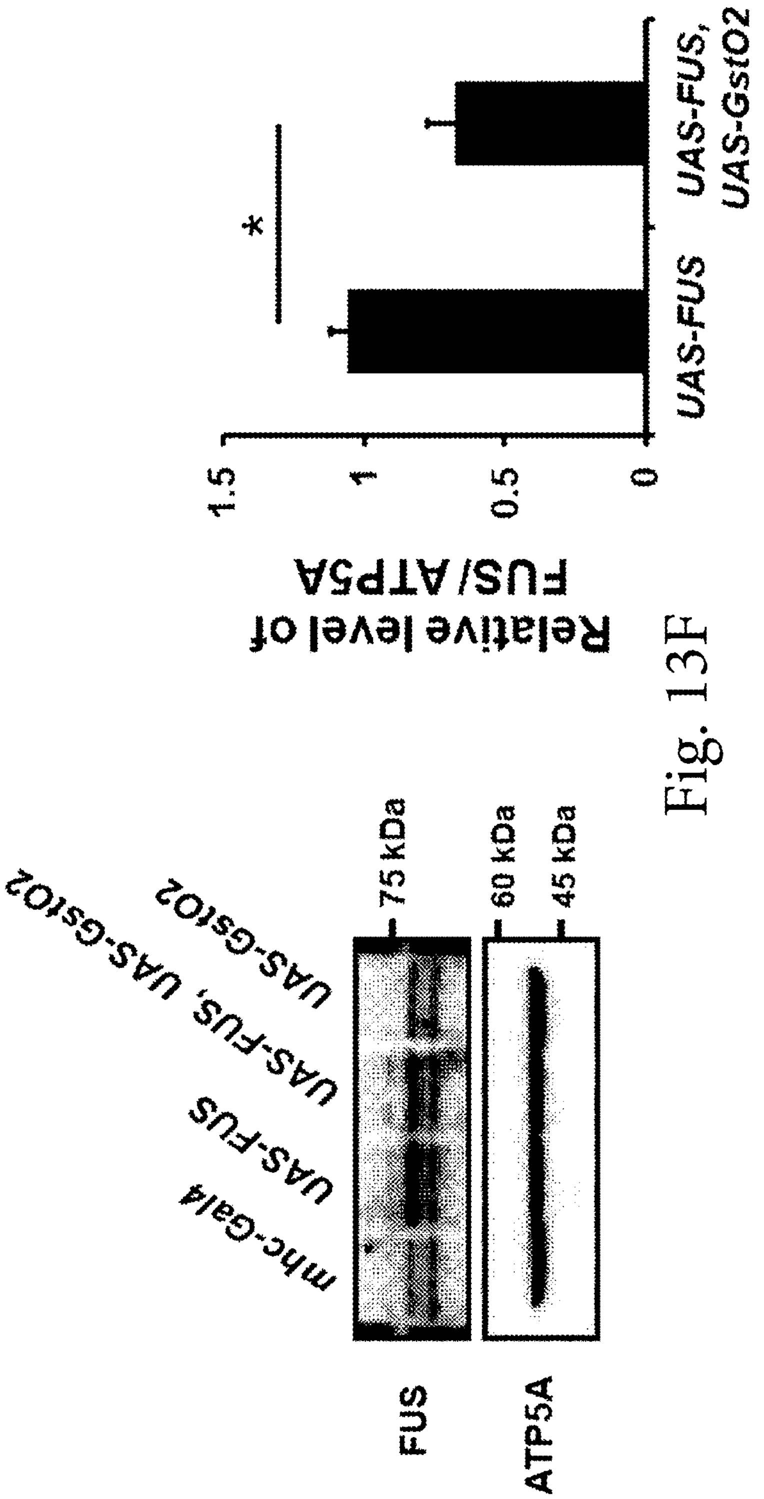
FIG. 13F shows the result of confirming a FUS level in the mitochondria of FUS-expressing flies according to GstO2.

As a result, as shown in FIG. 13F, it was confirmed that the mitochondria FUS level is remarkably reduced in the GstO2-coexpressing flies.

Example 12. Confirmation of Regulation of FUS Glutathionylation in *Drosophila* Neurons Due to GstO2

GstO2-mediated recovery of phenotypes of FUS-expressing flies may be involved in FUS glutathionylation, and therefore, the inventors hypothesized that GstO2 can regulate FUS glutathionylation and aggregation in the *Drosophila* brain, and to confirm this, the following experiments were performed.

First, as a result of a double immunofluorescence assay on the brain tissue of a FUS-expressing adult fly, as shown in FIG. 5A, it was confirmed that the FUS aggregate is simultaneously localized with GSH in the cytoplasm, but it was confirmed that GstO2 coexpression inhibits an increase in formation of a FUS aggregate, and reduces FUS glutathionylation. Subsequently, GstO2-downregulated cytoplasmic FUS glutathionylation-induced aggregation was assessed using RNAi. As a result, it was confirmed that GstO2 knockdown increases cytoplasmic FUS aggregates and glutathionylation.

From the above, it was predicted that GstO2-mediated deglutathionylation of FUS inhibits the formation of FUS aggregates in the cytoplasm of neurons, and is effectively used to delay FUS-mediated neurotoxicity.

Subsequently, it was investigated whether endogenous GstO2 interacts with FUS in neurons. As a result, as shown in FIG. 5B, endogenous GstO2 localization was confirmed by the fact that *Drosophila* neurons were dispersed in the cytoplasm, and endogenous GstO2 was co-localized with a FUS aggregate in the cytoplasm in FUS-expressing flies, supporting the interaction between GstO2 and FUS, and it can be inferred that GstO2 can play a role in FUS-induced ALS.

Example 13. Confirmation of Inhibition of FUSP525L-Induced Neurotoxicity and Insolubility in *Drosophila* Due to GstO2

According to previous research, FUS mutations have been identified in most ALS patients (Mackenzie et al., 2010), the FUS$^{P525L}$ variant shows cytoplasmic mislocalization and involvement in acute FUS-induced-ALS (Sun et al., 2011), FUS wild type and its variant FUS$^{P525L}$ are known to exhibit the same phenotypes such as rough eyes and decreased locomotive activity in *Drosophila* (Chen et al., 2016; Jackel et al., 2015).

Based on the result of confirming FUS$^{P525L}$ glutathionylation in the cytoplasm of neuro2a in FIG. 10C according to one embodiment of the present disclosure, it was predicted that GstO2 can contribute to the phenotypes generated by FUSP525L expression in the *Drosophila* brain, and the following experiments were performed.

More specifically, to confirm whether GstO2 expression can inhibit FUSP525L-induced locomotive defects, a FUS mutant type FUS$^{P525L}$ was expressed in neurons using elav-Gal4, and an experiment of confirming larval locomotive activity was performed. Here, the FUS$^{P525L}$ mutation did not exhibit higher toxicity than wild-type FUS.

Figure 15A:
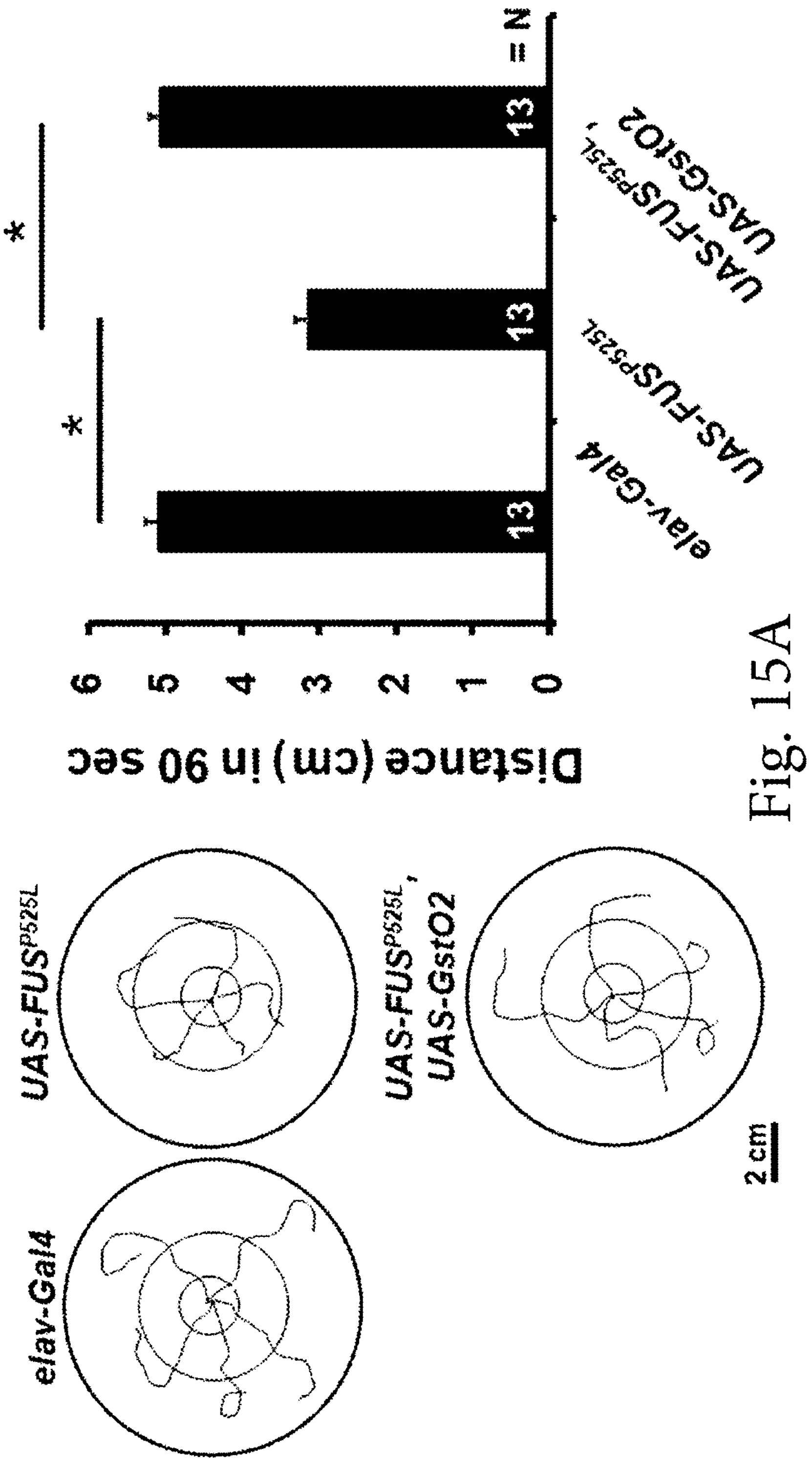
FIG. 15A shows the result of confirming the larva crawling activity of FUSP525L-expressing flies according to GstO2.

As a result, as shown in FIG. 15A, similar to FUS-expressing flies, it was confirmed that the crawling activity of larvae is decreased to approximately 40%, and coexpression of GstO2 causes crawling to be activated in the opposite direction, and as shown in FIG. 15B, GstO2 expression did not affect FUS$^{P525L}$ levels in the total extract of the adult fly brain.

Figure 15C:
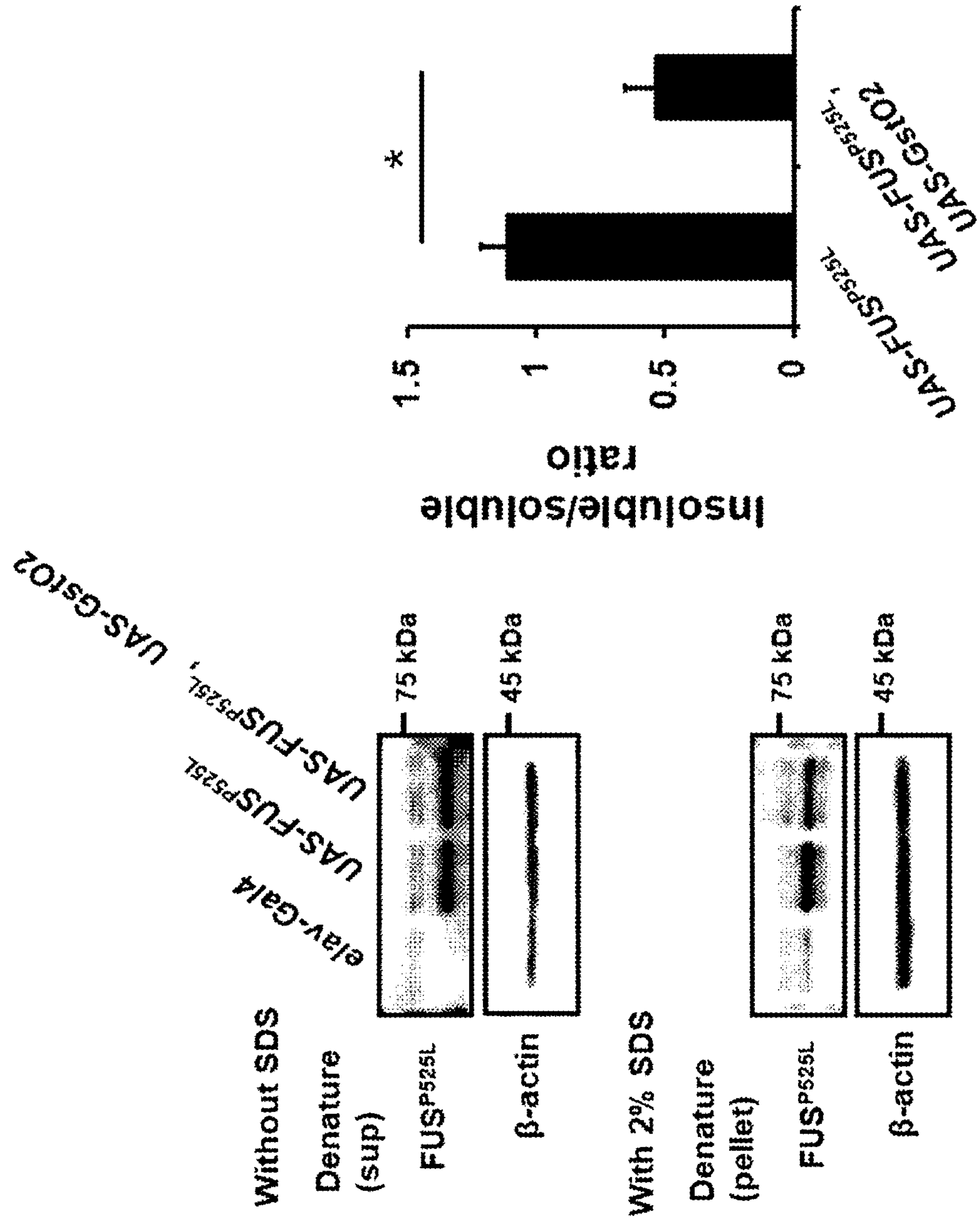
FIG. 15C shows the result of analyzing solubility to confirm a FUS aggregate of FUSP525L-expressing flies according to GstO2.

Subsequently, the effect of GstO2 on FUS$^{P525L}$ solubility was intended to be confirmed. As a result, as shown in FIG. 15C, compared to flies expressing FUS$^{P525L}$ alone, a decrease of 50% or more in the insoluble/soluble FUS$^{P525L}$ ratio in GstO2-coexpressing flies was demonstrated through quantification of soluble and insoluble FUS$^{P525L}$.

Overall, it was confirmed that GstO2 regulates FUS$^{P525L}$ toxicity through the formation of a protein aggregate.

Example 14. Confirmation of Regulation of FUS-Induced Neurotoxicity in Mammals

Figure 16A:
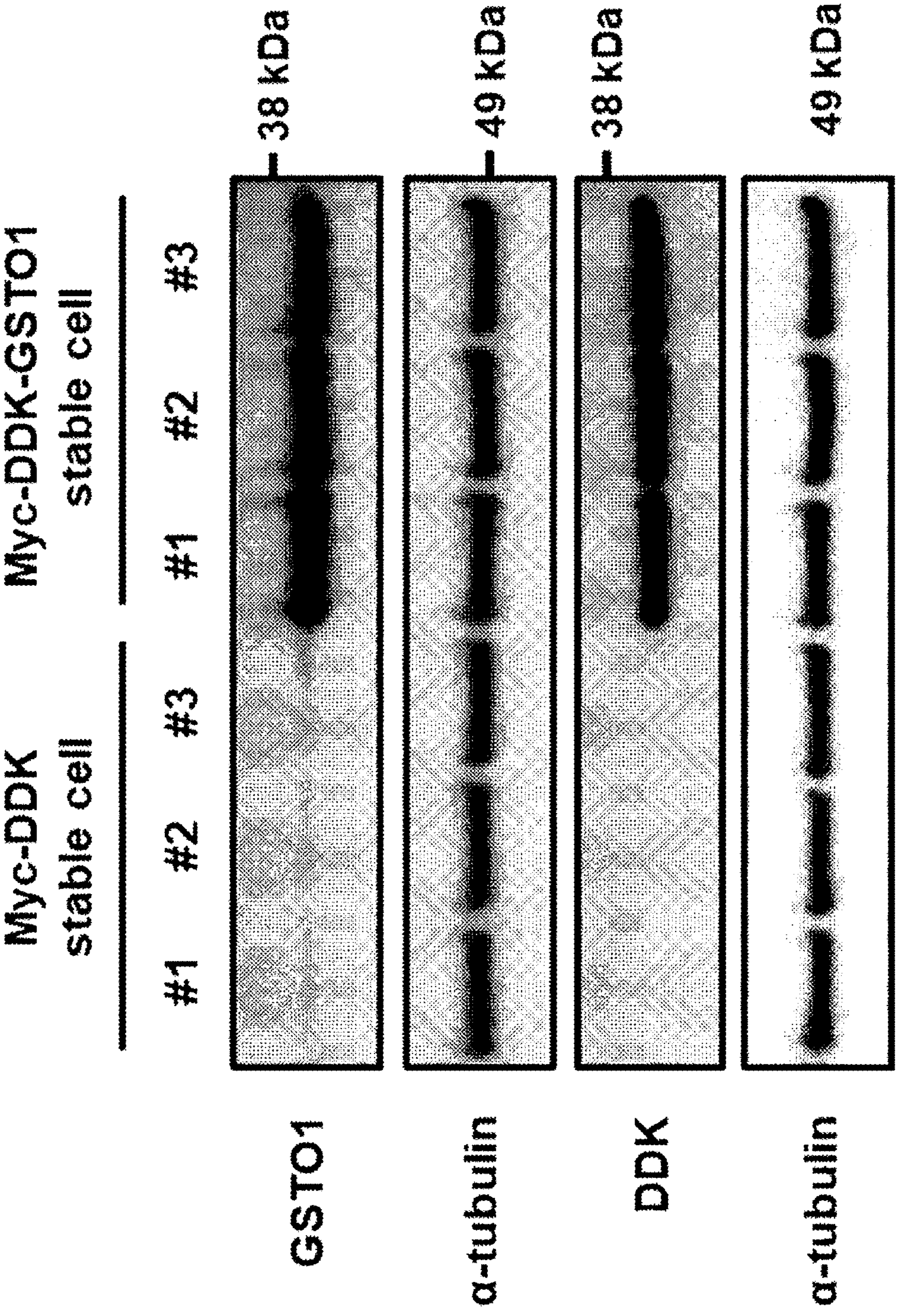
FIG. 16A shows the result of confirming GSTO1 expression in a stable N2a cell line expressing a Myc-DDK-GSTO1 fusion protein to confirm the regulation of FUS-induced neurotoxicity of GSTO1, which is a human homologous chromosome of GstO2.

To confirm that the recovery effect of GstO2 on FUS-induced neurotoxicity is also applied to a mammalian system, a stable N2a cell line expressing a Myc-DDK-GSTO1 fusion protein for GSTO1, which is a human homologous chromosome of GstO2, was developed (see FIG. 16A), and after the GSTO1 stable cell line was transfected with GFP-tagged FUS, the GSTO1 effect on FUS was investigated.

Figure 16B:
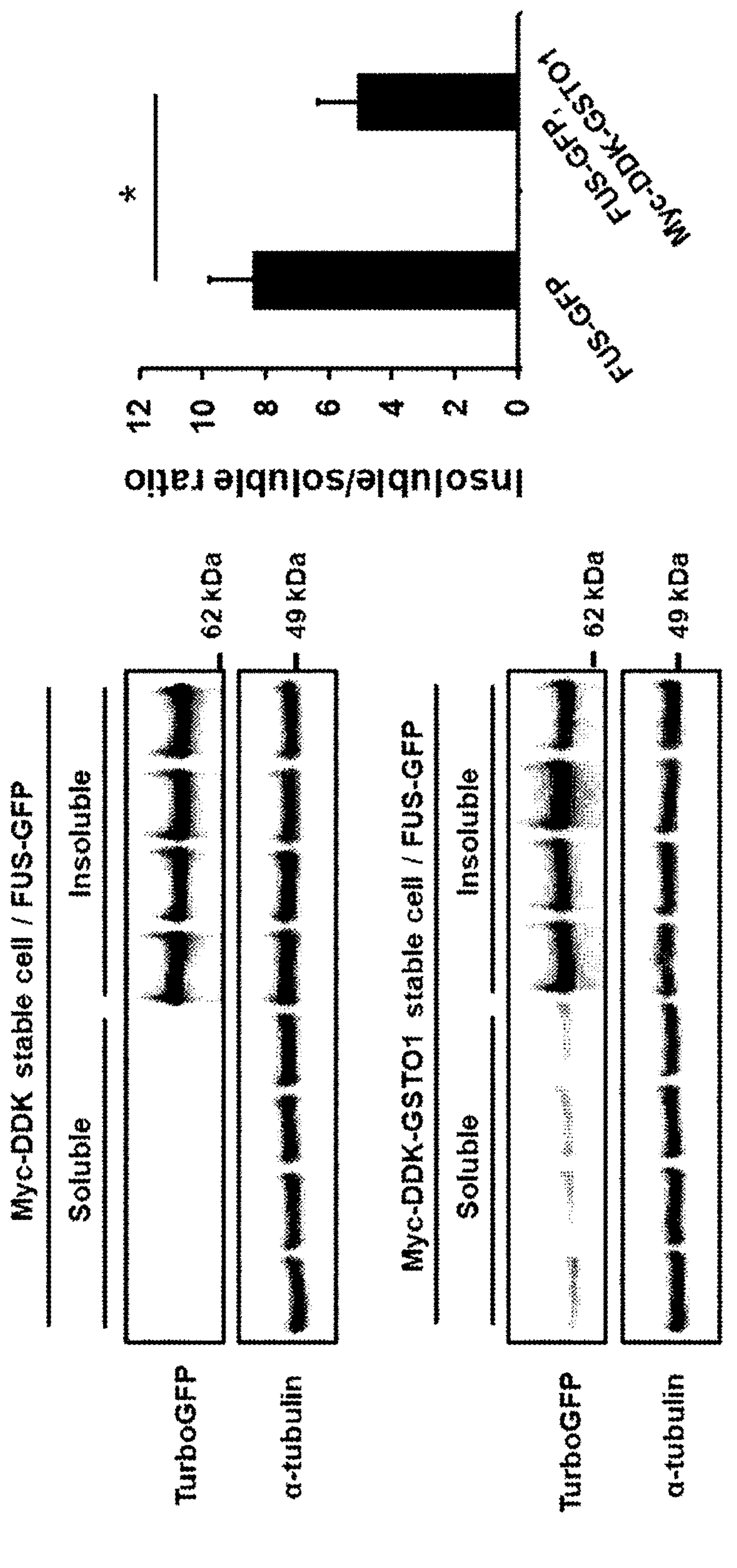
FIG. 16B shows the result of analyzing solubility to confirm a FUS aggregate according to GSTO1, which is a human homologous chromosome of GstO2.

As a result, as shown in FIG. 16B, compared to the FUS-expressing flies, a 50% or more decrease in insoluble/soluble FUS ratio in GSTO1-coexpressing flies was confirmed through soluble and insoluble FUS quantification.

Subsequently, based on previous research results showing that the increased expression of FUS promotes apoptosis in mammalian neurons (Deng et al., 2015), to investigate the effect of GSTO 1 on FUS-induced apoptosis, N2a cells were identified by staining with an anti-cleaved caspase-3 antibody.

As a result, as shown in FIG. 16C, it was confirmed that a cleaved caspase-3 signal is significantly increased in N2a cells expressing FUS-GFP compared to the control cells, but when FUS was coexpressed with GSTO1, it was confirmed that the cleaved caspase-3 signal was reduced and the neuronal cell death phenotype was restored.

Therefore, it was confirmed that the expression of GSTO1, which is a human homologous chromosome of GstO2, also improves FUS insolubility and FUS-induced cell apoptosis in mammalian neuron models of ALS.

It should be understood by those of ordinary skill in the art that the above description of the present disclosure is exemplary, and the exemplary embodiments disclosed herein can be easily modified into other specific forms without departing from the technical spirit or essential features of the present disclosure. Therefore, the exemplary embodiments described above should be interpreted as illustrative and not limited in any aspect.

INDUSTRIAL APPLICABILITY

ALS can be early diagnosed using a marker composition for diagnosing a neurodegenerative disease, which includes a glutathionylated FUS protein, according to the present disclosure, and a pharmaceutical composition for preventing or treating a neurodegenerative disease, which includes a GSTO gene or a protein encoding the gene as an active ingredient, may be used in treatment of ALS.

The invention claimed is:

1. A method of diagnosing amyotrophic lateral sclerosis (ALS) in a subject, comprising:

a) measuring a level of glutathionylated FUS protein from a subject-derived neuron sample using an immunoprecipitation or a tissue staining assay, wherein the immunoprecipitation or the tissue staining assay determines the level of glutathionylated FUS protein by quantifying the amount of glutathione (GSH) covalently bound to FUS protein in the subject-derived neuron sample;

b) comparing the level of glutathionylated FUS protein with a level of a glutathionylated FUS protein of a normal control sample, wherein an increased level of the glutathionylated FUS protein compared to the glutathionylated FUS protein of the normal control sample is indicative of the subject having ALS;

c) demonstrating that omega class glutathione transferase 1 (GSTO1) or omega class glutathione transferase 2 (GSTO2) induces deglutathionylation of the glutathionylated FUS protein to inhibit brain cytoplasmic aggregation and neurotoxicity; and d) administering omega class glutathione transferase 1 (GSTO1) or omega class glutathione transferase 2 (GSTO2) protein or a gene encoding the same to the subject indicated as having ALS.

2. The method of claim 1, wherein the FUS protein consists of the amino acid sequence represented by SEQ ID NO: 1.

3. The method of claim 1, wherein the glutathionylated FUS protein is glutathionylated at a Cys-447 residue.

4. The method of claim 1, wherein the GSTO1 gene consists of the nucleotide sequence represented by SEQ ID NO: 2.

5. The method of claim 1, wherein the neuron is a brain neuron.

* * * * *

SEQUENCE LISTING

```
<160> NUMBER OF SEQ ID NOS: 5

<210> SEQ ID NO 1
<211> LENGTH: 526
<212> TYPE: PRT
<213> ORGANISM: Artificial Sequence
<220> FEATURE:
<223> OTHER INFORMATION: FUS Protein

<400> SEQUENCE: 1

Met Ala Ser Asn Asp Tyr Thr Gln Gln Ala Thr Gln Ser Tyr Gly Ala
1               5                   10                  15

Tyr Pro Thr Gln Pro Gly Gln Gly Tyr Ser Gln Gln Ser Ser Gln Pro
                20                  25                  30

Tyr Gly Gln Gln Ser Tyr Ser Gly Tyr Ser Gln Ser Thr Asp Thr Ser
        35                  40                  45

Gly Tyr Gly Gln Ser Ser Tyr Ser Ser Tyr Gly Gln Ser Gln Asn Thr
    50                  55                  60

Gly Tyr Gly Thr Gln Ser Thr Pro Gln Gly Tyr Gly Ser Thr Gly Gly
65                  70                  75                  80

Tyr Gly Ser Ser Gln Ser Ser Gln Ser Ser Tyr Gly Gln Gln Ser Ser
                85                  90                  95

Tyr Pro Gly Tyr Gly Gln Gln Pro Ala Pro Ser Ser Thr Ser Gly Ser
                100                 105                 110

Tyr Gly Ser Ser Ser Gln Ser Ser Ser Tyr Gly Gln Pro Gln Ser Gly
        115                 120                 125

Ser Tyr Ser Gln Gln Pro Ser Tyr Gly Gly Gln Gln Ser Tyr Gly
    130                 135                 140

Gln Gln Gln Ser Tyr Asn Pro Pro Gln Gly Tyr Gly Gln Gln Asn Gln
145                 150                 155                 160

Tyr Asn Ser Ser Ser Gly Gly Gly Gly Gly Gly Gly Gly Gly Gly Asn
                165                 170                 175

Tyr Gly Gln Asp Gln Ser Ser Met Ser Ser Gly Gly Gly Ser Gly Gly
                180                 185                 190

Gly Tyr Gly Asn Gln Asp Gln Ser Gly Gly Gly Gly Ser Gly Gly Tyr
        195                 200                 205

Gly Gln Gln Asp Arg Gly Gly Arg Gly Arg Gly Gly Ser Gly Gly Gly
    210                 215                 220

Gly Gly Gly Gly Gly Gly Gly Tyr Asn Arg Ser Ser Gly Gly Tyr Glu
225                 230                 235                 240

Pro Arg Gly Arg Gly Gly Gly Arg Gly Gly Arg Gly Gly Met Gly Gly
                245                 250                 255

Ser Asp Arg Gly Gly Phe Asn Lys Phe Gly Gly Pro Arg Asp Gln Gly
                260                 265                 270

Ser Arg His Asp Ser Glu Gln Asp Asn Ser Asp Asn Asn Thr Ile Phe
        275                 280                 285
```

-continued

```
Val Gln Gly Leu Gly Glu Asn Val Thr Ile Glu Ser Val Ala Asp Tyr
    290                 295                 300

Phe Lys Gln Ile Gly Ile Ile Lys Thr Asn Lys Lys Thr Gly Gln Pro
305                 310                 315                 320

Met Ile Asn Leu Tyr Thr Asp Arg Glu Thr Gly Lys Leu Lys Gly Glu
                325                 330                 335

Ala Thr Val Ser Phe Asp Asp Pro Pro Ser Ala Lys Ala Ala Ile Asp
            340                 345                 350

Trp Phe Asp Gly Lys Glu Phe Ser Gly Asn Pro Ile Lys Val Ser Phe
        355                 360                 365

Ala Thr Arg Arg Ala Asp Phe Asn Arg Gly Gly Gly Asn Gly Arg Gly
    370                 375                 380

Gly Arg Gly Arg Gly Gly Pro Met Gly Arg Gly Gly Tyr Gly Gly Gly
385                 390                 395                 400

Gly Ser Gly Gly Gly Gly Arg Gly Gly Phe Pro Ser Gly Gly Gly Gly
                405                 410                 415

Gly Gly Gly Gln Gln Arg Ala Gly Asp Trp Lys Cys Pro Asn Pro Thr
            420                 425                 430

Cys Glu Asn Met Asn Phe Ser Trp Arg Asn Glu Cys Asn Gln Cys Lys
        435                 440                 445

Ala Pro Lys Pro Asp Gly Pro Gly Gly Gly Pro Gly Gly Ser His Met
    450                 455                 460

Gly Gly Asn Tyr Gly Asp Asp Arg Arg Gly Gly Arg Gly Gly Tyr Asp
465                 470                 475                 480

Arg Gly Gly Tyr Arg Gly Arg Gly Gly Asp Arg Gly Gly Phe Arg Gly
                485                 490                 495

Gly Arg Gly Gly Gly Asp Arg Gly Gly Phe Gly Pro Gly Lys Met Asp
            500                 505                 510

Ser Arg Gly Glu His Arg Gln Asp Arg Arg Glu Arg Pro Tyr
        515                 520                 525
```

<210> SEQ ID NO 2
<211> LENGTH: 726
<212> TYPE: DNA
<213> ORGANISM: Artificial Sequence
<220> FEATURE:
<223> OTHER INFORMATION: GSTO1 Polynucleotide

<400> SEQUENCE: 2

```
atgtccgggg agtcagccag gagcttgggg aagggaagcg cgcccccggg gccggtcccg      60

gagggctcga tccgcatcta cagcatgagg ttctgcccgt ttgctgagag gacgcgtcta     120

gtcctgaagg ccaagggaat caggcatgaa gtcatcaata tcaacctgaa aaataagcct     180

gagtggttct ttaagaaaaa tccctttggt ctggtgccag ttctggaaaa cagtcagggt     240

cagctgatct acgagtctgc catcacctgt gagtacctgg atgaagcata cccagggaag     300

aagctgttgc cggatgaccc ctatgagaaa gcttgccaga agatgatctt agagttgttt     360

tctaaggtgc catccttggt aggaagcttt attagaagcc aaaataaaga agactatgct     420

ggcctaaaag aagaatttcg taaagaattt accaagctag aggaggttct gactaataag     480

aagacgacct tctttggtgg caattctatc tctatgattg attacctcat ctggccctgg     540

tttgaacggc tggaagcaat gaagttaaat gagtgtgtag accacactcc aaaactgaaa     600

ctgtggatgg cagccatgaa ggaagatccc acagtctcag ccctgcttac tagtgagaaa     660

gactggcaag gtttcctaga gctctactta cagaacagcc ctgaggcctg tgactatggg     720
```

ctctga 726

<210> SEQ ID NO 3
<211> LENGTH: 241
<212> TYPE: PRT
<213> ORGANISM: Artificial Sequence
<220> FEATURE:
<223> OTHER INFORMATION: GSTO1 Protein

<400> SEQUENCE: 3

Met Ser Gly Glu Ser Ala Arg Ser Leu Gly Lys Gly Ser Ala Pro Pro
1 5 10 15

Gly Pro Val Pro Glu Gly Ser Ile Arg Ile Tyr Ser Met Arg Phe Cys
20 25 30

Pro Phe Ala Glu Arg Thr Arg Leu Val Leu Lys Ala Lys Gly Ile Arg
35 40 45

His Glu Val Ile Asn Ile Asn Leu Lys Asn Lys Pro Glu Trp Phe Phe
50 55 60

Lys Lys Asn Pro Phe Gly Leu Val Pro Val Leu Glu Asn Ser Gln Gly
65 70 75 80

Gln Leu Ile Tyr Glu Ser Ala Ile Thr Cys Glu Tyr Leu Asp Glu Ala
85 90 95

Tyr Pro Gly Lys Lys Leu Leu Pro Asp Asp Pro Tyr Glu Lys Ala Cys
100 105 110

Gln Lys Met Ile Leu Glu Leu Phe Ser Lys Val Pro Ser Leu Val Gly
115 120 125

Ser Phe Ile Arg Ser Gln Asn Lys Glu Asp Tyr Ala Gly Leu Lys Glu
130 135 140

Glu Phe Arg Lys Glu Phe Thr Lys Leu Glu Glu Val Leu Thr Asn Lys
145 150 155 160

Lys Thr Thr Phe Phe Gly Gly Asn Ser Ile Ser Met Ile Asp Tyr Leu
165 170 175

Ile Trp Pro Trp Phe Glu Arg Leu Glu Ala Met Lys Leu Asn Glu Cys
180 185 190

Val Asp His Thr Pro Lys Leu Lys Leu Trp Met Ala Ala Met Lys Glu
195 200 205

Asp Pro Thr Val Ser Ala Leu Leu Thr Ser Glu Lys Asp Trp Gln Gly
210 215 220

Phe Leu Glu Leu Tyr Leu Gln Asn Ser Pro Glu Ala Cys Asp Tyr Gly
225 230 235 240

Leu

<210> SEQ ID NO 4
<211> LENGTH: 756
<212> TYPE: DNA
<213> ORGANISM: Artificial Sequence
<220> FEATURE:
<223> OTHER INFORMATION: Gsto2 Polynucleotide

<400> SEQUENCE: 4
atggccctgc cgcaaaagca cttcaagagg ggttccacca agcccgagct gccagaagat 60
ggagttcctc gtttcttttc catggcattc tgccccttca gccaccgagt tcgtctgatg 120
ctggccgcca aacatattga acatcataag atctacgtcg atttgattga gaagcctgaa 180
tggtacaagg atttcagtcc tctgggcaaa gtgccagccc tgcagcttac tggggtgaag 240
gaccaaccga ccctcgtgga gtcgctcatc atagcagagt acttggacca gcaatatccc 300

-continued

```
cagacgcgac tctttcccac ggatccgctt cagaaggcgc tggacaagat tctaatcgaa    360

cgttttgctc cagtggtcag tgccatttat cctgtgctga cttgtaatcc caacgctccg    420

aaagatgcca taccgaactt cgagaatgcc ttggatgttt ttgaagtgga gttgggcaaa    480

agaggaacgc cctactttgc cggccagcac attggaatcg tggactacat gatttggcct    540

tggttcgaac gttttcccag catgaagatc aatacggagc aaaagtatga gctggataca    600

aaacgatttg agaagctgct caagtggcgc gatttgatga cccaggatga ggttgtgcag    660

aagacagctt tggatgtcca gttgcatgct gagttccaga aatcgaagac ccttggaaat    720

ccccagtacg acattgcctt caagggtaca ccatag                              756
```

<210> SEQ ID NO 5
<211> LENGTH: 251
<212> TYPE: PRT
<213> ORGANISM: Artificial Sequence
<220> FEATURE:
<223> OTHER INFORMATION: GstO2 protein

<400> SEQUENCE: 5

```
Met Ala Leu Pro Gln Lys His Phe Lys Arg Gly Ser Thr Lys Pro Glu
1               5                   10                  15

Leu Pro Glu Asp Gly Val Pro Arg Phe Phe Ser Met Ala Phe Cys Pro
            20                  25                  30

Phe Ser His Arg Val Arg Leu Met Leu Ala Ala Lys His Ile Glu His
        35                  40                  45

His Lys Ile Tyr Val Asp Leu Ile Glu Lys Pro Glu Trp Tyr Lys Asp
    50                  55                  60

Phe Ser Pro Leu Gly Lys Val Pro Ala Leu Gln Leu Thr Gly Val Lys
65                  70                  75                  80

Asp Gln Pro Thr Leu Val Glu Ser Leu Ile Ile Ala Glu Tyr Leu Asp
                85                  90                  95

Gln Gln Tyr Pro Gln Thr Arg Leu Phe Pro Thr Asp Pro Leu Gln Lys
            100                 105                 110

Ala Leu Asp Lys Ile Leu Ile Glu Arg Phe Ala Pro Val Val Ser Ala
        115                 120                 125

Ile Tyr Pro Val Leu Thr Cys Asn Pro Asn Ala Pro Lys Asp Ala Ile
    130                 135                 140

Pro Asn Phe Glu Asn Ala Leu Asp Val Phe Glu Val Glu Leu Gly Lys
145                 150                 155                 160

Arg Gly Thr Pro Tyr Phe Ala Gly Gln His Ile Gly Ile Val Asp Tyr
                165                 170                 175

Met Ile Trp Pro Trp Phe Glu Arg Phe Pro Ser Met Lys Ile Asn Thr
            180                 185                 190

Glu Gln Lys Tyr Glu Leu Asp Thr Lys Arg Phe Glu Lys Leu Leu Lys
        195                 200                 205

Trp Arg Asp Leu Met Thr Gln Asp Glu Val Val Gln Lys Thr Ala Leu
    210                 215                 220

Asp Val Gln Leu His Ala Glu Phe Gln Lys Ser Lys Thr Leu Gly Asn
225                 230                 235                 240

Pro Gln Tyr Asp Ile Ala Phe Lys Gly Thr Pro
                245                 250
```